United States Patent [19]

Shimada et al.

[11] Patent Number: 5,164,289

[45] Date of Patent: Nov. 17, 1992

[54] DYE FORMING COUPLER AND SILVER HALIDE COLOR PHOTOGRAPHIC MATERIAL CONTAINING THE SAME AND METHOD FOR FORMING COLOR IMAGE

[75] Inventors: Yasuhiro Shimada; Yoshio Ishii; Jiro Tsukahara; Makoto Suzuki; Koushin Matsuoka, all of Kanagawa, Japan

[73] Assignee: Fuji Photo Film Co., Ltd., Kanagawa, Japan

[21] Appl. No.: 696,848

[22] Filed: May 7, 1991

[30] Foreign Application Priority Data

May 11, 1990 [JP] Japan .................. 2-121670
Apr. 10, 1991 [JP] Japan .................. 3-103593

[51] Int. Cl.$^5$ .............................. G03C 7/38
[52] U.S. Cl. .................. 430/384; 430/385; 430/558
[58] Field of Search .................. 430/558, 384, 385

[56] References Cited

U.S. PATENT DOCUMENTS

| | | | |
|---|---|---|---|
| 4,728,598 | 3/1988 | Bailey et al. | 430/387 |
| 4,873,183 | 10/1989 | Tachibana et al. | 430/550 |
| 4,916,051 | 4/1990 | Tachibana et al. | 439/558 |

FOREIGN PATENT DOCUMENTS

| | | | |
|---|---|---|---|
| 1-040831 | 2/1989 | Japan | 430/558 |
| 1-142633 | 6/1989 | Japan | 430/558 |

*Primary Examiner*—Lee C. Wright
*Attorney, Agent, or Firm*—Birch, Stewart, Kolasch & Birch

[57] ABSTRACT

A silver halide photographic material containing at least one dye forming coupler represented by formula (I):

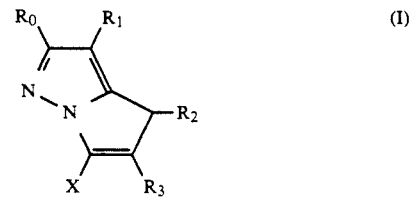

wherein $R_0$ represents a hydrogten atom or a substituent; $R_1$ and $R_3$ each represents a substituent; $R_2$ represents an electron attracting group; X represents a hydrogen atom or a group releasable on coupling with an oxidation product of an aromatic primary amine derivative, and a silver halide photographic material containing the same are disclosed. The coupler of formula (I) exhibits excellent coupling activity and provides a dye which has a sharp absorption spectrum with no side absorption in the blue and green light regions and exhibits stability to light, heat and moisture and improved color reproducibility.

16 Claims, 1 Drawing Sheet

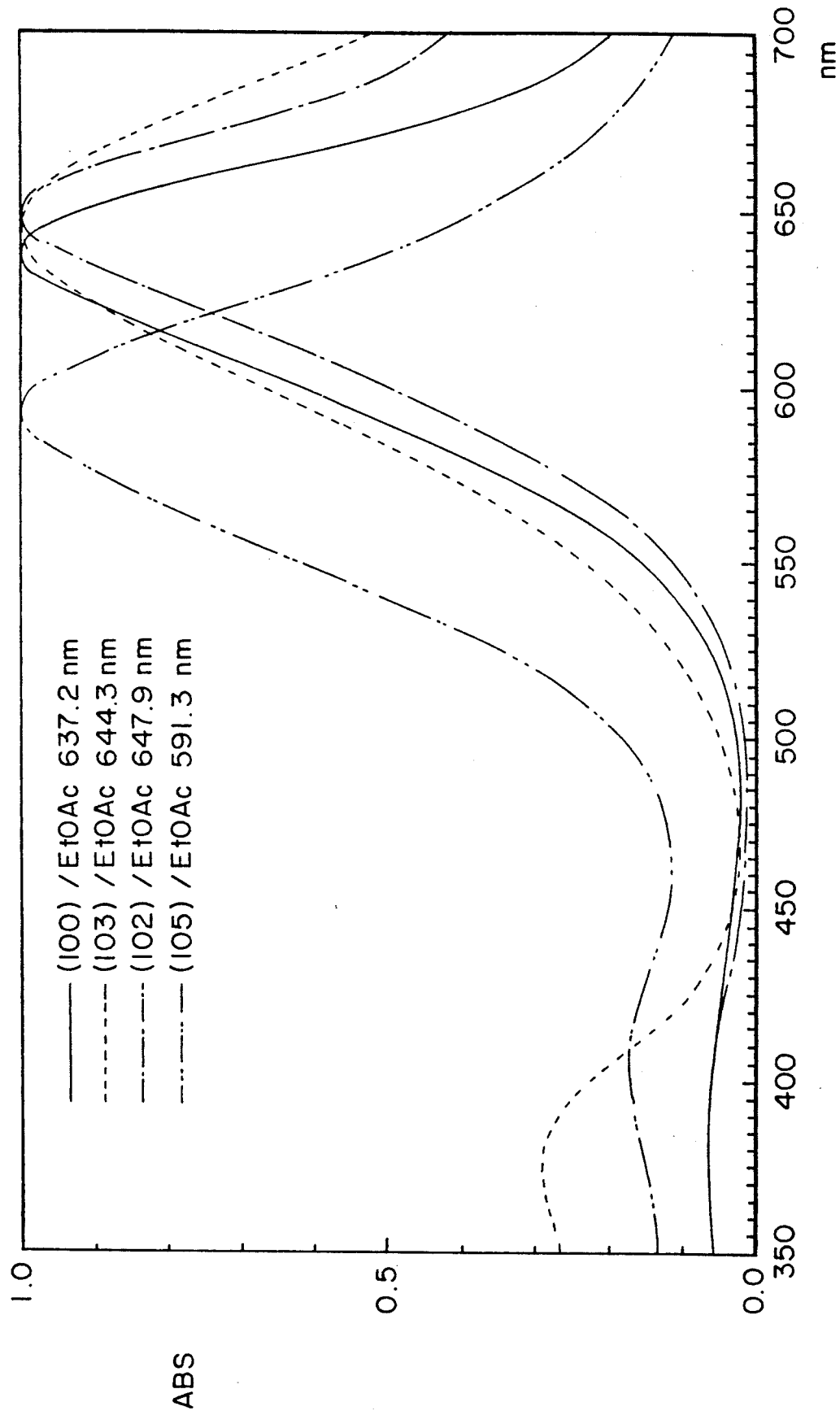

DYE FORMING COUPLER AND SILVER HALIDE COLOR PHOTOGRAPHIC MATERIAL CONTAINING THE SAME AND METHOD FOR FORMING COLOR IMAGE

FIELD OF THE INVENTION

The present invention relates to a novel dye forming coupler which is useful for synthesizing filters, paints, inks, or dyes for image, information recording or printing or is particularly useful in silver halide color photographic materials, to a silver halide light-sensitive material containing the same and to a method of forming a color image. More particularly, the present invention relates to a silver halide color photographic material having improved color reproducibility by using a novel dye forming coupler.

BACKGROUND OF THE INVENTION

It is well known that an aromatic primary amine developing agent oxidized with an exposed silver halide reacts with a coupler to produce indophenol, indoaniline, indamine, azomethine, phenoxazine, phenazine or like dyes to form a dye image. In this photographic image formation system, a subtractive color process in which a color image is formed from a yellow dye, a magenta dye, and a cyan dye is used.

For cyan dye image formation, phenol cyan couplers or naphthol cyan couplers are generally employed. However, these cyan couplers have undesired absorption in the green region, causing considerable reduction in color reproducibility.

Cyan couplers which have been so far proposed to avoid this problem include pyrazoloazole couplers as disclosed in U.S. Pat. No. 4,873,183 and 2,4-diphenylimidazole couplers as disclosed in EP 249453A2. Cyan dyes produced by these couplers show reductions in their undesired absorption in the shorter wavelength side in favor of color reproduction as compared with conventional dyes. However, these couplers are still unsatisfactory in accomplishing sufficient color reproduction and their practical use results in problems requiring solution. For example, they have low coupling activity and very low stability against heat and light, or when processed with a processing solution having bleaching ability (i.e., a bleaching bath or bleach-fix bath) with a low oxidizing power or an exhausted processing solution having bleaching ability, they undergo a reduction in developed color density.

Further, U.S. Pat. No. 4,728,598 proposes pyrazoloimidazole couplers. These couplers, though exhibiting improved coupling activity, are insufficient in hue.

SUMMARY OF THE INVENTION

An object of the present invention is to provide a novel cyan coupler which exhibits excellent coupling activity and provides a cyan dye free from side absorptions in the blue and green regions Another object of the present invention is to provide a silver halide photographic material which has excellent color reproducibility and provides a dye image stable to light, heat or moisture.

A further object of the present invention is to provide a silver halide color photographic material which undergoes substantially no reduction in developed color density even when processed with a processing solution having bleaching ability with a weak oxidizing power or with an exhausted processing solution having poor bleaching ability.

The objects of the present invention are accomplished by:

(1) a dye forming coupler represented by formula (I):

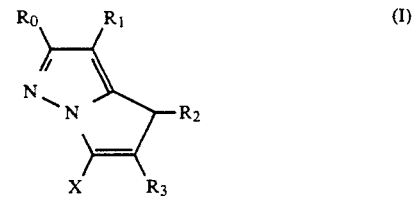

wherein $R_0$ represents a hydrogen atom or a substituent; $R_1$ and $R_3$ each represents a substituent; $R_2$ represents an electron attracting group; X represents a hydrogen atom or a group releasable on coupling with an oxidation product of an aromatic primary amine derivative;

(2) a silver halide photographic material containing at least one said dye forming coupler: and (3) a method for processing a silver halide color photographic material which comprises processing a color developed silver halide color photographic material containing at least one said dye forming coupler with a processing solution having bleaching ability containing an aminopolycarboxylic acid iron (II) complex salt as an oxidizing agent.

BRIEF DESCRIPTION OF THE DRAWING

FIG. 1 shows the absorption spectra in ethyl acetate of azomethine dyes (100) and (102) produced by a coupling reaction of the couplers of the present invention with a developing agent and of azomethine dyes (103) and (105) produced by a coupling reaction of the comparative couplers with a developing agent, with the absorption spectrum of dye (100) shown by the solid line, that of dye (102) by the one-dot broken line, that of dye (105) by the two-dot broken line and that of (103) by the broken line.

DESCRIPTION OF THE INVENTION

In formula (I), $R_2$ represents an electron attracting group, and preferably a substituent having a Hammett's $\sigma_p$ value of not less than 0.10, more preferably not less than 0.35, and particularly preferably not less than 0.60. The "Hammett's $\sigma_p$ value" as used herein is preferably the value reported by Hansch, C. Leo, et al. (see, e.g., J. Med. Chem., Vol. 16, p. 1207 (1973), ibid., Vol. 20, p. 304 (1977)).

The terminology "aliphatic group" as used herein means a straight chain, branched or cyclic, and saturated or unsaturated aliphatic hydrocarbon group, including an alkyl group, an alkenyl group, and alkynyl group. Typical examples of monovalent aliphatic groups are methyl, ethyl, n-butyl, dodecyl, octadecyl, eicosenyl, isopropyl, t-butyl, t-octyl, t-dodecyl, cyclohexyl, cyclopentyl, allyl, vinyl, 2-hexadecenyl, and propargyl groups, with the alkyl group being preferred.

The terminology "aromatic group" as used herein means an aryl group which may be substituted with other groups. Typical examples of the aromatic group include a phenyl group and a naphthyl group.

The terminology "heterocyclic group" as used herein means a saturated or unsaturated ring, which may be substituted with other groups, containing as a hetero atom at least one of a nitrogen atom, a sulfur atom and an oxygen atom. Typical examples of the heterocyclic group include an imidazolyl group, a pyridyl group, a furyl group, a thienyl group, a thiazolyl group, a triazolyl group and a tetrazolyl group.

Substituents (or atoms) having a Hammett's $\sigma_p$ value of 0.10 or higher include a chlorine atom, a bromine atom, an iodine atom, a carboxyl group, a cyano group, a nitro group, a halogen-substituted alkyl group (e.g., trichloromethyl, trifluoromethyl, chloromethyl, trifluoromethylthiomethyl, trifluoromethanesulfonylmethyl, perfluorobutyl), an aliphatic, aromatic or heterocyclic acyl group (e.g., formyl, acetyl, benzoyl), an aliphatic, aromatic or heterocyclic sulfonyl group (e.g., trifluoromethanesulfonyl, methanesulfonyl, benzenesulfonyl), a carbamoyl group (e.g., carbamoyl, methylcarbamoyl, phenylcarbamoyl, 2-chlorophenylcarbamoyl), an alkoxycarbonyl group (e.g., methoxycarbonyl, ethoxycarbonyl, diphenylmethylcarbonyl), a substituted aromatic group (e.g., pentachlorophenyl, pentafluorophenyl, 2,4-dimethanesulfonylphenyl, 2-trifluoromethylphenyl), a heterocyclic group (e.g., 2-benzoxazolyl, 2-benzothiazolyl, 1-phenyl-2-benzimidazolyl, 1-tetrazolyl), an azo group (e.g., phenylazo), a ditrifluoromethylamino group, a trifluoromethoxy group, an alkylsulfonyloxy group (e.g., methanesulfonyloxy), an acyloxy group (e.g., acetyloxy, benzoyloxy), an arylsulfonyloxy group (e.g., benzenesulfonyloxy), a phosphoryl group (e.g., dimethoxyphosphoryl, diphenylphosphoryl), and a sulfamoyl group (e.g., N-ethylsulfamoyl, N,N-dipropylsulfamoyl, N-(2-dodecyloxyethyl)sulfamoyl,N-ethyl-N-dodecylsulfamoyl,N,N-diethylsulfamoyl).

Substituents having a Hammett's $\sigma_p$ value of 0.35 or higher include a cyano group, a nitro group, a carboxyl group, a fluorine-substituted alkyl group (e.g., trifluoromethyl, perfluorobutyl), an aliphatic, aromatic or heterocyclic acyl group (e.g., acetyl, benzoyl, formyl), an aliphatic, aromatic or heterocyclic sulfonyl group (e.g., trifluoromethanesulfonyl, methanesulfonyl, benzenesulfonyl), a carbamoyl group (e.g., carbamoyl, methylcarbamoyl, phenylcarbamoyl, 2-chlorophenyl carbamoyl), an alkoxycarbonyl group (e.g., methoxycarbonyl, ethoxycarbonyl, diphenylmethylcarbonyl), a fluorine- or sulfonyl-substituted aromatic group (e.g., pentafluorophenyl, 2,4-dimethanesulfonylphenyl), a heterocyclic group (e.g., 1-tetrazolyl), an azo group (e.g., phenylazo), an alkylsulfonyloxy group (e.g., methanesulfonyloxy), a phosphoryl group (e.g., dimethoxyphosphoryl, diphenylphosphoryl), a sulfamoyl group.

Substituents having a Hammett's $\sigma_p$ value of 0.60 or higher include a cyano group, a nitro group, and an aliphatic, aromatic or heterocyclic sulfonyl group (e.g., trifluoromethanesulfonyl, difluoromethanesulfonyl, methanesulfonyl, benzenesulfonyl).

$R_2$ most preferably represent a cyano group.

In formula (I) $R_0$ represents a hydrogen atom or a substituent and $R_1$ and $R_3$ each represents a substituent. Examples of the substituent include a halogen atom (e.g., chlorine, bromine), an aliphatic group preferably having from 1 to 36 carbon atoms, an aromatic group preferably having 6 to 36 carbon atoms (e.g., phenyl, naphthyl), a heterocyclic group (e.g., 3-pyridyl, 2-furyl, 2-thienyl, 2-pyridyl, 2-benzo-thiazolyl), an alkoxy group (e.g., methoxy, ethoxy, 2-methoxyethoxy, 2-dodecyloxyethoxy, 2-methanesulfonylethoxy), an aryloxy group (e.g., phenoxy, 2-methylphenoxy, 4-tert-butylphenoxy, 2,4-di-tertaminophenoxy, 2-chlorophenoxy, 4-cyanophenoxy), a heterocyclic oxy group (e.g., 2-benz-imidazolyloxy), an aliphatic or aromatic thio group (e.g., methylthio, ethylthio, octylthio, tetradecylthio, 2-phenoxyethylthio, 3-phenoxypropylthio, 3-(4-tert-butylphenoxy)propylthio, phenylthio, 2-butoxy-5-tert-octylphenylthio, 3-pentadecylphenylthio, 2-carboxyphenylthio, 4-tetradecaneamidophenylthio, 2-benzothiozolylthio), an acyloxy group (e.g., acetoxy, hexadecanoyloxy), a carbamoyloxy group (e.g., N-ethylcarbamoyloxy), a sulfonyloxy group (e.g., dodecyl-sulfonyloxy), an acylamino group (e.g., acetamido, benzamido, tetradecanamido, $\alpha$-(2,4-tert-amylphenoxyacetamido), $\alpha$-[4-(4-hydroxyphenylsulfonyl)-phenoxy)]decanamido, isopentadecanamido), an anilino group (e.g., phenylamino, 2-chloroanilino, 2-chloro-5-tetradecanamidanilino, N-acetylanilino, 2-chloro-5-[$\alpha$-2-tertbutyl-4-hydroxyphenoxy)dodecanamido]anilino), a ureido group (e.g., phenylureido, dimethylureido), a sulfamoylamino group (e.g., N,N-dipropylsulfamoylamino, N-methyl-N-decylsulfamoylamino), an alkenyloxy group (e.g., 2-propenyloxy), an amino group (e.g., butylamino, dimethylamino), an aliphatic, aromatic or heterocyclic acyl group (e.g., acetyl, benzoyl, 2,4-di-tert-aminophenoxyacetyl), an aliphatic, aromatic or heterocyclic sulfonyl group (e.g., methanesulfonyl, octanesulfonyl, benzenesulfonyl, toluenesulfonyl), a sulfinyl group (e.g., octanesulfinyl, dodecylsulfinyl, phenylsulfinyl), an aliphatic, aromatic or heterocyclic oxycarbonyl group (e.g., methoxycarbonyl, butoxycarbonyl, dodecylcarbonyl, octadecylcarbonyl, phenyloxycarbonyl, 2-pentadecyloxycarbonyl), an aliphatic, aromatic or heterocyclic oxycarbonylamino group (e.g., methoxycarbonylamino, tetradecyloxycarbonylamino, phenoxycarbonylamino, 2,4-di-tert-butylphenoxycarbonylamino), a sulfonamido group (e.g., methanesulfonamido, hexadecanesulfonamido, benzenesulfonamido, p-toluenesulfonamido, octadecanesulfonamido, 2-methoxy-5-tert-butylbenzenesulfonamido), a carbamoyl group (e.g., N-ethylcarbamoyl, N,N-dibutylcarbamoyl, N-(2-dodecyloxyethyl)carbamoyl, N-methyl-N-dodecylcarbamoyl, N-[3-(2,4-di-tert-aminophenoxy)-propyl]carbamoyl), a sulfamoyl group (e.g., N-(2-dodecyloxyethyl)sulfamoyl, N-ethyl-N-dodecylsulfamoyl, N,N-diethylsulfamoyl), a sulfamido group (e.g., dipropylsulfamoylamino), an imido group (e.g., succinimido, hydantoinyl), a hydroxyl group, a cyano group, a carboxyl group, a nitro group and a sulfo group.

In formula (I) $R_1$ represents a substituent having a Hammett's $\sigma_p$ value of preferably not less than 0.10, more preferably not less than 0.35. $R_3$ represents a substituent having a Hammett's $\sigma_p$ value of preferably not less than 0.10, more preferably not less than 0.35. The substituents having a Hammett's $\sigma_p$ value of not less than 0.10 or not less than 0.35 are the same as those described for $R_2$.

In formula (I), X represents a hydrogen atom or a group releasable on reaction between the coupler of formula (I) and an oxidation product of an aromatic primary amine derivative (hereinafter simply referred to as a releasable group).

The releasable group as represented by X includes a halogen atom, an aromatic azo group, a group which is bonded to the coupling position of formula (I) via its oxygen, nitrogen, sulfur or carbon atom (e.g., an aliphatic group, an aromatic group, a heterocyclic group, an aliphatic, aromatic or heterocyclic sulfonyl group, or an aliphatic, aromatic or heterocyclic carbonyl group), and a heterocyclic group which is bonded to the coupling position of formula (I) via its nitrogen atom. The aliphatic, aromatic or heterocyclic groups contained in these releasable groups may be substituted with one or more of the substituents allowed for $R_0$, which may be the same or different and which may further be substituted with the substituents allowed for $R_0$.

Specific examples of the releasable group include a halogen atom (e.g., fluorine, chlorine, bromine), an alkoxy group (e.g., ethoxy, dodecyloxy, methoxyethylcarbamoylmethoxy, carboxypropyloxy, methanesulfonylethoxy), an aryloxy group (e.g., 4-chlorophenoxy, 4-methoxyphenoxy, 4-carboxyphenoxy), an acyloxy group (e.g., acetoxy, tetradecanoyloxy, benzoyloxy), an aliphatic or aromatic sulfonyloxy group (e.g., methanesulfonyloxy, toluenesulfonyloxy), an acylamino group (e.g., dichloroacetylamino, heptafluorobutyrylamino), an aliphatic or aromatic sulfonamido group (e.g., methanesulfonamido, p-toluenesulfonamido), an alkoxycarbonyloxy group (e.g., ethoxycarbonyloxy, benzyloxycarbonyloxy), an aryloxycarbonyloxy group (e.g., phenoxycarbonyloxy), an aliphatic, aromatic or heterocyclic thio group (e.g., ethylthio, 2-carboxyethylthio, phenylthio, tetrazolylthio), a carbamoylamino group (e.g., N-methylcarbamoylamino, N-phenylcarbamoylamino), a 5- or 6-membered nitrogen-containing heterocyclic group (e.g., imidazolyl, pyrazolyl, triazolyl, tetrazolyl, 1,2-dihydro-2-oxo-1-pyridyl), an imido group (e.g., succinimido, hydantoinyl), and an aromatic azo group (e.g., phenylazo), each of which may be substituted with the substituent(s) allowed for $R_0$. Couplers having a releasable group bonded via a carbon atom include bis-form couplers which are obtained by condensation of a 4-equivalent coupler by an aldehyde or a ketone. The releasable groups may contain a photographically useful group, such as a residue of a development inhibitor or a development accelerator.

The couplers represented by formula (I) are capable of forming a cyan dye whose absorption maximum is in a wavelength region of from 580 to 710 nm on coupling with an oxidation product of a primary amine developing agent.

The couplers represented by formula (I) embrace those represented by their equilibrium structures (IA) and (IB):

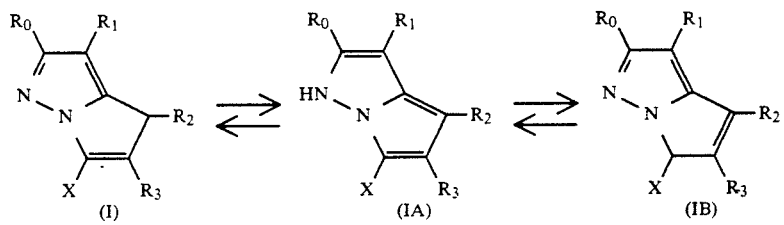

Specific examples of the couplers according to the present invention are shown below for illustrative purposes only but the invention is not limited to these examples.

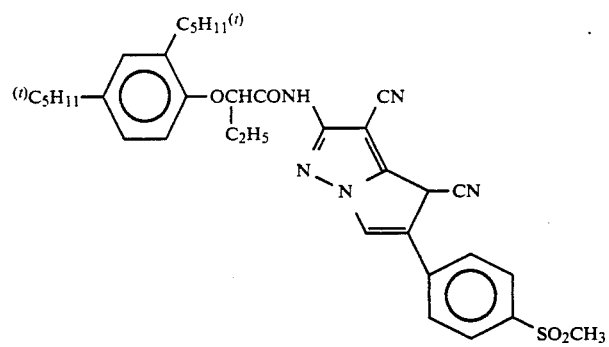

(1)

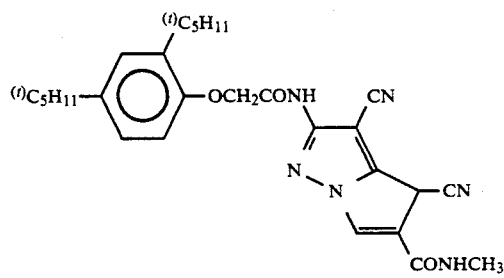

(2)

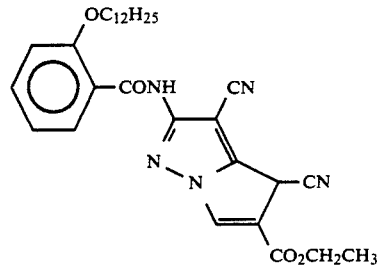

(3)

-continued
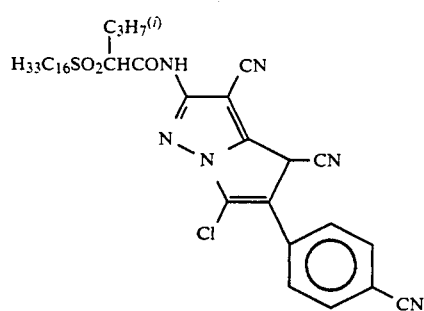
(4)
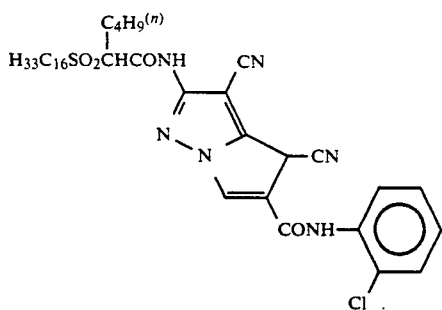
(5)
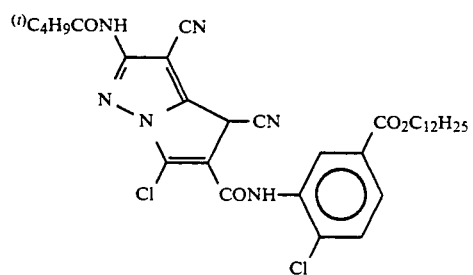
(6)
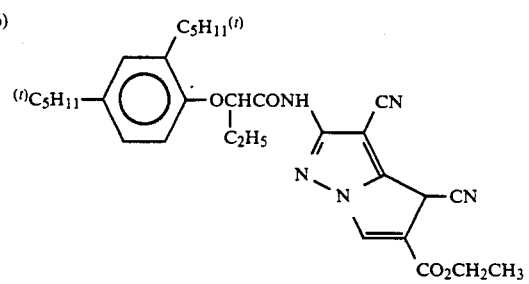
(7)
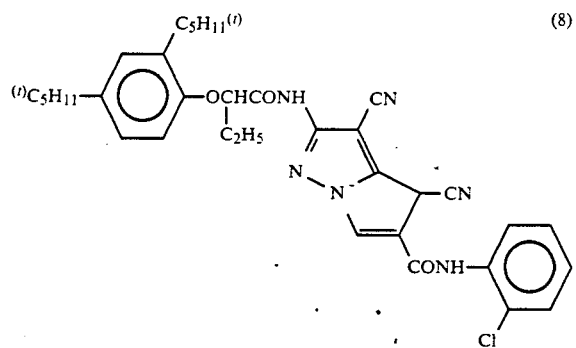
(8)
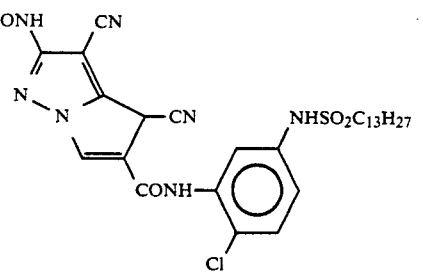
(9)
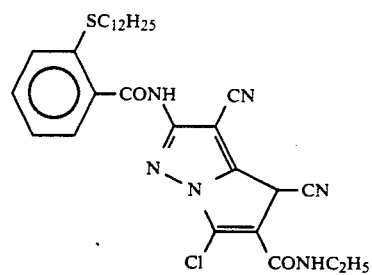
(10)
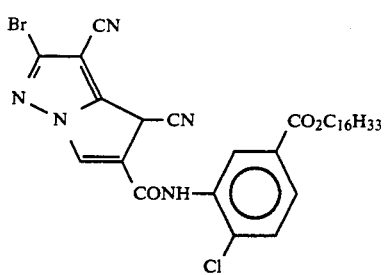
(11)
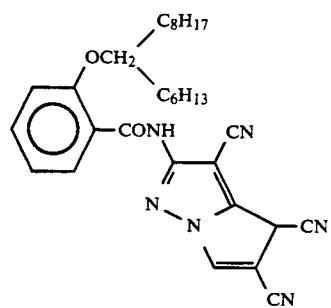
(12)
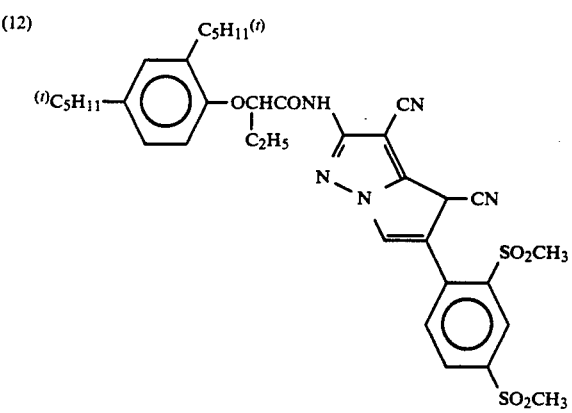
(13)

-continued
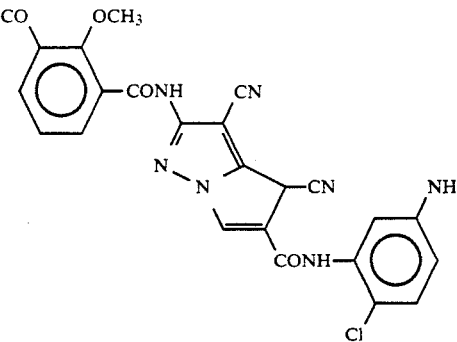 (14)
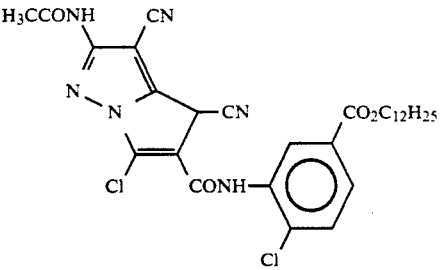 (15)
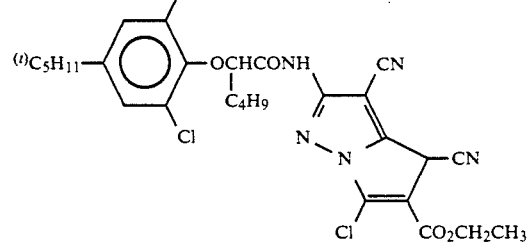 (16)
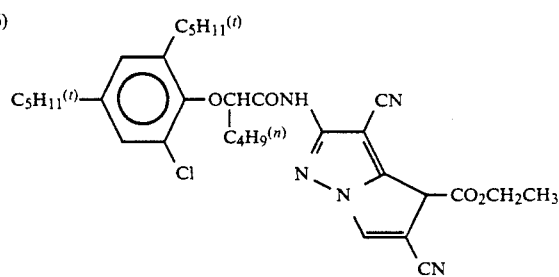 (17)
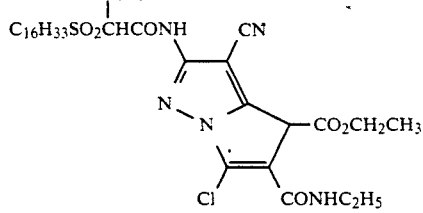 (18)
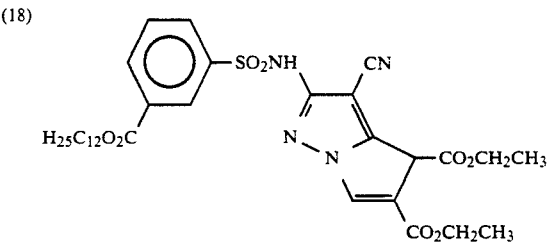 (19)
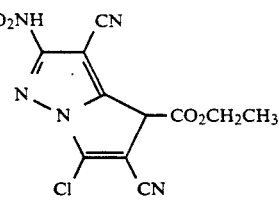 (20)
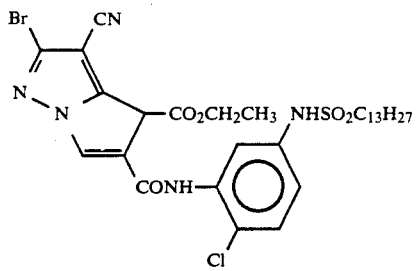 (21)
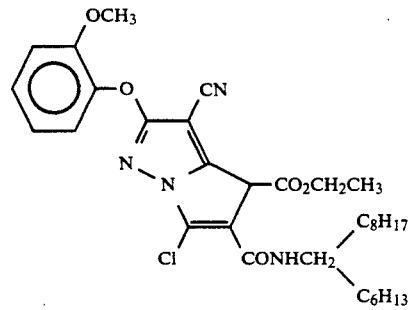 (22)
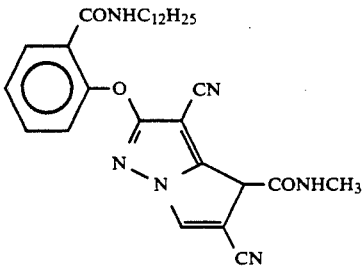 (23)

-continued
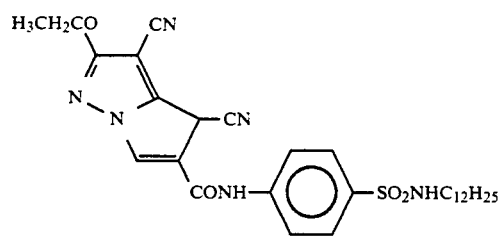
(24)
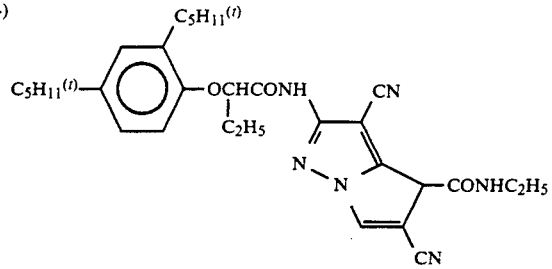
(25)
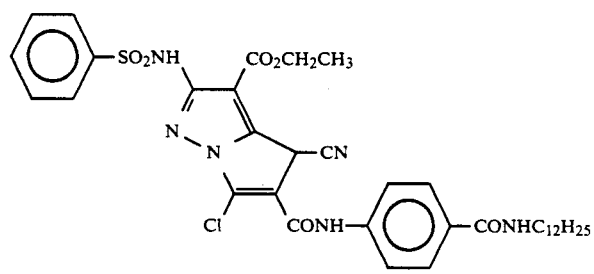
(26)
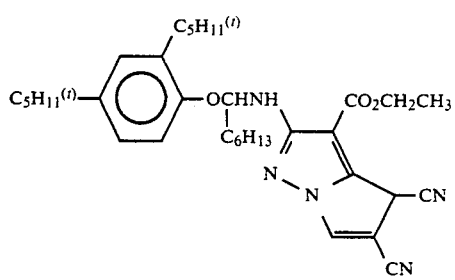
(27)
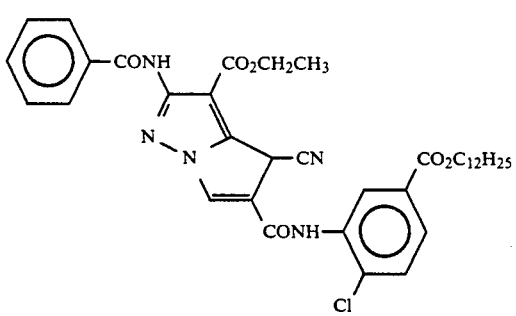
(28)
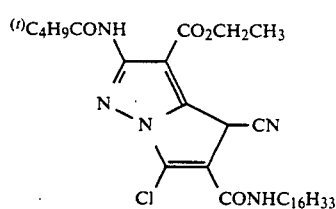
(29)
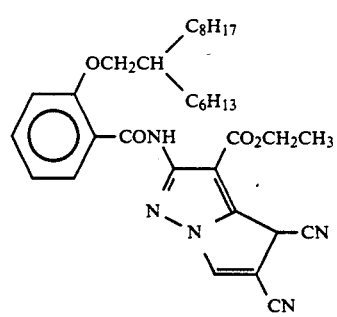
(30)
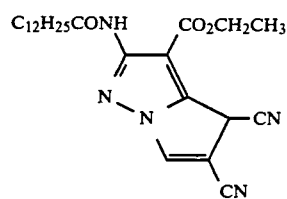
(31)
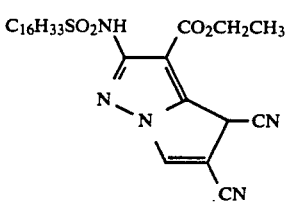
(32)
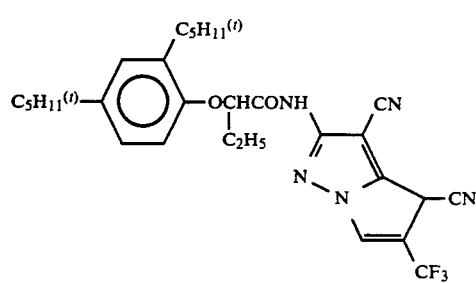
(33)
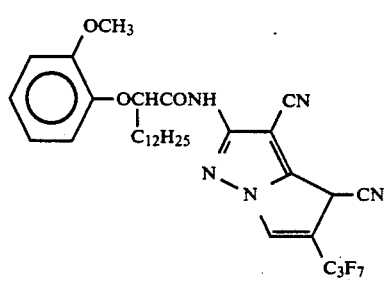
(34)

-continued
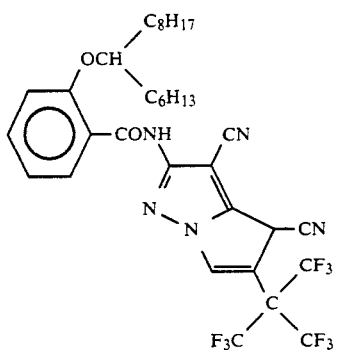 (35)
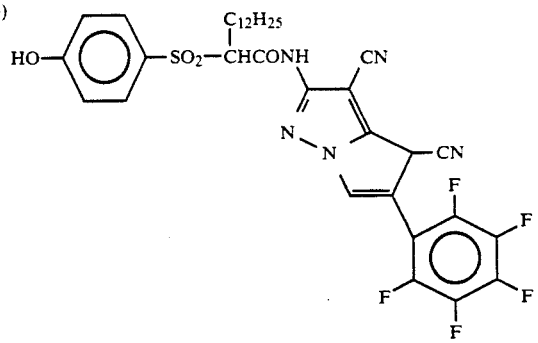 (36)
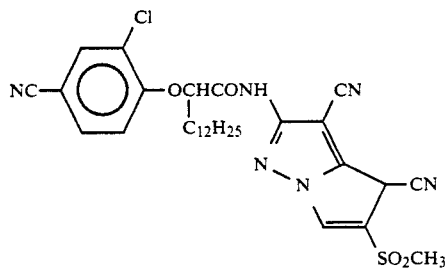 (37)
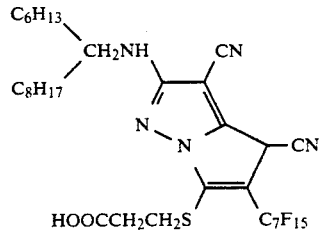 (38)
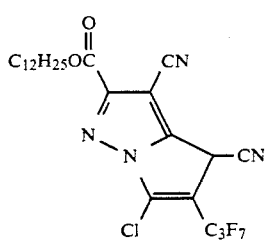 (39)
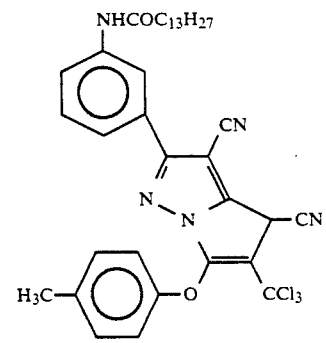 (40)
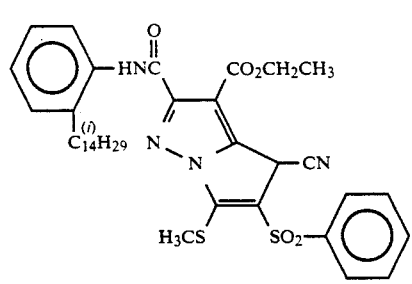 (41)
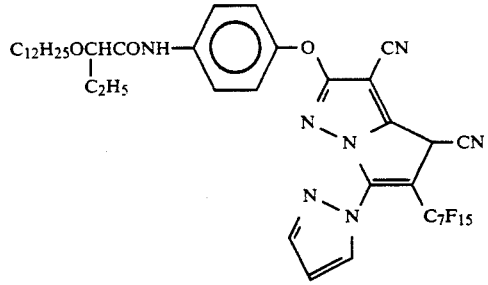 (42)
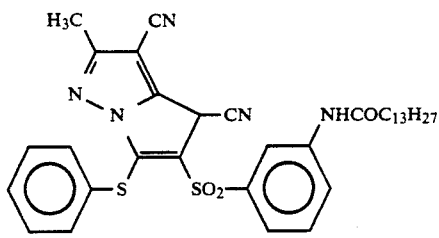 (43)
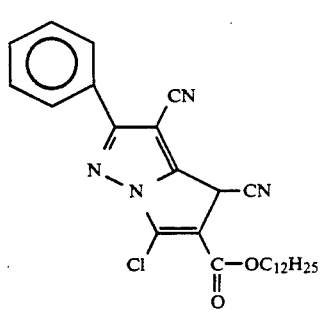 (44)

-continued
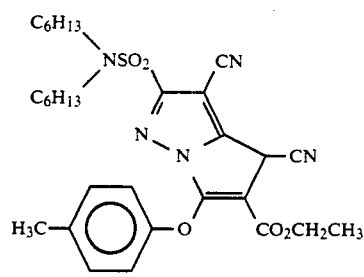 (45)
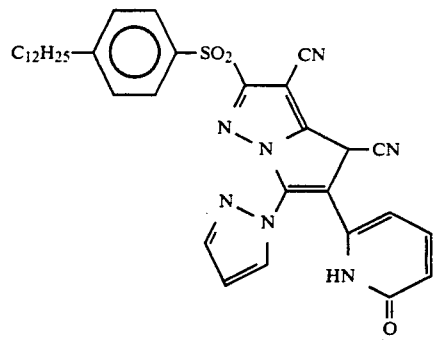 (46)
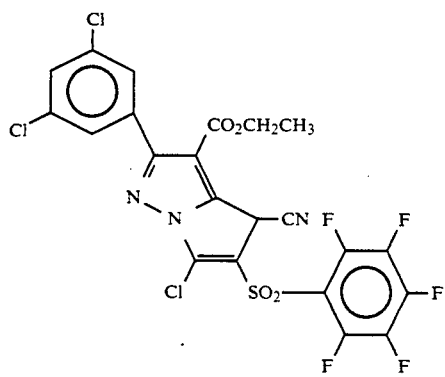 (47)
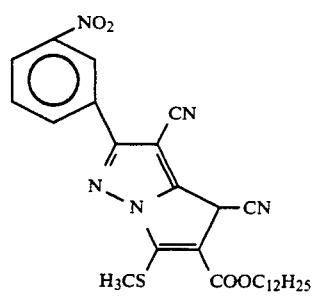 (48)
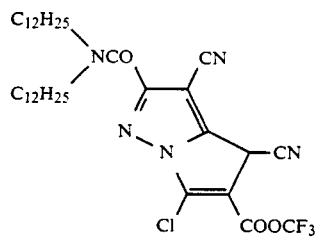 (49)
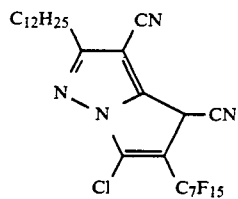 (50)
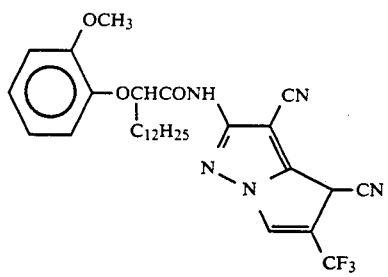 (51)
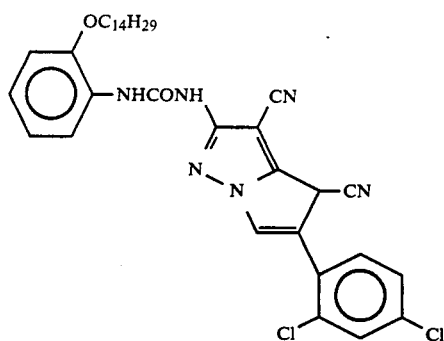 (52)
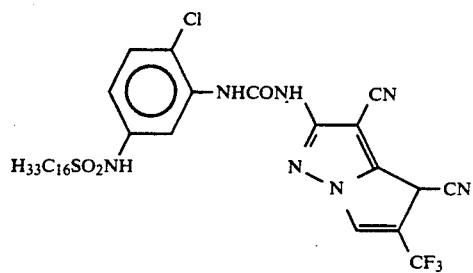 (53)
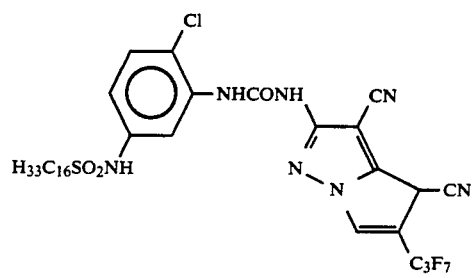 (54)

-continued
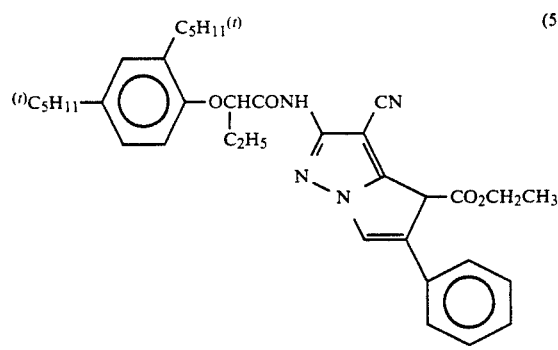 (55)
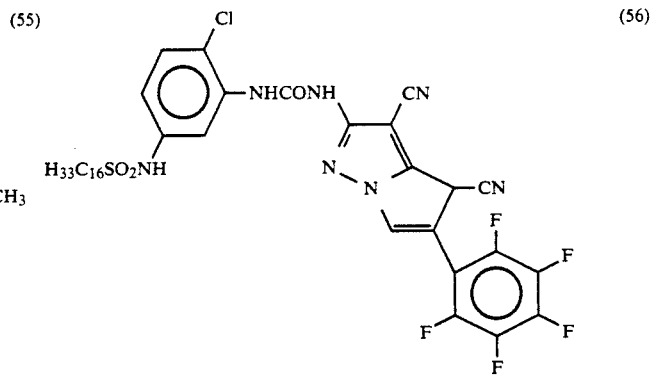 (56)
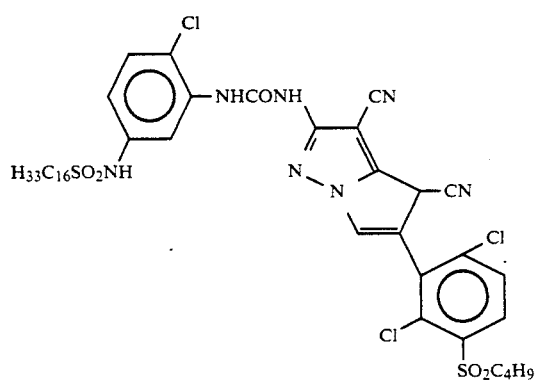 (57)
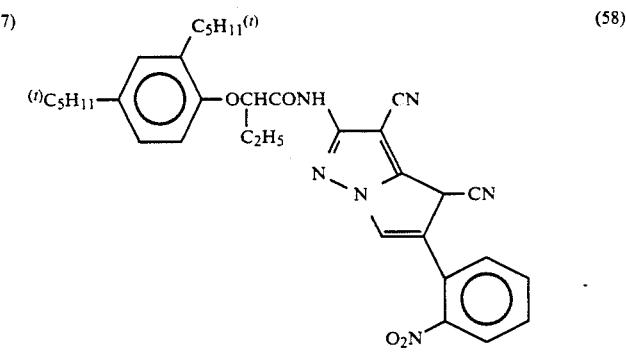 (58)
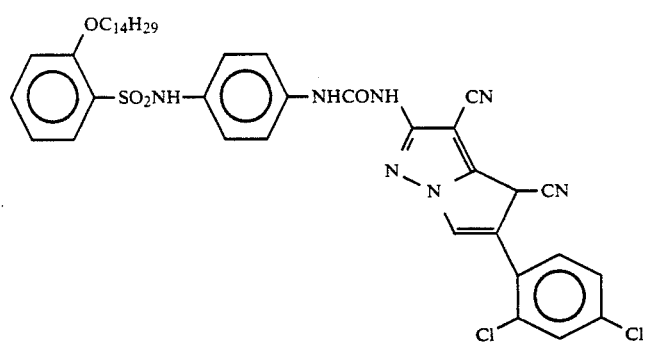 (59)
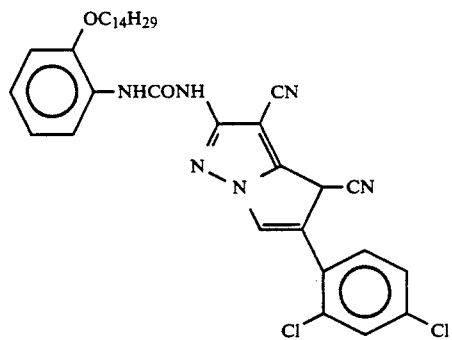 (60)

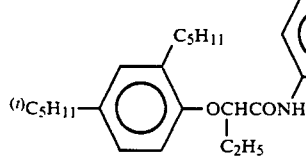
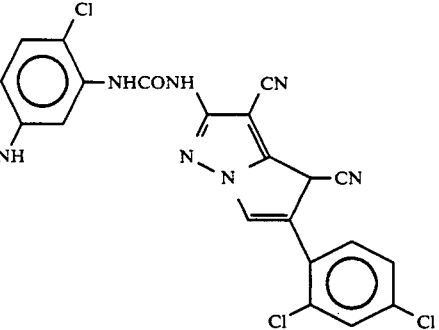 (61)
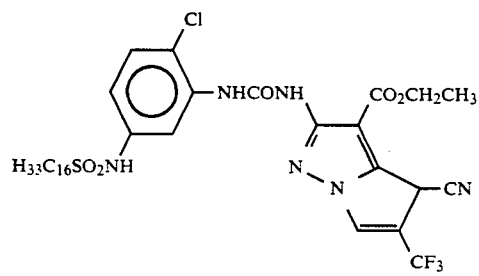 (62)
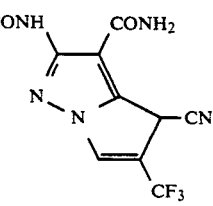 (63)
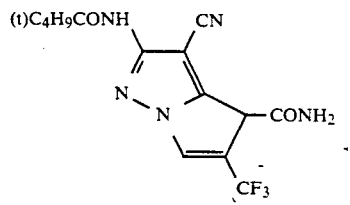 (64)
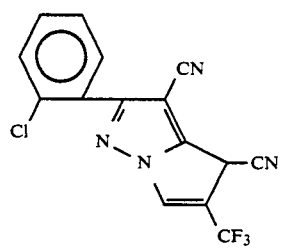 (65)
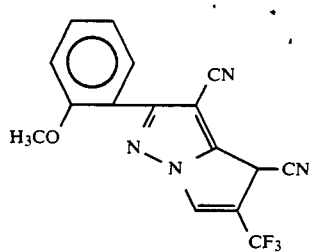 (66)
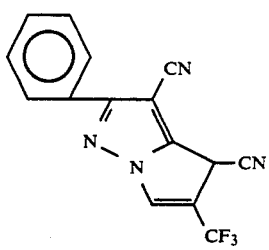 (67)
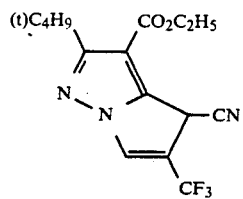 (68)
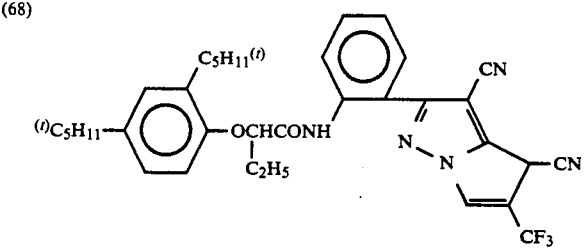 (69)
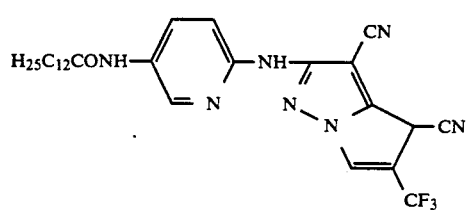 (70)
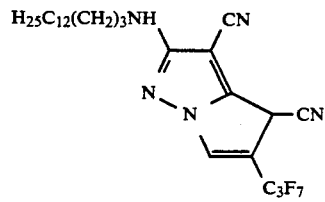 (71)

-continued
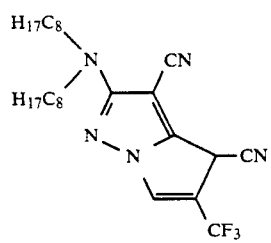 (72)
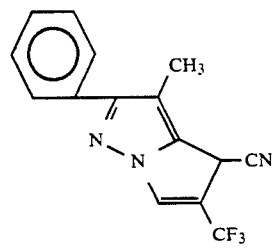 (73)
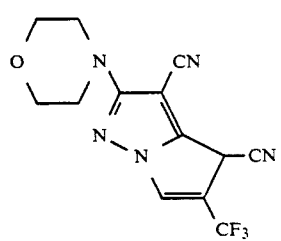 (74)
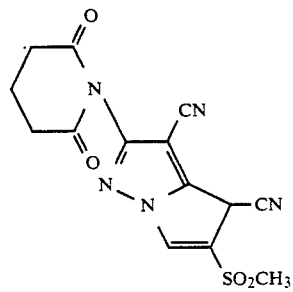 (75)
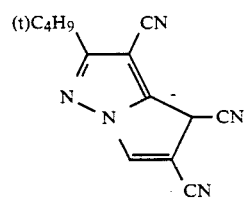 (76)
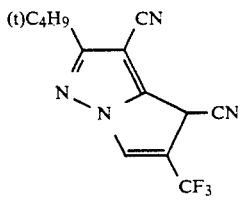 (77)
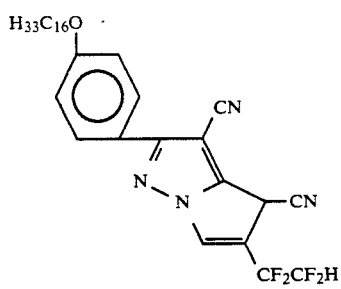 (78)
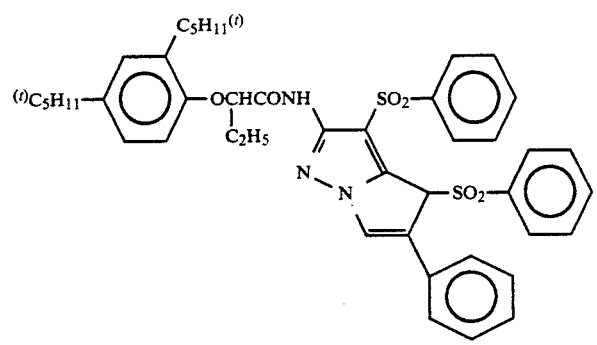 (79)

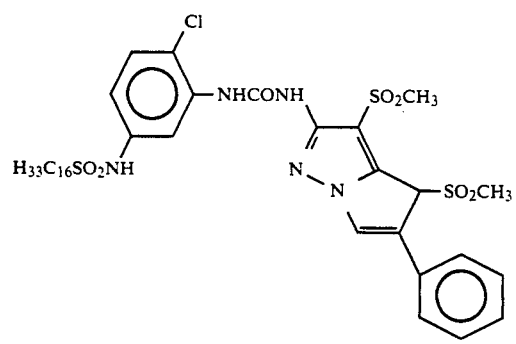
(80)

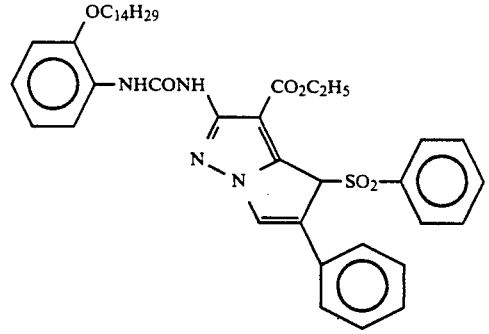
(81)

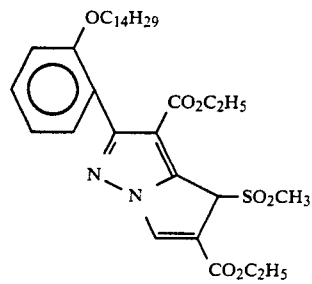
(82)

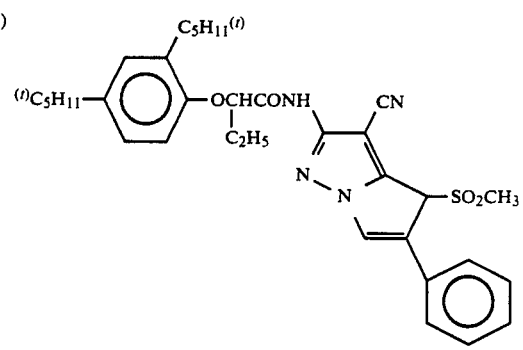
(83)

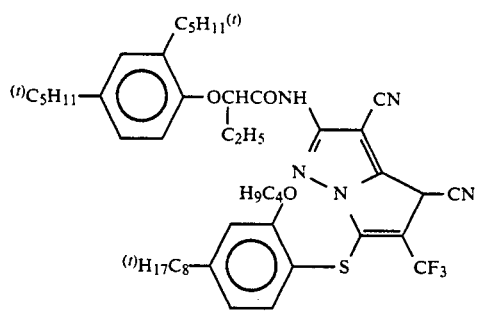
(84)

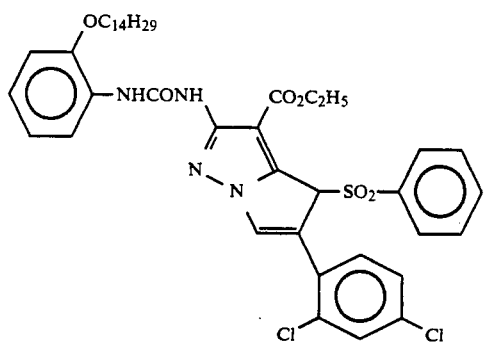
(85)

The compounds of formula (I) can be synthesized by known processes, by example, by the processes disclosed in *J. Amer. Chem. Soc.*, No. 81, p. 2452 (1959), ibid., No. 81, p. 2456 (1959), and *Heterocycles.*, No. 27, p. 2301 (1988), and by the literature references cited therein, or by analogous processes. Starting compounds, intermediate compounds and so on which can be used in the synthesis are also prepared by or with reference to the processes disclosed.

Synthesis examples of the compounds of formula (I) are described below.

SYNTHESIS EXAMPLE 1

Synthesis of Compound (1)

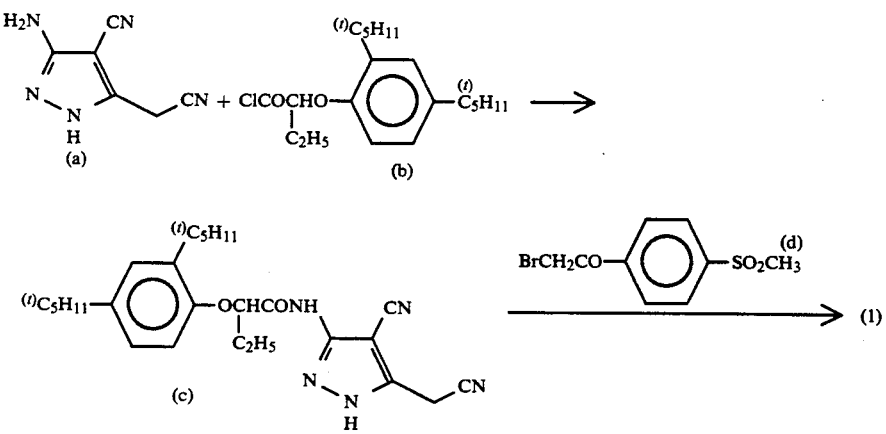

In 500 ml of acetonitrile were dissolved 73.8 g of compound (a) and 170.0 g of compound (b), and 147 ml of triethylamine were added to the solution, followed by heating at reflux for 3 hours. After the reaction, 1 l of ethyl acetate was added to the reaction mixture, and the mixture was washed with water. The ethyl acetate layer was dried and freed of the solvent by distillation, and obtain 2.2 g of the titled compound (33) having a melting point of 125° C.

SYNTHESIS EXAMPLE 4

Synthesis of Compound (52)

Compound (52) was synthesized through the following reaction scheme:

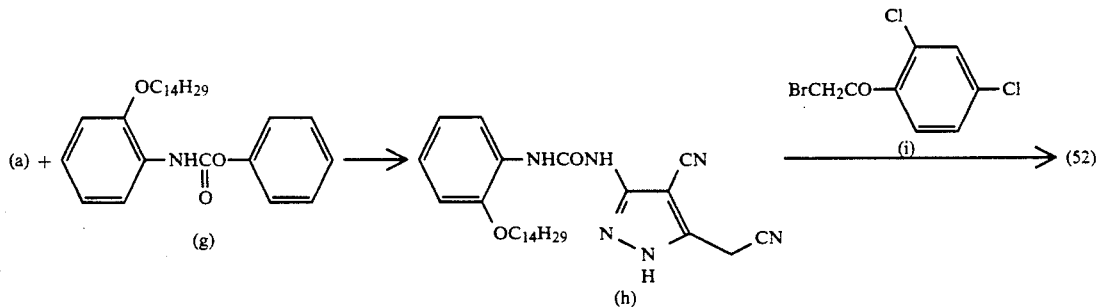

the residue was recrystallized from hexane to obtain 158 g of intermediate compound (c).

In 42 ml of acetonitrile were dissolved 7.3 g of compound (c) and 5.0 g of compound (d), and 7.0 ml of a 28% methanol solution of sodium methylate were added thereto. The mixture was allowed to react at room temperature for 1 hour, 50 ml of ethyl acetate was added thereto, and the mixture was washed with water. The ethyl acetate layer was dried and freed of the solvent by distillation under reduced pressure. The residue was purified by column chromatography to obtain 458 mg of the titled compound (1) having a melting point of 204° to 205° C.

SYNTHESIS EXAMPLE 2

Synthesis of Compound (7)

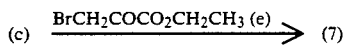

In 20 ml of dimethylformamide were dissolved 1.89 g of compound (c) and 3.90 g of compound (e), and 1.35 g of (t)-BuOK was added thereto, followed by allowing the mixture to react at room temperature for 8 hours. To the reaction mixture was added 50 ml of ethyl acetate, and the mixture was washed with water. The ethyl acetate layer was dried and freed of the solvent by distillation under reduced pressure. The residue was purified by column chromatography to obtain the titled compound (7) having a melting point of 220° C.

SYNTHESIS EXAMPLE 3

Synthesis of Compound (33)

In 100 ml of acetonitrile was dissolved 9.0 g of compound (c), and 8.5 g of a 28% methanol solution of sodium methylate was added thereto, followed by slowly adding dropwise 4.2 g of compound (f) at room temperature. After 20 hours, 200 ml of ethyl acetate was added to the mixture, which was then washed with water. The ethyl acetate layer was dried and then freed of the solvent by distillation under reduced pressure. The residue was purified by column chromatography to In 150 ml of dimethylformamide were dissolved 10.0 g of compound (a) and 30.4 g of compound (g), and 22.8 g of 1.8-diazobicyclo[5,4,0]undecane (DBU), followed by allowing the mixture to react at 50° C. for 10 minutes. After completion of the reaction 300 ml of ethyl acetate was added to the reaction mixture, which was then washed with water. The ethyl acetate layer was dried and freed of the solvent by distillation under reduced pressure, and the residue was recrystallized from hexane-ethyl acetate to obtain 26.0 g of intermediate compound (h).

In 300 ml of dimethylactamide were dissolved 22.5 g of the resulting component (h) and 21.1 g of compound (i), and 15.8 g of DBU was added thereto at a reaction temperature of 45° C. After the reaction at 70° C. for 30 minutes, 500 ml of ethyl acetate was added to the reaction mixture, which was then washed with water. The ethyl acetate layer was dried and freed of the solvent by distillation under reduced pressure, and the residue was purified by column chromatography to obtain 9.9 g of the titled compound (52) having a melting point of 148° C.

SYNTHESIS EXAMPLE 5

Synthesis of Compound (53)

Compound (53) was synthesized through the following reaction scheme:

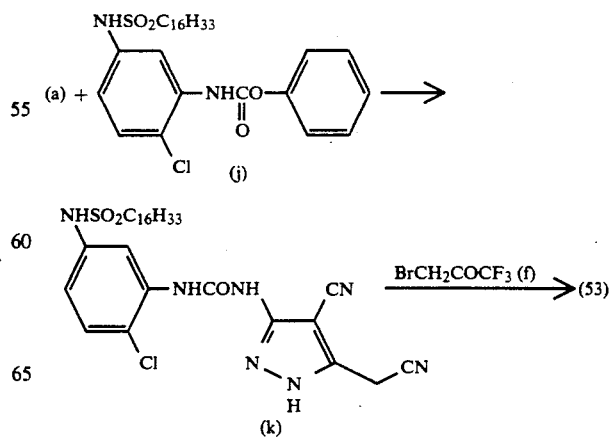

In 1 l of dimethylacetamide were dissolved 118 g of compound (a) and 440 g of compound (j), and 240 ml of DBU was added dropwise to the mixture at room temperature. The mixture was allowed to react under stirring for 1.5 hours. After completion of the reaction, 1.5 l of ethyl acetate, 180 ml of a 36% aqueous hydrochloric acid and 1.5 l of ice-cold water were added to the reaction mixture to effect extraction. The ethyl acetate layer was dried over magnesium sulfate, and then freed of the solvent by distillation under reduced pressure. The residue was recrystallized from acetonitrile to obtain 320 g of compound (k).

In 40 ml of dimethylformamide were dissolved 6.0 g of the resulting compound (k) and 2.1 g of compound (f), and 4.5 ml of a 28% methanol solution of sodium methylate was added dropwise to the solution at room temperature. After completion of the reaction, 100 ml of ethyl acetate was added to the reaction mixture, which was then washed with water. The ethyl acetate layer was dried and freed of the solvent by distillation under reduced pressure, and the residue was purified by column chromatography to obtain 1.4 g of the titled compound (53) having a melting point of 118° C..

Other couplers can also be synthesized in a similar manner.

In order to examine a basic hue of the cyan dye obtained from the couplers of the present invention, dyes (100)-(105) shown below were synthesized from compounds (33), (51) and (53), of the present invention and comparative couplers (R-1), (R-2) and (R-3), respectively.

Comparative Coupler (R-1)

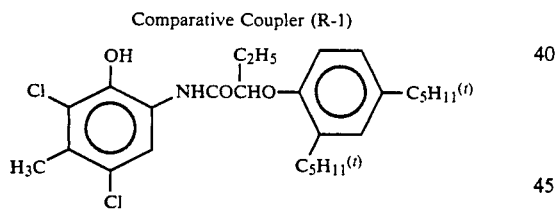

Comparative Coupler (R-2)

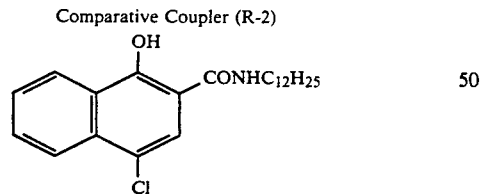

Comparative Coupler (R-3)
(a coupler included in U.S. Pat. No. 4,728,598)

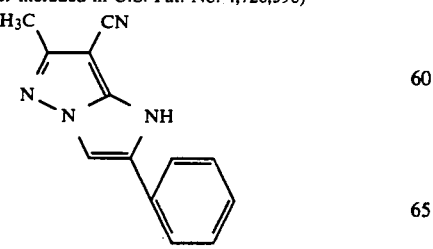

Compound (100):

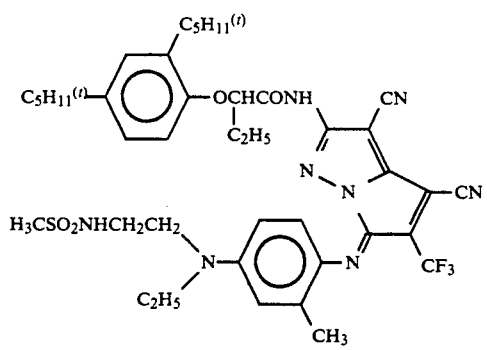

Compound (101):

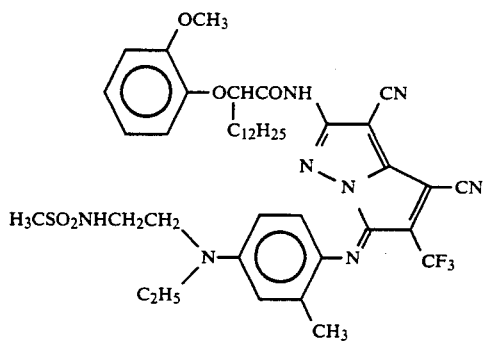

Compound (102):

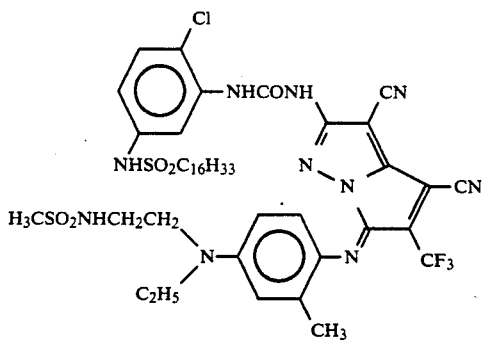

Comparative Compound (103):

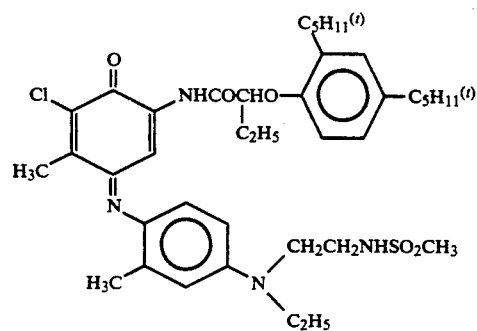

Comparative Compound (104):

-continued

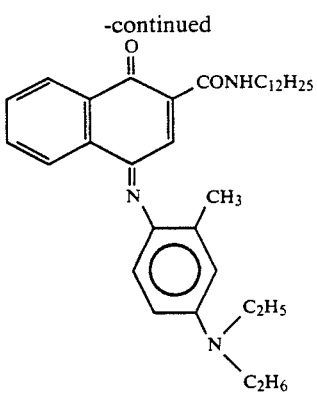

Comparative Compound (105):

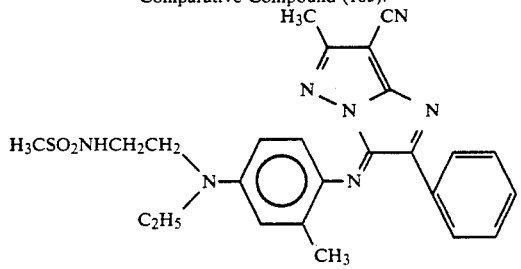

Compound (100) was synthesized through the following reaction scheme:

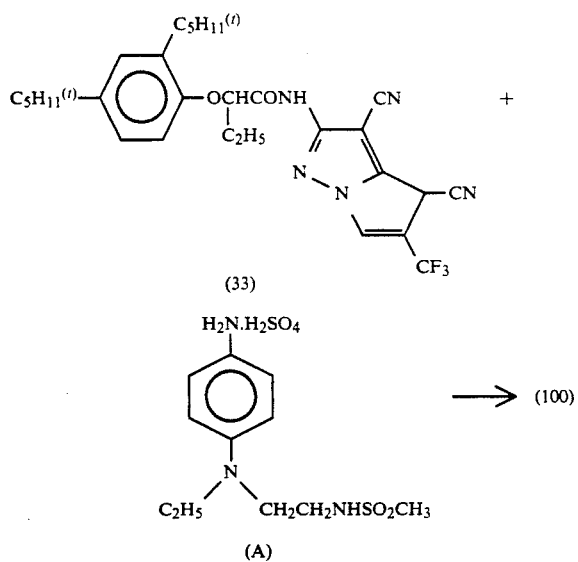

To a solution of 449 mg of compound (33) in 5 ml of ethanol and 3 ml of ethyl acetate was added a solution of 652 mg of sodium carbonate in 5 ml of water. To the mixture were further added 644 mg of compound (A) and 674 mg of ammonium persulfate, followed by stirring for 30 minutes. The precipitated crystal was thoroughly washed with water and collected by filtration to obtain 550 mg of compound (100) having a melting point of 179° to 180° C.

Compounds (101) and (105) were also synthesized similarly.

The maximum absorption wavelength in ethyl acetate and the molecular extinction coefficient of the thus synthesized dyes and comparative dyes (100) to (105) are shown in Table 1 below. The relative visible light absorption spectrums of compounds (100), (102), (103) and (105) are shown in FIG. 1 normalizing the maximum absorption intensity of compound (100) to be 1.

TABLE 1

| Dye | Maximum Absorption Wavelength (nm) | Molecular Extinction Coefficient ($l \cdot mol^{-1} \cdot cm^{-1}$) |
|---|---|---|
| (100) | 637.2 | $7.34 \times 10^4$ |
| (101) | 635.8 | $7.40 \times 10^4$ |
| (102) | 647.9 | $7.45 \times 10^4$ |
| Comparative Compound (103) | 644.3 | $2.7 \times 10^4$ |
| Comparative Compound (104) | 661.0 | $2.6 \times 10^4$ |
| Comparative Compound (105) | 591.3 | $3.1 \times 10^4$ |

As can be seen from FIG. 1, the dyes of the present invention reveal much sharper spectrums than comparative compounds and, in addition, shows no side absorption in the blue light region between 400 nm and 500 nm, thus providing a very bright cyan hue.

Therefore, dyes produced from the couplers of the present invention have higher molecular extinction coefficients than the dyes produced from the comparative couplers. This means that a desired optical density can be obtained with the couplers of the present invention and they can be used in a much reduced amount as compared with the conventional couplers.

The dye forming coupler of formula (I) of the present invention produces a dye on oxidative coupling in the presence of a developing agent, an alkali, and an oxidizing agent (e.g., persulfates, silver nitrate, nitrous acid or salts thereof) and, if desired, an organic solvent. The coupler of the present invention wherein X in formula (I) is a hydrogen atom also produces a dye on condensation in the presence of a p-nitrosoaniline compound and an alkali or acetic anhydride. The thus produced cyan dye is widely useful as a filter, a paint, an ink, and a dye for image or information recording or printing.

Silver halide light-sensitive materials to which the coupler of formula (I) is applied comprises a support having thereon at least one hydrophilic colloidal layer containing the coupler of formula (I). General color light-sensitive materials comprise a support having thereon at least one layer of each of a blue-sensitive silver halide emulsion layer, a green-sensitive silver halide emulsion layer, and a red-sensitive silver halide emulsion layer in this order or different orders. The coupler of the present invention is preferably incorporated into a red-sensitive silver halide emulsion layer. An infrared-sensitive silver halide emulsion layer may be used in place of at least one of the above-described light-sensitive emulsion layers. These light-sensitive emulsion layers each contains a silver halide emulsion having sensitivity to the respective wavelength region and a color coupler capable of forming a dye of a color complementary to the light to which it is sensitive to thereby accomplish color reproduction (subtractive color process). The light-sensitive material may also have a structure in which the light-sensitive layers and the developed hue of the couplers do not have the above-described relationship. The dye forming coupler of the present invention in which any one of $R_0$, $R_1$, $R_2$ and X in formula (I) have a total number of carbon atoms of preferably 10 or more, is incorporated into the light-sensitive material.

The coupler of the present invention is used in the light-sensitive material in an amount of from $1 \times 10^{-5}$ to $1 \times 10^{-2}$ mol, and preferably from $5 \times 10^{-5}$ to $5 \times 10^{-3}$ mol, per m$^2$ of the light-sensitive material. When the coupler of the present invention is soluble in an alkali aqueous solution, the light-sensitive material may be a coupler-in-developer-type color film which forms a dye image on development with a color developing solution comprising an alkali aqueous solution having dissolved therein the coupler of the present invention together with a developing agent and other necessary additives. In this case, the coupler is used in an amount of from 0.0005° to 0.05 mol, and preferably from 0.005 to 0.02 mol, per liter of a color developing solution.

The coupler of the present invention can be introduced into a light-sensitive material by various known dispersion methods. An oil-in-water dispersion method, in which the coupler is dissolved in a high-boiling organic solvent (oil) (and, if necessary, a low-boiling organic solvent), dispersing the solution in a gelatin aqueous solution, and adding the dispersion to a silver halide emulsion, is preferred.

High-boiling organic solvents which are useful in the oil-in-water dispersion method are described, for example, in U.S. Pat. No. 2,322,027. With respect to a latex dispersion method, one of polymer dispersion methods, the steps involved, the effects, and specific examples of useful loadable lattices are described in U.S. Pat. No. 4,199,363 and West German Patent (OLS) Nos. 2,541,274 and 2,541,230, JP-B-53-41091, and EP Publication No. 029104. With respect to a dispersion method using an organic solvent-soluble polymer, reference can be made in PCT No. WP88/00723.

Specific examples of high-boiling organic solvents which can be used in the oil-in-water dispersion method are phthalic esters (e.g., dibutyl phthalate, dioctyl phthalate, dicyclohexyl phthalate, di-2-ethylhexyl phthalate, decyl phthalate, bis(2,4-di-t-amylphenyl) isophthalate, bis(1,1-diethylpropyl) phthalate), phosphoric or phosphonic esters (e.g., diphenyl phosphate, triphenyl phosphate, tricresyl phosphate, 2-ethylhexyldiphenyl phosphate, dioctylbutyl phosphate, tricyclohexyl phosphate, tri-2-ethylhexyl phosphate, tridodecyl phosphate, di-2-ethylhexylphenyl phosphonate), benzoic acid esters (e.g., 2-ethylhexyl benzoate, 2,4-dichlorobenzoate, dodecyl benzoate, 2-ethylhexyl p-hydroxybenzoate), amides (e.g., N,N-diethyldodecanamide, N,N-diethyllaurylamide), alcohols or phenols (e.g., isostearyl alcohol, 2,4-di-t-amylphenol), aliphatic carboxylic acid esters (e.g., dibutoxyethyl succinate, di-2-ethylhexyl succinate, 2-hexyldecyl tetradecanoate, tributyl citrate, diethyl azelate, isostearyl lactate, trioctyl citrate), aniline derivatives (e.g., N,N-dibutyl-2-butoxy-5-t-octylaniline), and chlorinated paraffins (paraffins having a chlorine content of from 10 to 80%), trimesic esters (e.g., tributyl trimesate), dodecylbenzene, diisopropylnaphthalene, phenols (e.g., 2,4-di-t-amylphenol, 4-dodecyloxyphenol, 4-dodecyloxycarbonylphenol, 4-(4-dodecyloxyphenylsulfonyl)phenol), carboxylic acids (e.g., 2-(2,4-di-t-amylphenoxybutyric acid, 2-ethoxyoctanedecanoic acid), and alkylphosphates (e.g., di-(2-ethylhexyl) phosphate, diphenyl phosphate). Organic solvents having a boiling point of from 30° C. to about 160° C. may be used in combination as an auxiliary solvent. Typical examples of such an auxiliary solvent are ethyl acetate, butyl acetate, ethyl propionate, methyl ethyl ketone, cyclohexanone, 2-ethoxyethyl acetate, and dimethylformamide.

Of these organic solvents, preferred for the couplers of the present invention are polar high-boiling organic solvents, and particularly amides. Examples of suitable amide solvents in addition to the above-described examples are described in U.S. Pat. Nos. 2,322,027, 4,127,413, and 4,745,049. In particular, high-boiling organic solvents having a specific permittivity of about 6.5 or less, and preferably from 5 to 6.5, as measured at 25° C. at 10 Hz are preferred.

The high-boiling organic solvent is used in an amount of from 0 to 2.0 times, and preferably from 0 to 1.0 time, the weight of the coupler.

The couplers of the present invention are applicable to color papers, color reversal papers, direct positive color light-sensitive materials, color negative films, color positive films, color reversal films, etc. They are preferably applicable to color light-sensitive materials having a reflective support (e.g., color papers, color reversal papers) and color light-sensitive materials forming a positive image (e.g., direct positive color light-sensitive materials, color positive films, color reversal films), and particularly color light-sensitive materials having a reflective support Silver halide emulsions which can be used in the present invention may have any halogen composition, such as silver iodobromide, silver iodochlorobromide, silver bromide, silver chlorobromide, and silver chloride.

While the halogen composition of a silver halide emulsion may be either the same or different among individual grains, use of an emulsion having the same halogen composition among grains makes it easy to obtain grains having uniform properties. The halogen composition may be uniformly distributed throughout the individual grains (homogeneous grains), or the individual grains may have a non-uniformly distributed halogen composition to form a laminate structure comprising a core and a single-layered or multi-layered outer shell or may have a nonlayered portion differing in halogen composition in the inside or on the surface thereof (when such a portion is on the surface, it is fused on the edge, corner or plane of the grain). Either of the latter two types of grains is preferred to the homogeneous grains in order to obtain high sensitivity and also from the standpoint of preventing pressure marks. In these heterogeneous grains, layers or portions differing in halogen composition may have a clear boundary therebetween or may form a mixed crystal to have a vague boundary therebetween. Further, the structure may be so designed as to have a continuously varying halogen composition.

A preferred halogen composition depends on the desired type of light-sensitive materials. For example, a silver chlorobromide emulsion is preferred for use in color papers; a silver iodobromide emulsion having a silver iodide content of from 0.5 to 30 mol % (preferably from 2 to 25 mol %) is preferred in light-sensitive materials for photography, e.g., color negative films and color reversal films; and a silver bromide emulsion or a silver chlorobromide emulsion is preferred in direct positive color light-sensitive materials. In light-sensitive materials suited for rapid processing, an emulsion having a high silver chloride content (hereinafter referred to as a high silver chloride emulsion) is preferably used. Such a high silver chloride emulsion preferably has a silver chloride content of 90 mol % or more, and more preferably 95 mol % or more.

Silver halide grains in the high silver chloride emulsion preferably has a localized silver bromide layer(s) or portion(s) (hereinafter inclusively referred to as a localized phase(s)) in the inside and/or on the surface of the individual grains. The localized phase preferably has a silver bromide content of at least 10 mol %, and more preferably more than 20 mol %. The localized phases may be present in the inside of the grains or on the surface (e.g., edges, corners, or planes) of the grains. One preferred example of such localized phases is an epitaxially grown portion on the corner(s) of grains.

For use in the present invention, a silver chlorobromide or silver chloride emulsion containing substantially no silver iodide is particularly preferred. The terminology "substantially no silver iodide" as used herein means that a silver iodide content is not more than 1 mol %, and preferably not more than 0.2 mol %.

The silver halide grains in the silver halide emulsions have a mean grain size preferably of from 0.1 to 2 μm, and more preferably of from 0.15 to 1.5 μm (the mean grain size is a number average of a diameter of a circle equivalent to a projected area of a grain) with a size distribution having a coefficient of variation (a quotient obtained by dividing a standard deviation by a mean grain size) of not more than 20%, and preferably not more than 15% (so-called monodispersed grains). For the purpose of obtaining a broad latitude, two or more kinds of such monodispersed emulsions may be blended and coated in the same layer or may be separately coated in different layers.

Silver halide grains of the photographic emulsions may have a regular crystal form, such as a cubic form, a tetradecahedral form, and an octahedral form; an irregular crystal form, such as a spherical form and a plate form; or a composite crystal form thereof. Tabular grains can also be used.

The emulsions which can be used in the present invention may be either a surface latent image type which forms a latent image predominantly on the grain surface or an internal latent image type which forms a latent image predominantly in the inside of the grains.

Silver halide photographic emulsions to be used in the present invention can be prepared by the processes described, e.g., in *Research Disclosure*, No. 17643 (Dec., 1978), pp. 22-23, "I. Emulsion Preparation and Types", and ibid., No. 18716 (Nov., 1979), p. 648, P. Glafkides, *Chemic et Phisique Photographique*, Paul Montel (1967), G. F. Duffin, *Photographic Emulsion Chemistry*, Focal Press (1966), and V. L. Zelikman et al., *Making and Coating Photographic Emulsion*, Focal Press (1964).

Monodispersed emulsions described in U.S. Pat. Nos. 3,574,628 and 3,655,394 and British Pat. No. 1,413,748 are preferably used as well.

Tabular grains having an aspect ratio of about 5 or more are also useful. Such tabular grains can be easily prepared by the processes described, for example, in Gutoff, *Photographic Science and Engineering*, Vol. 14, pp. 248-257 (1970), U.S. Pat. Nos. 4,434,226, 4,414,310, 4,433,048, and 4,439,520, and British Patent 2,112,157.

The silver halide grains may be homogeneous grains having a uniform crystal structure throughout the individual grains or heterogeneous grains including those in which the inside and the outer shell have different halogen compositions, those in which the halogen composition differs among layers, and those having fused thereto silver halide of different halogen composition through epitaxy. Silver halide grains fused with compounds other than silver halides, for example, silver rhodanide or lead oxide may also be used. A mixture comprising grains of various crystal forms is employable.

These silver halide emulsions are usually used after physical ripening, chemical ripening, and spectral sensitization.

During grain formation or physical ripening, various polyvalent metal ion impurities may be introduced into silver halide emulsions. Such impurity-donating compounds include salts of cadmium, zinc, lead, copper, thallium, etc., and salts or complexes of the group VIII metals, for example, iron, ruthenium, rhodium, palladium, osmium, iridium, and platinum.

Additives to be used in physical ripening, chemical ripening and spectral sensitization of the silver halide emulsions and other known photographic additives which can be used in the present invention are described in *Research Disclosure* Nos. 17643, 18716, and 30710 supra as tabulated below.

| Additive | RD 17643 | RD 18716 | RD 307105 |
|---|---|---|---|
| 1. Chemical Sensitizer | p. 23 | p. 648, right column (RC) | p. 866 |
| 2. Sensitivity Increasing Agent | | p. 648, right column (RC) | |
| 3. Spectral Sensitizer, Supersensitizer | pp. 23-24 | p. 648, RC to p. 649, RC | pp. 866-868 |
| 4. Brightening Agent | p. 24 | p. 647, RC | p. 868 |
| 5. Antifoggant and Stabilizer | pp. 24-25 | p. 649, RC | pp. 868-870 |
| 6. Light Absorber, Filter Dye, Ultrasonic Absorber | pp. 25-26 | p. 649, RC to p. 650, left column (LC) | p. 873 |
| 7. Stain Inhibitor | p. 25, RC | p. 650, LC to RC | p. 872 |
| 8 Dye Image Stabilizer | p. 25 | p. 650, LC | p. 872 |
| 9. Hardening Agent | p. 26 | p. 651, LC | pp. 874-875 |
| 10. Binder | p. 26 | p. 651, LC | pp. 873-874 |
| 11. Plasticizer, Lubricant | p. 27 | p. 650, RC | p. 876 |
| 12. Coating Aid, Surface Active Agent | pp. 26-27 | p. 650, RC | pp. 875-876 |
| 13. Antistatic Agent | p. 27 | p. 650, RC | pp. 876-877 |
| 14. Matting Agent | | | pp. 878-879 |

In order to prevent photographic performance deterioration due to contact with formaldehyde gas, the light-sensitive material of the present invention preferably contains a compound capable of reacting with formaldehyde to fix it as described in U.S. Pat. Nos. 4,411,987 and 4,435,503.

Various known couplers can be used in the light-sensitive materials of the present invention in combination with the couplers of formula (I). Specific examples of useful couplers are described in patents cited in *Research Disclosure*, No. 17643, supra, VII-C to G and ibid., No. 307105, VII-C to G.

Examples of suitable yellow couplers are described, for example, in U.S. Pat. Nos. 3,933,501, 4,022,620, 4,326,024, 4,401,752, and 4,248,961, JP-B-58-10739, British Patents 1,425,020 and 1,476,760, U.S. Pat. Nos. 3,973,968, 4,314,023, and 4,511,649, and EP 249,473A.

The coupler according to the present invention is preferably used in combination with yellow couplers which produce a dye having its maximum absorption wavelength in the shorter wavelength region and showing a sharply descending absorption in the longer wavelength region exceeding 500 nm. Examples of such yellow couplers are described, for example, in JP-A-63-123047 and JP-A-1-173499.

Examples of suitable magenta couplers include 5-pyrazolone couplers and pyrazoloazole couplers. Examples of particularly preferred magenta couplers are described in U.S. Pat. Nos. 4,310,619 and 4,351,897, European Patent 73,636, U.S. Pat. Nos. 3,061,432 and 3,725,064, *Research Disclosure*, No. 24220 (Jun., 1984), JP-A-60-33552, *Research Disclosure*, No. 24230 (Jun., 1984), JP-A-60-43659, JP-A-61-72238, JP-A-60-35730, JP-A-55-118034, JP-A-60-185951, U.S. Pat. Nos. 4,500,630, 4,540,654, and 4,556,630, and WO 88/04795.

Cyan couplers include phenol couplers and naphthol couplers. Examples of suitable cyan couplers are described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011, and 4,327,173, West German Pat. No. Publication No. 3,329,729, EP 121,365A, EP 249,453A, U.S. Pat. Nos. 3,446,622, 4,333,999, 4,775,616, 4,451,559, 4,427,767, 4,690,889, 4,254,212, and 4,296,199, and JP-A-61-42658.

Examples of suitable colored couplers which can be used for correcting unnecessary absorption of a developed dye are described in *Research Disclosure*, No. 17643, VII-G, U.S. Pat. No. 4,163,670, JP-B-57-39413, U.S. Pat. Nos. 4,004,929 and 4,138,258 and British Patent 1,146,368. Further, couplers capable of releasing a fluorescent dye upon coupling by which unnecessary absorption of a developed dye is corrected are described in U.S. Pat. No. 4,774,181. Couplers having a dye precursor group as a releasable group which is capable of reacting with a developing agent to form a dye as described in U.S. Pat. No. 4,777,120 are preferably used.

Examples of suitable couplers which develop a dye having moderate diffusibility are described in U.S. Pat. No. 4,366,237, British Patent 2,125,570, European Patent 96,570, and West German Patent (OLS) No. 3,234,533.

Typical examples of polymerized dye forming couplers are described in U.S. Pat. Nos. 3,451,820, 4,080,211, 4,367,282, 4,409,320, and 4,576,910, British Patent 2,102,173, and EP 341,188A.

Couplers capable of releasing a photographically useful residue on coupling are also useful. Examples of suitable DIR couplers which release a development inhibitor are described in patents cited in *Research Disclosure*, No. 17643, VII-F, JP-A-57-151944, JP-A-57-154234, JP-A-60-184248, JP-A-63-37346, and U.S. Pat. Nos. 4,248,962 and 4,782,012.

Examples of suitable couplers which imagewise release a nucleating agent or a development accelerator at the time of development are described in British Patents 2,097,140 and 2,131,188, JP-A-59-157638, and JP-A-59-170840.

Other couplers which can be used in the light-sensitive materials of the present invention include competing couplers as described in U.S. Pat. No. 4,130,427; poly-equivalent couplers as described in U.S. Pat. Nos. 4,283,472, 4,338,393, and 4,310,618; couplers capable of releasing a DIR redox compound, a DIR coupler, a DIR coupler-releasing couplers, a DIR coupler-releasing redox compound, or a DIR redox-releasing redox compound as described in JP-A-60-185950 and JP-A-62-24252; couplers capable of releasing a dye which restores its color after release as described in EP 173,302A; couplers capable of releasing a bleaching accelerator as described in *Research Disclosure*, Nos. 11449 and 24241, and JP-A-61-201247: couplers capable of releasing a ligand as described in U.S. Pat. No. 4,555,477; couplers capable of releasing a leuco dye as described in JP-A-63-75747; and couplers capable of releasing a fluorescent dye as described in U.S. Pat. No. 4,774,181.

The amount of the color couplers to be used in combination with the cyan couplers of the present invention ranges from 0.001 to 1 mol per mol of light-sensitive silver halide. More specifically, yellow couplers are used in an amount of from 0.01 to 0.5 mol; magenta couplers from 0.003 to 0.3 mol; and cyan couplers from 0.002 to 0.3 mol, respectively.

These couplers to be used in combination can be introduced into a light-sensitive material by the above-described various known dispersion methods.

The light-sensitive material according to the present invention may contain hydroquinone derivatives, aminophenol derivatives, gallic acid derivatives, ascorbic acid derivatives, etc. as a color fog inhibitor.

The light-sensitive material may also contain various discoloration inhibitors. Examples of suitable organic discoloration inhibitors for cyan, magenta and/or yellow images include hydroquinones, 6-hydroxychromans, 5-hydroxycoumarans, spirochromans, p-alkoxyphenols, hindered phenols chiefly including bisphenols, gallic acid derivatives, methylenedioxybenzenes, aminophenols, hindered amines, and ether or ester derivatives of these phenol compounds obtained by silylating or alkylating the phenolic hydroxyl group thereof. Metal complexes, such as bissalicylaldoximatonickel complexes and bis-N,N-dialkyldithiocarbamatonickel complexes, are also useful.

Specific examples of these organic discoloration inhibitors are described in U.S. Pat. Nos. 2,360,290, 2,418,613, 2,700,453, 2,701,197, 2,728,659, 2,732,300, 2,735,765, 3,982,944, and 4,430,425, British Patent 1,363,921, and U.S. Pat. Nos. 2,710,801 and 2,816,028 for hydroquinones; U.S. Pat. Nos. 3,432,300, 3,573,050, 3,574,627, 3,698,909, and 3,764,337, and JP-A-52-152225 for 6-hydroxychromans, 5-hydroxycoumarans, and spirochromans; U.S. Pat. No. 4,360,589 for spiroindanes; U.S. Pat. No. 2,735,765, British Patent 2,066,975, JP-A-59-10539, and JP-B-57-19765 for p-alkoxyphenols; U.S. Pat. No. 3,700,455, JP-A-52-72224, U.S. Pat. No. 4,228,235, and JP-B-52-6623 for hindered phenols; U.S. Pat. No. 3,457,079 for gallic acid derivatives; U.S. Pat. No. 4,332,886 for methylenedioxybenzenes; JP-B-56-21144 for aminophenols; U.S. Pat. Nos. 3,336,135 and 4,268,593, British Patents 1,326,889, 1,354,313, and 1,410,846, JP-B-51-1420, JP-A-58-114036, JP-A-59-53846, and JP-A-59-78344 for hindered amines; and U.S. Pat. Nos. 4,050,938 and 4,241,155 and British Patent 2,027,731(A) for metal complexes. These compounds are coemulsified together with the corresponding coupler in an amount usually from 5 to 100% by weight based on the coupler and added to a light-sensitive layer.

To prevent fading of a cyan dye image due to heat and particularly to light, it is more effective to incorporate an ultraviolet absorbent into a cyan-forming layer and both layers adjacent thereto. Examples of suitable ultraviolet absorbents include benzotriazole compounds having an aryl substituent as described, e.g., in U.S. Pat. No. 3,533,794; 4-thiazolidone compounds as described, e.g., in U.S. Pat. Nos. 3,314,794 and 3,352,681; benzophenone compounds as described, e.g., in JP-A-46-2784; cinnamic ester compounds as described, e.g., in U.S.

Pat. Nos. 3,705,805 and 3,707,395; butadiene compounds as described, e.g., in U.S. Pat. No. 4,045,229; and benzoxazol compounds as described, e.g., in U.S. Pat. Nos. 3,406,070 and 4,271,307. Ultraviolet absorbing couplers (e.g., α-naphthol type cyan-forming couplers) or ultraviolet absorbing polymers are also useful. These ultraviolet absorbents may be mordanted in a specific layer. Of these ultraviolet absorbents, benzotriazole compounds having an aryl substituent are preferred.

Binders or protective colloids which can be used in the emulsion layers include gelatin to an advantage. Other hydrophilic colloids may be also used either alone or in combination with gelatin. Gelatin to be used in the present invention may be either lime-processed gelatin or acid-processed gelatin. The details for the preparation of gelatin are described in Arthor Vice, *The Macromolecular Chemistry of Gelatin,* Academic Press (1964).

The light-sensitive material of the present invention preferably contains various antiseptics or antifungal agents as described in JP-A-63-257747, JP-A-62-72248, and JP-A-1-80941, such as 1,2-benzisothiazolin-3-one, n-butyl p-hydroxybenzoate, phenol, 4-chloro-3,5-dimethylphenol, 2-phenoxyethanol, and 2-(4-thiazolyl)benzimidazole.

Direct positive color light-sensitive materials according to the present invention can also contain a nucleating agent, such as hydrazine compounds and quaternary heterocyclic compounds, and a nucleation accelerator for enhancing the effect of the nucleating agent as described in *Research Disclosure,* No. 22534 (Jan., 1983).

Supports which can be generally used in the light-sensitive material include a transparent film commonly employed in photographic light-sensitive materials, e.g., a cellulose nitrate film and a polyethylene terephthalate film, and a reflective support. A reflective support is preferred for accomplishing the object of the present invention.

The terminology "reflective support" as used herein means a support having increased reflecting properties to make a dye image formed in the silver halide emulsion layers more distinct. Such a reflective support includes a support having coated thereon a hydrophobic resin having dispersed therein a light reflecting substance, e.g., titanium oxide, zinc oxide, calcium carbonate, and calcium sulfate; and a support made from a hydrophobic resin having dispersed therein the above-mentioned light reflecting substance. Specific examples of suitable reflective supports include baryta paper, polyethylene-coated paper, polypropylene synthetic paper; and a transparent support, e.g., a glass plate, a polyester film (e.g., polyethylene terephthalate, cellulose triacetate, cellulose nitrate), a polyamide film, a polycarbonate film, a polystyrene film, and a vinyl chloride resin film, having thereon a reflective layer or containing therein a reflective substance.

The light-sensitive material according to the present invention can be development processed in a usual manner as described in *Research Disclosure,* No. 17643, pp. 28-29 and ibid., No. 18716, p. 615, left to right columns. For example, color development processing consists of color development, desilvering, and washing. Reversal development processing consists of black-and-white development, washing or rinsing, reversing, and color development. Desilvering consists of bleach with a bleaching bath and fixing with a fixing bath or, alternatively, bleach-fix with a bleach-fix bath. Bleach, fixing, and bleach-fix may be combined in an arbitrary order. Washing may be displaced by stabilization, or washing may be followed by stabilization. Color development, bleach, and fixing may be carried out in a development-bleach-fix monobath. These processing systems may further be combined with pre-hardening, neutralization after pre-hardening, stop-fixing, after-hardening, compensation, intensification, or a like step. Between two of these steps, an intermediate washing step may be inserted. Color development may be replaced with so-called activator treatment.

A color developing solution to be used for development processing is preferably an alkaline aqueous solution containing an aromatic primary amine color developing agent. Useful color developing agents include aminophenol compounds and preferably p-phenylenediamine compounds. Typical examples of p-phenylenediamine compounds are 3-methyl-4-amino-N,N-diethylaniline, 3-methyl-4-amino-N-ethyl-N-β-hydroxyethylaniline,3-methyl-4-amino-N-ethyl-N-β-methanesulfonamidoethylaniline,3-methyl-4-amino-N-ethyl-β-methoxyethylaniline, and salts thereof (e.g., sulfates, hydrochlorides, and p-toluenesulfonates), with 3-methyl-4-amino-N-ethyl-N-β-hydroxyethylaniline sulfate being particularly preferred. These developing agents may be used either individually or in combination of two or more thereof according to the desired purpose.

The color developing solution usually contains pH buffering agents, e.g., carbonates, borates or phosphates of alkali metals, and development inhibitors or antifoggants, e.g., chlorides, bromides, iodides, benzimidazoles, benzothiazoles, and mercapto compounds. If desired, the color developing solution further contains various preservatives, such as hydroxylamine, diethylhydroxylamine, sulfites, hydrazines (e.g., N,N-biscarboxymethylhydrazine), phenyl semicarbazides, triethanolamine, and catecholsulfonic acids; organic solvents, e.g., ethylene glycol and diethylene glycol; development accelerators, e.g., benzyl alcohol, polyethylene glycol, quaternary ammonium salts, and amines; dye forming couplers; competing couplers; auxiliary developing agents (e.g., 1-phenyl-3-pyrazolidone); nucleating agents, e.g., sodium borohydride and hydrazine compounds; viscosity-imparting agents; various chelating agents, such as aminopolycarboxylic acids, aminopolyphosphonic acids, alkylphosphonic acids, and phosphonocarboxylic acids (e.g., ethylenediaminetetraacetic acid, nitrilotriacetic acid, ethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid, and salts thereof); fluorescent brightening agents, e.g., 4,4'-diamino-2,2'-disulfostilbene compounds; and various surface active agents, e.g., alkylsulfonic acids, arylsulfonic acids, aliphatic carboxylic acids, and aromatic carboxylic acids.

In carrying out the present invention, it is preferable to use a developing solution containing substantially no benzyl alcohol. The terminology "substantially no benzyl alcohol" as used herein means that the benzyl alcohol concentration is preferably not more than 2 ml/l, more preferably not more than 0.5 ml/l, and most preferably zero.

It is also preferable to use a developing solution containing substantially no sulfite ion and/or no hydroxylamine. The terminology "substantially no sulfite ion"

as used herein means that the sulfite ion concentration is preferably not more than $3.0 \times 10^{-3}$ mol/l, and more preferably zero. The terminology "substantially no hydroxylamine" as used herein means that the hydroxylamine concentration is preferably not more than $5.0 \times 10^{-3}$ mol/l, and more preferably zero. Accordingly, the developing solution preferably contains an organic preservative other than hydroxylamine or sulfite ion, for example, hydroxylamine derivatives or hydrazine derivatives.

The color developing solution generally has a pH between 9 and 12.

Color reversal development processing generally consists of black-and-white (hereinafter abbreviated as B/W) development, washing or rinsing, and color development. Reversing is carried out by using a reversing bath containing a fogging agent or by reversal exposure. The reversing step may be omitted by incorporating the fogging agent into a color developing solution.

A B/W developing solution to be used for B/W development is a B/W developing solution usually known for processing of B/W light-sensitive materials which contains various known additives. Typical additives include B/W developing agents, e.g., 1-phenyl-3-pyrazolidone, N-methyl-p-aminophenol, and hydroquinone; preservatives, e.g., sulfites; pH buffering agents comprising a water-soluble acid, e.g., acetic acid and boric acid; pH buffering agents or development accelerators comprising an alkali, e.g., sodium carbonate and potassium carbonate; organic or inorganic development inhibitors, e.g., potassium bromide, 2-methylbenzimidazole, and methylbenzothiazole; water softeners, e.g., ethylenediaminetetraacetic acid and polyphosphoric acid salts; antioxidants, e.g., ascorbic acid and diethanolamine; organic solvents, e.g., triethylene glycol and cellosolve; and surface overdevelopment inhibitors, e.g., a trace amount of iodides, and mercapto compounds.

The rate of replenishment for these developing solutions, though varying depending on the kind of color photographic material to be processed, is usually not more than 3 l per m² of a light-sensitive material. The rate of replenishment can be reduced to 500 ml/m² or less by reducing the bromide ion concentration in the replenisher. When processing is carried out at a reduced rate of replenishment, it is desirable to prevent evaporation and aerial oxidation of a processing solution by minimizing the contact area of the processing solution with air. The contact area between a photographic processing solution and air can be minimized by, for example, putting a barrier, such as a floating cover, on the liquid surface, using a movable cover as described in JP-A-1-82033, or utilizing slit development processing as described in JP-A-63-216050. These means are preferably applied to not only color development and B/W development but also to all of the subsequent steps, such as bleach, bleach-fix, fixing, washing, and stabilization. Reduction of the replenishment rate may also be achieved by using a means for suppressing the accumulation of bromide ions in the developing solution.

The processing time with the color developing solution is usually from 2 to 5 minutes. The processing time may be shortened by conducting development processing at an elevated temperature and by an increased pH in an increased concentration of the color developing agent.

The photographic emulsion layers after color development are usually subjected to desilvering consisting of bleach and fixing. Bleach and fixing may be carried out either simultaneously (bleach-fix) or separately. For rapid processing, bleach may be followed by bleach-fix. Further, the mode of desilvering can be arbitrarily selected according to the end use. For example, bleach-fix may be effected using two tanks connected, or fixing may be followed by bleach-fix, or bleach-fix may be followed by bleach. The effects of the present invention are effectively manifested by conducting bleach-fix immediately after color development.

Bleaching agents to be used in a bleaching bath or bleach-fix bath include compounds of polyvalent metals, e.g., iron (III), cobalt (III), chromium (IV), and copper (II); peracids; quinones; and nitroso compounds. Typical bleaching agents include iron chloride, ferricyanides, bichromates, organic complex salts of iron (III), e.g., complex salts with aminopolycarboxylic acids (e.g., ethylenediaminetetraacetic acid, diethylenetriaminepentaacetic acid, cyclohexanediaminetetraacetic acid, methyliminodiacetic acid, 1,3-diaminopropanoltetraacetic acid, glycol ether diaminetetraacetic acid), persulfates, bromates, permanganates, and nitrobenzenes. Preferred among them are aminopolycarboxylic acid iron (III) complexes, e.g., (ethylenediaminetetraacetato)iron (III) salts and (1,3-diaminopropanetetraacetato)iron (III) salts because, with which, the effects of the present invention can be manifested best. Aminopolycarboxylic acid iron (III) complex salts are particularly useful either in a bleaching bath or in a bleach-fix monobath. A bleaching bath or bleach-fix bath containing these aminopolycarboxylic acid iron (III) complex salts usually has a pH between 3.0 and 8.0.

If desired, a fixing bath or a bleach-fix bath may contain known additives, such as re-halogenating agents, e.g., ammonium bromide and ammonium chloride, pH buffering agents, e.g., ammonium nitrate, and metal corrosion inhibitors, e.g., ammonium sulfate.

For the purpose of preventing bleach stain, the bleaching or bleach-fix bath preferably contains organic acids. Particularly preferred organic acids used to this effect are those having an acid dissociation constant (pKa) of from 2 to 5.5, e.g., acetic acid and propionic acid.

Fixing agents which can be used in a fixing or bleach-fix bath include thiosulfates, thiocyanates, thioether compounds, thioureas, and a large quantity of an iodide, with thiosulfates being commonly employed. In particular, ammonium thiosulfate is widely useful. A combined use of a thiosulfate and a thiocyanate, a thioether compound, a thiourea, etc. is also preferred.

Suitable preservatives for the fixing or bleach-fix bath include sulfites, bisulfites, carbonyl-bisulfite adducts, and sulfinic acid compounds described in EP 294769A.

For the purpose of stabilization, the fixing or bleach-fix bath preferably contains various aminopolycarboxylic acids or organophosphonic acids, e.g., 1-hydroxyethylidene-1,1-diphosphonic acid and N,N,N',N'-ethylenediaminetetraphosphonic acid.

The fixing or bleach-fix bath can also contain various fluorescent brightening agents, defoaming agents, surface active agents, polyvinyl pyrrolidone, methanol, etc.

If desired, a fixing bath, a bleach-fix bath or a prebath thereof may contain known bleaching accelerators. Examples of useful bleaching accelerators include compounds having a mercapto group or a disulfide group as described in U.S. Pat. No. 3,893,858, German Patents 1,290,812 and 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426, and *Research Disclosure*, No. 17129 (Jul., 1978); thiazolidine derivatives as described in JP-A-50-140129; thiourea derivatives as described in JP-B-45-8506, JP-A-52-20832, JP-A-53-32735, and U.S. Pat. No. 3,706,561; iodides as described in West German Patent 1,127,715 and JP-A-58-16235; polyoxyethylene compounds as described in German Patents 966,410 and 2,748,430; polyamine compounds described in JP-B-45-8836; compounds described in JP-A-49-40943, JP-A-49-59644, JP-A-53-94927, JP-A-54-35727, JP-A-55-26506, and JP-A-58-163940; and a bromide ion. Among them, compounds having a mercapto group or a disulfide group are preferred because of their high accelerating effect. The compounds disclosed in U.S. Pat. No. 3,893,858, West German Patent 1,290,812, and JP-A-53-95630 are particularly preferred. In addition, the compounds disclosed in U.S. Pat. No. 4,552,834 are also preferred. These bleaching accelerators may be incorporated into a light-sensitive material. The bleaching accelerators are particularly effective for bleach-fix of color light-sensitive materials for photography.

The total time of desilvering is preferably as short as possible as long as sufficient desilvering results. The preferred desilvering time is from 1 to 3 minutes. The desilvering temperature is from 25° to 50° C., and preferably from 35° to 45° C.

It is desirable that desilvering should be performed while enhancing stirring as much as possible. Methods or means for achieving enhanced stirring include a method in which a jet stream of a processing solution is made to strike against the surface of the emulsion layer as described in JP-A-62-183460 and JP-A-62-183461; a method of using a rotating means to enhance stirring effects as described in JP-A-62-183461; a method in which a light-sensitive material is moved with its emulsion surface being in contact with a wire blade placed in a processing solution to make turbulence; and a method of increasing the total flow of a circulating processing solution. These stirring means are effective in any of a bleaching bath, a bleach-fix bath and a fixing bath. Enhanced stirring appears to accelerate the supply of a bleaching agent or a fixing agent to the emulsion layers and, as a result, to increase the rate of desilvering.

The above-described means for enhanced stirring is more effective in the case where a bleaching accelerator is used, markedly enhancing acceleration effects and eliminating the fixing inhibitory effect of the bleaching accelerator.

An automatic developing machine which can be used for processing the light-sensitive material preferably has a means for carrying a light-sensitive material as described in JP-A-60-191257, JP-A-60-191258, and JP-A-60-191259. As mentioned in JP-A-60-191257 supra, such a carrying means is highly effective to considerably reduce carry-over of a processing solution from a bath into a succeeding bath to thereby prevent reduction of processing capacity. This means is particularly effective for reduction of processing time or replenishment rate in each processing step.

After desilvering, the silver halide color light-sensitive material is generally subjected to washing. Washing may be replaced with stabilization. In this case, any of the known stabilizing techniques described, for example, in JP-A-57-8543, JP-A-58-14834, and JP-A-60-220345 can be utilized. Washing may be followed by stabilization using a stabilizing bath containing a dye stabilizer and a surface active agent as a final bath, which is usually used for color light-sensitive materials for photography.

Washing water or a stabilizing bath may contain water softeners, e.g., inorganic phosphoric acids, polyaminocarboxylic acids, and organic aminophosphonic acids; metal salts, e.g., magnesium salts, aluminum salts, and bismuth salts; surface active agents; and hardening agents.

The amount of washing water to be used in the washing step is selected from a broad range depending on the characteristics of the light-sensitive material (e.g., the kind of photographic materials such as couplers), the end use of the light-sensitive material, the temperature of the washing water, the number of washing tanks (the number of stages), the replenishing system (e.g., counter-flow system or direct-flow system), and other various conditions. For example, a relation between the number of washing tanks and the quantity of water in a multi-stage counter-flow system can be decided by the method described in *Journal of the Society of Motion Picture and Television Engineers*, Vol. 64, pp. 248-253 (May, 1955).

According to the disclosed multi-stage counterflow system, the requisite amount of water can be greatly reduced. On the other hand, bacteria tend to grow in the tank with an increase in water retention time, and suspended bacterial cells adhere to light-sensitive materials. Such a problem can be effectively coped with by adopting a method of reducing calcium and magnesium ions in the washing water as described in JP-A-62-288838. It is also effective to use bactericides, such as isothiazolone compounds or thiabendazole compounds as described in JP-A-57-8542; chlorine type bactericides, e.g., chlorinated sodium isocyanurate; and other bactericides described in Horiguchi Hiroshi, *Bokin bobaizai no kagaku*, Sankyo Shuppan (1986), Eisei Gijutsukai (ed.), *Biseibutsu no mekkin, sakkin, bobai gitjutsu* Kogyo Gijutsukai (1982), and Nippon Bokin Bobai Gakkai (ed.), *Bokin bobaizai jiten* (1986), e.g., benzotriazole.

Washing water usually has a pH between 4 and 9, and preferably between 5 and 8. Washing conditions, though varying depending on the characteristics or the end use of the light-sensitive material and the like, are usually from 15° to 45° C. in temperature and from 20 seconds to 10 minutes in time, and preferably from 25° to 40° C. in temperature and from 30 seconds to 5 minutes in time.

Suitable dye stabilizers which can be used in the stabilizing bath include aldehydes (e.g., formalin and glutaraldehyde), N-methylol compounds (e.g., dimethylolurea), hexamethylenetetramine, and an aldehyde-sulfite adduct. If desired, the stabilizing bath may also contain pH buffering agents (e.g., boric acid, sodium hydroxide); chelating agents, (e.g., 1-hydroxyethylidene-1,1-diphosphonic acid, ethylene-diaminetetraacetic acid); sulfiding inhibitors (e.g., alkanolamines); fluorescent brightening agents; and antifungal agents.

The overflow accompanying replenishment for washing and/or stabilization may be reused in other processing steps, such as in a desilvering step.

In cases where each processing solution is concentrated by vaporization during processing with an automatic developing machine, water is preferably supplied to the processing solution for correction of the concentration.

For the purpose of simplifying and speeding up processing, the silver halide light-sensitive material may contain therein a color developing agent, preferably in the form of a precursor thereof. Examples of color developing agent precursors include indoaniline compounds described in U.S. Pat. No. 3,342,597, Schiff base compounds described in U.S. Pat. No. 3,342,599 and *Research Disclosure*, Nos. 14850 and 15159, aldol compounds described in *Research Disclosure*, No. 13924, metal complex salts described in U.S. Pat. No. 3,719,492, and urethane compounds described in JP-A-53-135628.

If desired, the light-sensitive material may further contain therein various 1-phenyl-3-pyrazolidone compounds for the purpose of accelerating color development. Typical examples of these accelerators are described in JP-A-56-64339, JP-A-57-144547, and JP-A-58-115438.

Each of the above-described processing solutions is used at a temperature of from 10° to 50° C. and, in a standard manner, from 33° to 38° C. Higher processing temperatures may be employed for reducing the processing time, or lower temperatures may be employed for improving the image quality or stability of the processing solution. For the purpose of saving silver, intensification, such as cobalt intensification or hydrogen peroxide intensification described in West German Patent 2,226,770 and U.S. Pat. No. 3,674,499, may be adopted.

The present invention is now illustrated in greater detail by way of the following Examples, but it should be understood that the present invention is not deemed to be limited thereto. All the percents and ratios are by weight unless otherwise indicated.

EXAMPLE 1

Preparation of Sample 101

To 10 cc of ethyl acetate were added 1.03 g of coupler (1) and 0.9 cc of tris(2-ethylhexyl) phosphate and they were completely dissolved therein while being maintained at about 40° C. to prepare an oily phase solution.

Separately, 4.2 g of gelatin were added to 26 cc of water at room temperature and, after being thoroughly swollen, the gelatin was completely dissolved by maintaining at about 40° C. To the resulting gelatin aqueous solution maintained at 40° C. were added 3 cc of a 5% sodium dodecylbenzenesulfonate solution and the whole amount of the above-prepared oily phase solution, and the mixture was emulsified and dispersed in a homogenizer to obtain a coupler dispersion (1).

A coating composition having the following formulation was prepared.

| | |
|---|---|
| Silver chlorobromide emulsion (Br content: 30 mol %) | 13 g |
| 10% Gelatin | 28 g |
| Dispersion (1) | 22 g |
| Water | 37 cc |
| Sodium 1-hydroxy-3,5-dichloro-s-triazine (4% aqueous solution) | 5 cc |

The resulting coating composition was coated on a support to a spread of 1 mmol-coupler/m². A protective layer comprising 2 g/m² of gelatin was then coated on the coupler layer to prepare Sample 101.

Preparation of Samples 102 to 109

Samples 102 to 109 were prepared in the same manner as for Sample 101, except for replacing coupler (1) with an equimolar amount of each of the couplers shown in Table 2 below.

Sample 106 was prepared in the same manner as for Sample 105, except for replacing tris(2-ethylhexyl) phosphate with 1.0 cc of a high-boiling organic solvent (70) shown below.

High-Boiling Organic Solvent (70)

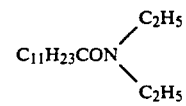

Each of Samples 101 to 109 was wedgewise exposed to white light and subjected to color development processing according to the following processing schedule (I). Color developability and image stability of the sample were evaluated according to the following test methods.

1) Color Developability

Color developability was expressed by a value obtained by dividing the maximum slope of a tangent line on the characteristic curve by the maximum density ($D_{max}$). That is:

$$\text{Color Developability} = \frac{\text{Maximum Slope}}{D_{max}}$$

The processed sample was allowed to stand at 80° C. and 70% RH for 3 days for accelerated deterioration. Image stability was expressed in terms of a density after the accelerated deterioration test of the area whose initial density before the test was 1.0.

The results of these evaluations are shown in Table 2.

| Processing Schedule (I): | | |
|---|---|---|
| Step | Temp. | Time |
| Color Development | 35° C. | 3 minutes |
| Bleach-fix | 30–36° C. | 45 seconds |
| Stabilization (1) | 30–37° C. | 20 seconds |
| Stabilization (2) | 30–37° C. | 20 seconds |
| Stabilization (3) | 30–37° C. | 20 seconds |
| Stabilization (4) | 30–37° C. | 30 seconds |
| Drying | 70–85° C. | 60 seconds |

(Stabilization was effected in a 4-tank counter-flow system of from tank (4) towards tank (1).)

Each processing solution has the following composition:

| | |
|---|---|
| Color Developing Solution: | |
| Water | 800 ml |
| Ethylenediaminetetraacetic acid | 2.0 g |
| Triethanolamine | 8.0 g |
| Sodium chloride | 1.4 g |
| Potassium bromide | 0.6 g |
| Potassium carbonate | 25 g |
| N-Ethyl-N-(β-methanesulfonamidoethyl)-3-methyl-4-aminoaniline sulfate | 5.0 g |
| N,N-Diethylhydroxylamine | 4.2 g |
| 5,6-Dihydroxybenzene-1,2,4-tri- | 0.3 g |

-continued

| | |
|---|---|
| sulfonic acid | |
| Fluorescent brightening agent (4,4',-diaminostilbene type) | 2.0 g |
| Water to make | 1000 ml |
| pH (25° C.) | 10.25 |
| Bleach-Fix Bath: | |
| Water | 400 ml |
| Ammonium thiosulfate (700 g/l) | 100 ml |
| Sodium sulfite | 18 g |
| Ammonium (ethylenediaminetetra-acetato) iron (III) | 55 g |
| Disodium ethylenediaminetetra-acetate | 3 g |
| Glacial acetic acid | 8 g |
| Water to make | 1000 ml |
| pH (25° C.) | 5.5 |
| Stabilizing Bath: | |
| Formalin (37%) | 0.1 g |
| Formalin-sulfite adduct | 0.7 g |
| 5-Chloro-2-methyl-4-isothiazolin-3-one | 0.02 g |
| 2-Methyl-4-isothiazolin-3-one | 0.01 g |
| Copper sulfate | 0.005 g |
| Water to make | 1000 ml |
| pH (25° C.) | 4.0 |

TABLE 2

| Sample No. | Coupler No. | Color Developability* | Image Stability | Remark |
|---|---|---|---|---|
| 101 | (1) | 1.0 | 0.99 | Invention |
| 102 | (6) | 0.9 | 0.98 | " |
| 103 | (7) | 1.0 | 0.97 | " |
| 104 | (12) | 1.0 | 0.99 | " |
| 105 | (33) | 1.2 | 0.99 | " |
| 106 | (33) | 1.4 | 0.99 | " |
| 107 | (52) | 1.3 | 0.99 | " |
| 108 | (53) | 1.2 | 0.99 | " |
| 109 | (R-1) | 0.5 | 0.68 | Comparison |

Note:
*Relative value taking color developability of Sample 101 as a standard (1.0).

The results in Table 2 above clearly prove superiority of the couplers according to the present invention in both color developability and image stability. In particular, it can be seen that the use of an amide type high boiling organic solvent provides a still better color developability.

EXAMPLE 2

Polyethylene-(double side) coated paper was subjected to a corona discharge treatment, and a gelatin subbing layer containing sodium dodecylbenzenesulfonate was formed thereon. On the subbing layer were coated the following layers to prepare a multi-layer color paper (designated Sample 201).

Coating compositions were prepared as follows.

To a mixture of 19.1 g of a yellow coupler (ExY), 4.4 g of a dye image stabilizer (Cpd-1), and 0.7 g of a dye image stabilizer (Cpd-7) were added 27.2 cc of ethyl acetate, 4.1 g of a solvent (Solv-3), and 4.1 g of a solvent (Solv-7) to form a solution. The solution was dispersed in 185 cc of a 10% gelatin aqueous solution containing 8 cc of a 10% sodium dodecylbenzenesulfonate solution to prepare dispersion A. Separately, silver chlorobromide emulsion A (a 3:7 (by silver mole ratio) mixture of an emulsion containing cubic grains having a mean grain size of 0.88 μm with a coefficient of variation of grain size distribution of 0.08 (hereinafter referred to as a larger size emulsion A) and an emulsion containing cubic grains having a mean grain size of 0.70 μm with a coefficient of variation of grain size distribution of 0.10 (hereinafter referred to as a smaller size emulsion A), both emulsions having a local phase comprising 0.3 mol % of silver bromide on a part of the grain surface) were prepared. To the emulsion A were added blue-sensitive sensitizing dyes A and B shown below each in an amount of $2.0 \times 10^{-4}$ mol per mol of silver for the larger size emulsion A and in an amount of $2.5 \times 10^{-4}$ mol per mol of silver for the smaller size emulsion A. Chemical ripening of emulsion A was conducted by addition of a sulfur sensitizer and a gold sensitizer. The finished emulsion A and the above-prepared dispersion A were mixed together to prepare a first layer coating composition having a composition shown below.

Coating compositions for the 2nd to 7th layers were prepared in a similar manner as described above. Each layer further contained sodium 1-hydroxy-3,5-dichloro-s-triazine as a gelatin hardening agent.

Each layer also contained Cpd-10 and Cpd-11 in a total amount of 25.0 mg/m² and 50.0 mg/m², respectively.

Spectral sensitizing dyes used for light-sensitive emulsion layers were as follows.

For Blue-Sensitive Layer:

Sensitizing Dye A

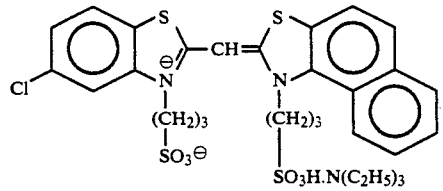

and ($2.0 \times 10^{-4}$ mol/mol-Ag for larger size emulsion A;
$2.5 \times 10^{-4}$ mol/mol-Ag for smaller size emulsion B)

and

Sensitizing Dye B

-continued

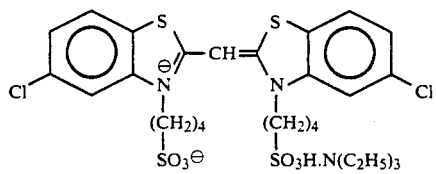

(2.0 × 10$^{-4}$ mol/mol-Ag for larger size emulsion A;
2.5 × 10$^{-4}$ mol/mol-Ag for smaller size emulsion B)

For Green-Sensitive Layer:

Sensitizing Dye C

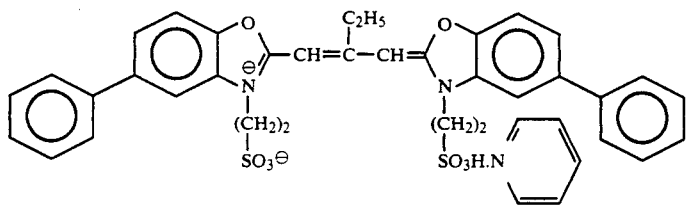

and (4.0 × 10$^{-4}$ mol/mol-Ag for larger size emulsion B;
5.6 × 10$^{-4}$ mol/mol-Ag for smaller size emulsion B)

and

Sensitizing Dye D

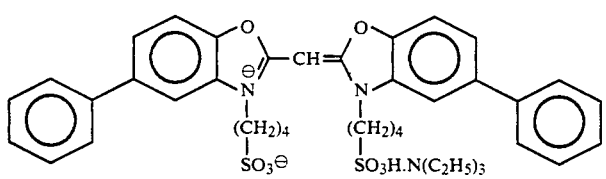

(7.0 × 10$^{-5}$ mol/mol-Ag for larger size emulsion B;
1.0 × 10$^{-5}$ mol/mol-Ag for smaller size emulsion B)

For Red-Sensitive Layer:

Sensitizing Dye E

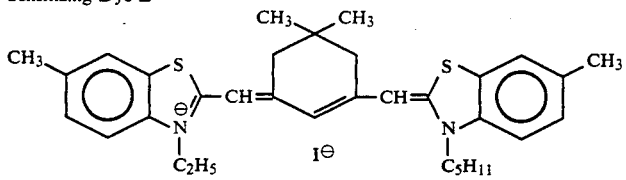

(0.9 × 10$^{-4}$ mol/mol-Ag for larger size emulsion C;
1.1 × 10$^{-4}$ mol/mol-Ag for smaller size emulsion C)

To the red-sensitive emulsion layer was further added 2.6 × 10$^{-3}$ mol/mol-Ag of a compound having formula:

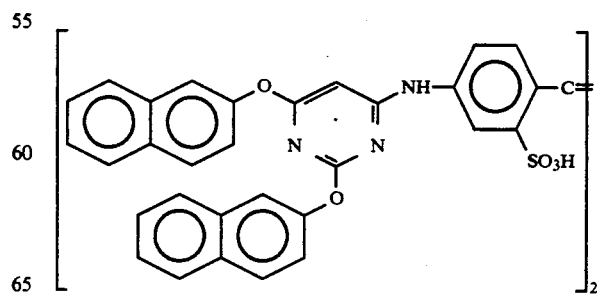

To each of the blue-sensitive emulsion layer, green-sensitive emulsion layer, and red-sensitive emulsion layer was added 1-(5-methylureidophenyl)-5-mercaptotetrazole in an amount of $8.5 \times 10^{-5}$ mol, $7.7 \times 10^{-4}$ mol, and $2.5 \times 10^{-4}$ mol, respectively, each per mol of silver halide.

To each of the blue-sensitive emulsion layer and green-sensitive emulsion layer was added 4-hydroxy-6-methyl-1,3,3a,7-tetraazaindene in an amount of $1 \times 10^{-4}$ mol and $2 \times 10^{-4}$ mol, respectively, per mol of silver halide.

For the purpose of irradiation prevention, the following dyes were added to each emulsion layer in the amount shown in parentheses.

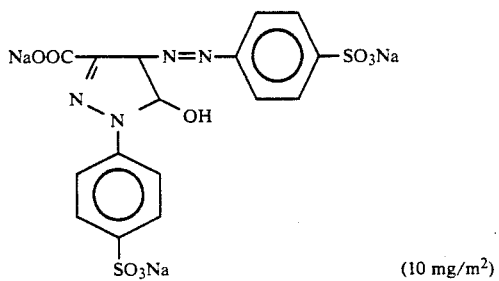

(10 mg/m$^2$)

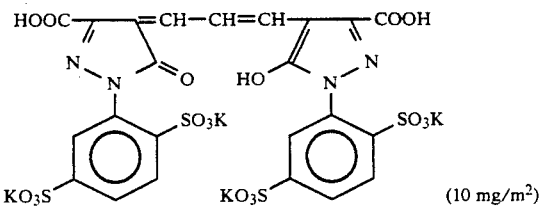

(10 mg/m$^2$)

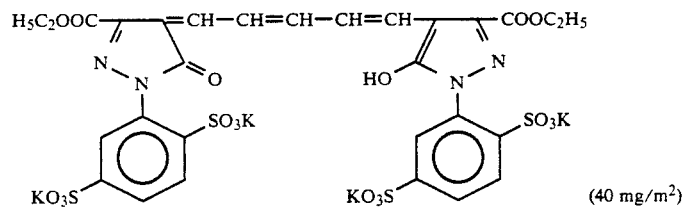

(40 mg/m$^2$)

and

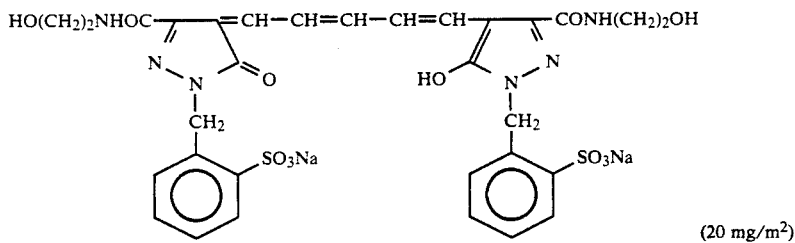

(20 mg/m$^2$)

Layer Structure

Support

Polyethylene-coated paper, the polyethylene layer on the size of the 1st layer containing a white pigment (TiO$_2$) and a bluing dye (ultramarine).

| 1st Layer (Blue-Sensitive Layer): | |
|---|---|
| The above-described silver chlorobromide emulsion A | 0.30 g/m$^2$ as Ag |
| Gelatin | 1.86 g/m$^2$ |
| Yellow coupler (ExY) | 0.82 g/m$^2$ |
| Dye image stabilizer (Cpd-1) | 0.19 g/m$^2$ |
| Solvent (Solv-3) | 0.18 g/m$^2$ |
| Solvent (Solv-7) | 0.18 g/m$^2$ |
| Dye image stabilizer (Cpd-7) | 0.06 g/m$^2$ |
| 2nd Layer (Color Mixing Preventive Layer): | |
| Gelatin | 0.99 g/m$^2$ |
| Color mixing inhibitor (Cpd-5) | 0.08 g/m$^2$ |
| Solvent (Solv-1) | 0.16 g/m$^2$ |
| Solvent (Solv-4) | 0.08 g/m$^2$ |
| 3rd layer (Green-Sensitive Emulsion Layer): | |
| Silver chlorobromide emulsion (cubic; 1:3 (Ag molar ratio) mixture of largesize emulsion B having a mean grain size of 0.55 μm with a coefficient of grain size variation of 0.10 and smaller size | 0.12 g/m$^2$ as Ag |

-continued emulsion B having a mean grain size of 0.39 μm with a coefficient
of grain size variation of 0.08, both emulsions having a local phase compris-
ing 0.8 mol % of AgBr on grain surfaces)

| | |
|---|---|
| Gelatin | 1.24 g/m² |
| Magenta coupler (ExM) | 0.23 g/m² |
| Dye image stabilizer (Cpd-2) | 0.03 g/m² |
| Dye image stabilizer (Cpd-3) | 0.16 g/m² |
| Dye image stabilizer (Cpd-4) | 0.02 g/m² |
| Dye image stabilizer (Cpd-9) | 0.02 g/m² |
| Solvent (Solv-2) | 0.40 g/m² |

4th Layer (Ultraviolet Absorbing Layer):

| | |
|---|---|
| Gelatin | 1.58 g/m² |
| Ultraviolet absorbent (UV-1) | 0.47 g/m² |
| Color mixing inhibitor (Cpd-5) | 0.05 g/m² |
| Solvent (Solv-5) | 0.24 g/m² |

5th Layer (Red-Sensitive Layer):

| | |
|---|---|
| Silver chlorobromide emulsion (cubic: 1:4 (Ag molar ratio) | 0.23 g/m² as Ag | mixture of larger size emulsion C having a mean grain size of
0.58 μm with a coefficient of size variation of 0.09 and smaller
size emulsion C having a mean grain size of 0.45 μm with a coefficient of size
variation of 0.11, both having a local phase comprising 0.6 mol % of
AgBr on grain surfaces)

| | |
|---|---|
| Gelatin | 1.34 g/m² |
| Cyan coupler (ExC) | 0.32 g/m² |
| Dye image stabilizer (Cpd-2) | 0.03 g/m² |
| Dye image stabilizer (Cpd-4) | 0.02 g/m² |
| Dye image stabilizer (Cpd-6) | 0.18 g/m² |
| Dye image stabilizer (Cpd-7) | 0.40 g/m² |
| Dye image stabilizer (Cpd-8) | 0.05 g/m² |
| Solvent (Solv-6) | 0.14 g/m² |

6th Layer (Ultraviolet Absorbing Layer):

| | |
|---|---|
| Gelatin | 0.53 g/m² |
| Ultraviolet absorbent (UV-1) | 0.16 g/m² |
| Color mixing inhibitor (Cpd-5) | 0.02 g/m² |
| Solvent (Solv-5) | 0.08 g/m² |

7th Layer (Protective Layer):

| | |
|---|---|
| Gelatin | 1.33 g/m² |
| Acryl-modified polyvinyl alcohol copolymer (degree of modification: 17%) | 0.17 g/m² |
| Liquid paraffin | 0.03 g/m² |

Yellow Coupler (ExY):

1:1 (by mole) mixture of:

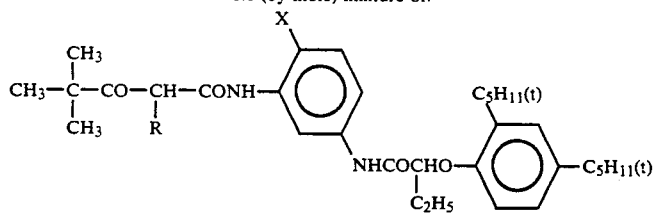

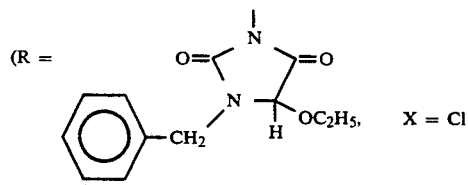

and

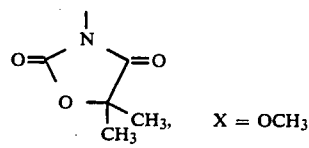

Magenta Coupler (ExM):

-continued
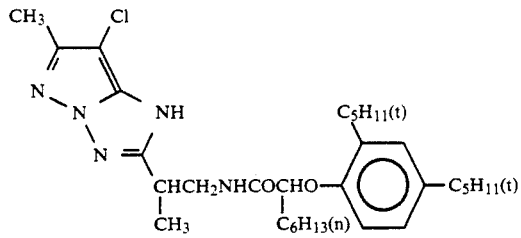
Cyan Coupler (ExC):
1:1 (by mole) mixture of
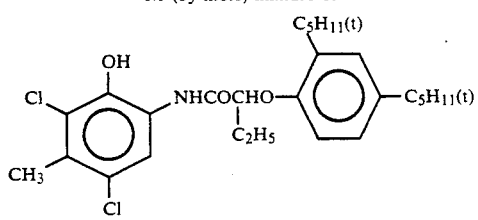
and
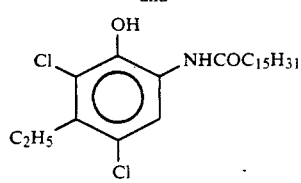
Dye Image Stabilizer (Cpd-1):
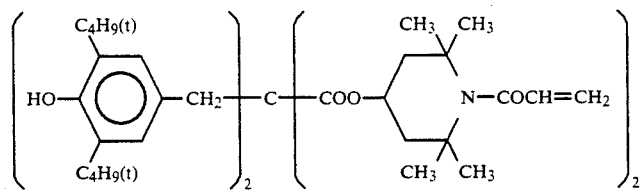
Dye Image Stabilizer (Cpd-2):
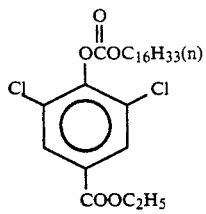
Dye Image Stabilizer (Cpd-3):
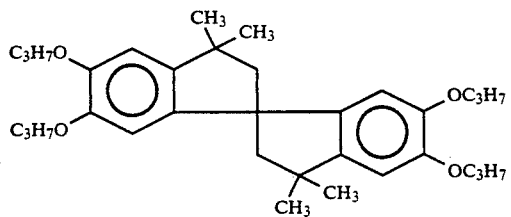
Dye Image Stabilizer (Cpd-4):

-continued
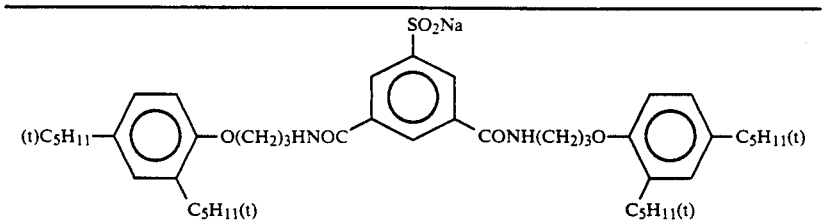
Color Mixing Inhibitor (Cpd-5):
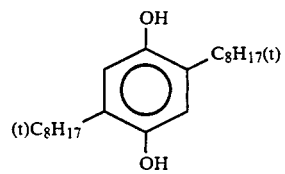
Dye Image Stabilizer (Cpd-6):
2:4:4 (by weight) mixture of:
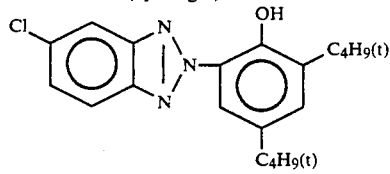
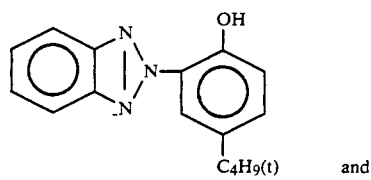  and
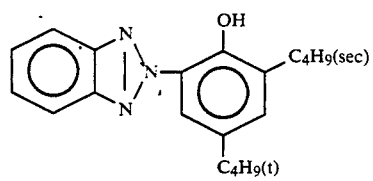
Dye Image Stabilizer (Cpd-7):
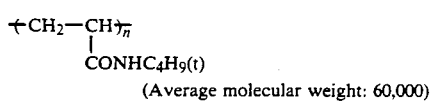
(Average molecular weight: 60,000)
Dye Image Stabilizer (Cpd-8):
1:1 (by weight) mixture of:
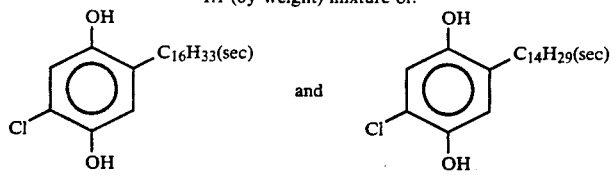
Dye Image Stabilizer (Cpd-9):
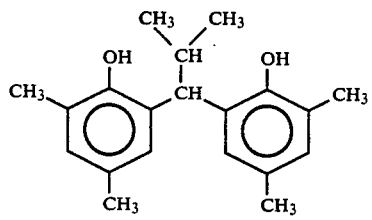

-continued
Antiseptic (Cpd-10):
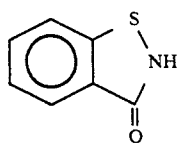
Antiseptic (Cpd-11):
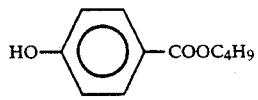
Ultraviolet Absorbent (UV-1):
4:2:4 (by weight) mixture of:
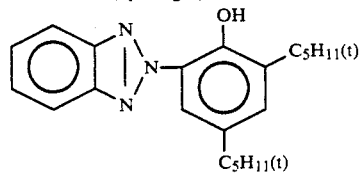
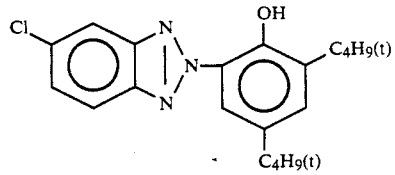 and
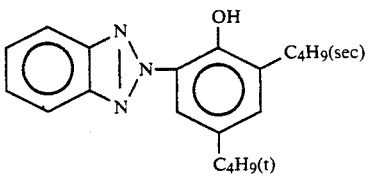
Solvent (Solv-1):
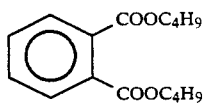
Solvent (Solv-2):
1:1 (by volume) mixture of:
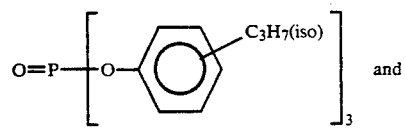 and
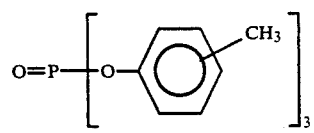
Solvent (Solv-3):
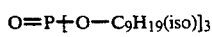
Solvent (Solv-4):

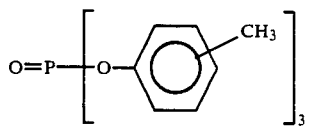

Solvent (Solv-5):

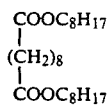

Solvent (Solv-6):

80:20 (by volume) mixture of:

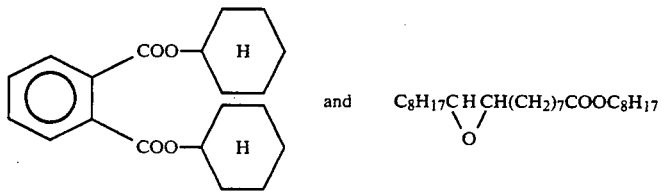

Solvent (Solv-7):

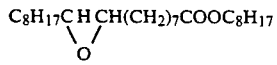

Preparation of Samples 202 to 207

Samples 202 to 207 were prepared in the same manner as for Sample 201, except that coupler ExC in the 5th layer was replaced by the coupler indicated in Table 3 below in a molar amount one third as much as the molar amount of cyan coupler ExC and the amount of the emulsion was changed such that the molar ratio of silver to coupler is equal to that of Sample 201. The amount of the solvent used was one third as much as that used in Sample 201.

Each of Samples 201 to 207 was exposed to light in the same manner as in Example 1, but to red light.

The exposed Sample 201 was continuously processed according to the schedule (II) shown below by means of a paper processing machine until the amount of a replenisher for color development reached twice the volume of the developing tank (running test).

After the running test, each of the exposed Samples 201 to 207 was processed, and color developability, image stability and color reproducibility of the processed sample were evaluated in the same manner as in Example 1. Evaluation of the color reproducibility in the blue and green regions was expressed as follows:
Excellent . . . E
Good . . . G
Control . . . C The results obtained are shown in Table 3.

Processing Schedule (II):

| Step | Temp. (°C.) | Time (sec) | Replenisher (ml/m²) | Tank Volume (l) |
|---|---|---|---|---|
| Color Development | 35 | 45 | 161 | 1.7 |
| Bleach-fix | 30–35 | 45 | 215 | 1.7 |
| Rinsing (1) | 30–35 | 20 | — | 1.0 |
| Rinsing (2) | 30–35 | 20 | — | 1.0 |
| Rinsing (3) | 30–35 | 20 | 350 | 1.0 |
| Drying | 70–80 | 60 | | |

Rinsing was effected in a 3-tank counter-flow system from tank (3) towards tank (1).

Each processing solution had the following composition.

| | Tank Solution | Replenisher |
|---|---|---|
| Color Developing Solution: | | |
| Water | 800 ml | 800 ml |
| Ethylenediamine-N,N,N,N-tetramethylenephosphonic acid | 1.5 g | 2.0 g |
| Triethanolamine | 8.0 g | 12.0 g |
| Sodium chloride | 1.4 g | — |
| Potassium carbonate | 25 g | 25 g |
| N-Ethyl-N-(β-methanesulfon-amidoethyl)-3-methyl-4-amino-aniline sulfate | 5.0 g | 7.0 g |
| N,N-Bis(carboxymethyl)hydrazine | 5.5 g | 7.0 g |
| Fluorescent brightening agent ("WHITEX 4B" produced by Sumitomo Chemical Co., Ltd.) | 1.0 g | 2.0 g |
| Water to make | 1000 ml | 1000 ml |
| pH (25° C.) | 10.05 | 10.45 |
| Bleach-Fix Bath: | | |

Tank solution and replenisher had the same formulation.

| | |
|---|---|
| Water | 400 ml |
| Ammonium thiosulfate (700 g/l) | 100 ml |
| Sodium sulfite | 17 g |
| Ammonium (ethylenediaminetetra-acetato) iron (III) | 55 g |
| Disodium ethylenediaminetetraacetate | 5 g |
| Ammonium bromide | 40 g |
| Water to make | 1000 ml |
| pH (25° C.) | 6.0 |

Rinsing Batch:
Tank solution and replenisher had the same formulation.
Ion-exchanged water (calcium and magnesium ions were reduced to 3 ppm, respectively).

TABLE 3

| Sample No. | No. of Coupler in 5th Layer | Color Developability* | Color Reproducibility | Image Stability | Remark |
|---|---|---|---|---|---|
| 201 | ExC | 0.6 | C | 0.68 | Comparison |
| 202 | (1) | 1.0 | G | 0.98 | Invention |
| 203 | (7) | 0.9 | G | 0.99 | " |
| 204 | (12) | 1.0 | G | 0.97 | " |
| 205 | (33) | 1.2 | G | 0.99 | " |
| 206 | (52) | 1.2 | G | 0.99 | " |
| 207 | (53) | 1.1 | E | 0.99 | " |

Note: *Relatively expressed, taking color developability of Sample 202 as a standard (1.0).

It can be seen from Table 3 that the color papers containing the coupler of the present invention are excellent in color developability and image stability even when processed with a color developing solution containing no benzyl alcohol.

Further, each of the exposed Samples 201 to 207 was processed in the same manner as described in processing schedule II above, except for changing the pH of the bleach-fix bath to 5.0 (processing schedule (III)). The difference between the maximum density obtained in the processing schedule (III) and that obtained in the processing schedule (II) (pH of the bleach-fix bath: 6.0) was obtained. The difference is an indication of the insufficiency of color reproduction. The results obtained are shown in Table 4.

TABLE 4

| Sample No. | $\Delta D_{max}$ ($D_{max}$ (pH 5.0)–$D_{max}$ (pH 6.0)) | Remark |
|---|---|---|
| 201 | −0.32 | Comparison |
| 202 | ±0.0 | Invention |
| 203 | ±0.0 | " |
| 204 | ±0.0 | " |
| 205 | ±0.0 | " |
| 206 | ±0.0 | " |
| 207 | ±0.0 | " |

The results in Table 4 reveal the light-sensitive material containing the coupler of the present invention maintains its excellent color reproducibility even when processed with a processing solution having a bleaching ability with a reduced oxidizing power.

EXAMPLE 3

On a cellulose triacetate film support having a subbing layer, the following layers were coated to prepare a multi-layer color light-sensitive material (designated Sample 301). In the following AgX means a silver halide.

| 1st Layer (Antihalation Layer): | |
|---|---|
| Black colloidal silver | 0.18 g/m$^2$ as Ag |
| Gelatin | 1.40 g/m$^2$ |
| 2nd Layer (Intermediate Layer): | |
| EX-1 | 0.070 g/m$^2$ |
| EX-3 | 0.020 g/m$^2$ |
| EX-12 | 2.0 × 10$^{-3}$ g/m$^2$ |
| U-1 | 0.060 g/m$^2$ |
| U-2 | 0.080 g/m$^2$ |
| U-3 | 0.10 g/m$^2$ |
| HBS-1 | 0.10 g/m$^2$ |
| HBS-2 | 0.020 g/m$^2$ |
| Gelatin | 1.04 g/m$^2$ |
| 3rd layer (1st Red-Sensitive Emulsion Layer): | |
| Emulsion A | 0.25 g/m$^2$ as Ag |
| Emulsion B | 0.25 g/m$^2$ as Ag |
| Sensitizing Dye I | 6.9 × 10$^{-5}$ mol/mol-AgX |
| Sensitizing Dye II | 1.8 × 10$^{-5}$ mol/mol-AgX |
| Sensitizing Dye III | 3.1 × 10$^{-4}$ mol/mol-AgX |
| EX-2 | 0.34 g/m$^2$ |
| EX-10 | 0.020 g/m$^2$ |
| U-1 | 0.070 g/m$^2$ |
| U-2 | 0.050 g/m$^2$ |
| U-3 | 0.070 g/m$^2$ |
| HBS-1 | 0.060 g/m$^2$ |
| Gelatin | 0.87 g/m$^2$ |
| 4th Layer (2nd Red-Sensitive Emulsion Layer): | |
| Emulsion G | 1.00 g/m$^2$ as Ag |
| Sensitizing Dye I | 5.1 × 10$^{-5}$ mol/mol-AgX |
| Sensitizing Dye II | 1.4 × 10$^{-5}$ mol/mol-AgX |
| Sensitizing Dye III | 2.3 × 10$^{-4}$ mol/mol-Agx |
| EX-2 | 0.40 g/m$^2$ |
| EX-3 | 0.050 g/m$^2$ |
| EX-10 | 0.015 g/m$^2$ |
| U-1 | 0.070 g/m$^2$ |
| U-2 | 0.050 g/m$^2$ |
| U-3 | 0.070 g/m$^2$ |
| Gelatin | 1.30 g/m$^2$ |
| 5th Layer (3rd Red-Sensitive Emulsion Layer): | |
| Emulsion D | 1.60 g/m$^2$ as Ag |
| Sensitizing Dye I | 5.4 × 10$^{-5}$ mol/mol-AgX |
| Sensitizing Dye II | 1.4 × 10$^{-5}$ mol/mol-AgX |
| Sensitizing Dye III | 2.4 × 10$^{-4}$ mol/mol-AgX |
| EX-2 | 0.097 g/m$^2$ |
| EX-3 | 0.010 g/m$^2$ |
| EX-4 | 0.080 g/m$^2$ |
| HBS-1 | 0.22 g/m$^2$ |
| HBS-2 | 0.10 g/m$^2$ |
| Gelatin | 1.63 g/m$^2$ |
| 6th Layer (Intermediate Layer): | |
| EX-5 | 0.040 g/m$^2$ |
| HBS-1 | 0.020 g/m$^2$ |
| Gelatin | 0.80 g/m$^2$ |
| 7th Layer (1st Green-Sensitive Emulsion Layer): | |
| Emulsion A | 0.15 g/m$^2$ as Ag |
| Emulsion B | 0.15 g/m$^2$ as Ag |
| Sensitizing Dye IV | 3.0 × 10$^{-5}$ mol/mol-AgX |
| Sensitizing Dye V | 1.0 × 10$^{-4}$ mol/mol-AgX |
| Sensitizing Dye VI | 3.8 × 10$^{-4}$ mol/mol-AgX |
| EX-1 | 0.021 g/m$^2$ |
| EX-6 | 0.26 g/m$^2$ |
| EX-7 | 0.030 g/m$^2$ |
| EX-8 | 0.025 g/m$^2$ |
| HBS-1 | 0.10 g/m$^2$ |
| HBS-3 | 0.010 g/m$^2$ |
| Gelatin | 0.63 g/m$^2$ |
| 8th Layer (2nd Green-Sensitive Emulsion Layer): | |
| Emulsion C | 0.45 g/m$^2$ as Ag |
| Sensitizing Dye IV | 2.1 × 10$^{-5}$ mol/mol-AgX |
| Sensitizing Dye V | 7.0 × 10$^{-5}$ mol/mol-AgX |
| Sensitizing Dye VI | 2.6 × 10$^{-4}$ mol/mol-AgX |
| EX-6 | 0.094 g/m$^2$ |
| EX-7 | 0.026 g/m$^2$ |
| EX-8 | 0.018 g/m$^2$ |
| HBS-1 | 0.16 g/m$^2$ |
| HBS-3 | 8.0 × 10$^{-3}$ g/m$^2$ |
| Gelatin | 0.50 g/m$^2$ |
| 9th Layer (3rd Green-Sensitive Emulsion Layer): | |
| Emulsion E | 1.20 g/m$^2$ as Ag |
| Sensitizing Dye IV | 3.5 × 10$^{-5}$ mol/mol-AgX |
| Sensitizing Dye V | 8.0 × 10$^{-5}$ mol/mol-AgX |
| Sensitizing Dye VI | 3.0 × 10$^{-4}$ mol/mol-AgX |
| EX-1 | 0.025 g/m$^2$ |
| EX-11 | 0.10 g/m$^2$ |
| EX-13 | 0.015 g/m$^2$ |
| HBS-1 | 0.25 g/m$^2$ |
| HBS-2 | 0.10 g/m$^2$ |
| Gelatin | 1.54 g/m$^2$ |
| 10th Layer (Yellow Filter Layer): | |
| Yellow colloidal silver | 0.050 g/m$^2$ as Ag |
| EX-5 | 0.080 g/m$^2$ |

-continued

| | |
|---|---|
| HBS-1 | 0.030 g/m² |
| Gelatin | 0.95 g/m² |
| 11th Layer (1st Blue-Sensitive Emulsion Layer): | |
| Emulsion A | 0.080 g/m² as Ag |
| Emulsion B | 0.070 g/m² as Ag |
| Emulsion F | 0.070 g/m² as Ag |
| Sensitizing Dye VII | $3.5 \times 10^{-4}$ mol/mol-AgX |
| EX-8 | 0.042 g/m² |
| EX-9 | 0.72 g/m² |
| HBS-1 | 0.28 g/m² |
| Gelatin | 1.10 g/m² |
| 12th Layer (2nd Blue-Sensitive Emulsion Layer): | |
| Emulsion G | 0.45 g/m² as Ag |
| Sensitizing Dye VII | $2.1 \times 10^{-4}$ mol/mol-AgX |
| EX-9 | 0.15 g/m² |
| EX-10 | $7.0 \times 10^{-3}$ g/m² |
| HBS-1 | 0.050 g/m² |
| Gelatin | 0.78 g/m² |
| 13th Layer (3rd Blue-Sensitive Emulsion Layer): | |
| Emulsion H | 0.77 g/m² as Ag |
| Sensitizing Dye VII | $2.2 \times 10^{-4}$ mol/mol-AgX |
| EX-9 | 0.20 g/m² |
| HBS-1 | 0.070 g/m² |
| Gelatin | 0.69 g/m² |
| 14th Layer (1st Protective Layer): | |

-continued

| | |
|---|---|
| Emulsion I | 0.20 g/m² as Ag |
| U-4 | 0.11 g/m² |
| U-5 | 0.17 g/m² |
| HBS-1 | $5.0 \times 10^{-2}$ g/m² |
| Gelatin | 1.00 g/m² |
| 15th Layer (2nd Protective Layer): | |
| H-1 | 0.40 g/m² |
| B-1 (diameter: 1.7 μm) | $5.0 \times 10^{-2}$ g/m² |
| B-2 (diameter: 1.7 μm) | 0.10 g/m² |
| B-3 | 0.10 g/m² |
| S-1 | 0.20 g/m² |
| Gelatin | 1.20 g/m² |

Each layer further contained W-1, W-2, W-3, B-4, B-5, F-1, F-2, F-3, F-4, F-5, F-6, F-7, F-8, F-9, F-10, F-11, F-12, F-13 and an iron salt, a lead salt, a gold salt, a platinum salt, an iridium salt, and a rhodium salt as additives for improving preservability, processability, pressure resistance, antifungal and antibacterial properties, antistatic properties, and coating properties.

Emulsions A to I used in the sample preparation are shown in Table 5 below.

TABLE 5

| Emulsion No. | Average AgI Content (%) | Mean Grain Size (μm) | Coefficient of Variation of Grain Size (%) | Diameter/ Thickness Ratio | Silver Content Ratio (AgI Content (%)), Grain Structure |
|---|---|---|---|---|---|
| A | 4.0 | 0.45 | 27 | 1 | core/shell = 1/3 (13/1), double structure |
| B | 8.9 | 0.70 | 14 | 1 | core/shell = 3/7 (25/2), double structure |
| C | 10 | 0.75 | 30 | 2 | core/shell = 1/2 (24/3), double structure |
| D | 16 | 1.05 | 35 | 2 | core/shell = 4/6 (40/0), double structure |
| E | 10 | 1.05 | 35 | 3 | core/shell = 1/2 (24/3), double structure |
| F | 4.0 | 0.25 | 28 | 1 | core/shell = 1/3 (13/1), double structure |
| G | 14.0 | 0.75 | 25 | 2 | core/shell = 1/2 (42/0), double structure |
| H | 14.5 | 1.30 | 25 | 3 | core/shell = 37/63 (34/3), double structure |
| I | 1 | 0.07 | 15 | 1 | uniform structure |

Chemical structures and names of the compounds used in the sample preparation are shown below.

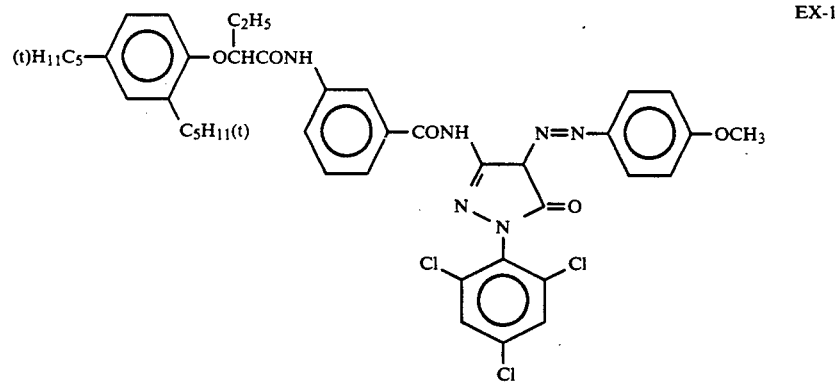

EX-1

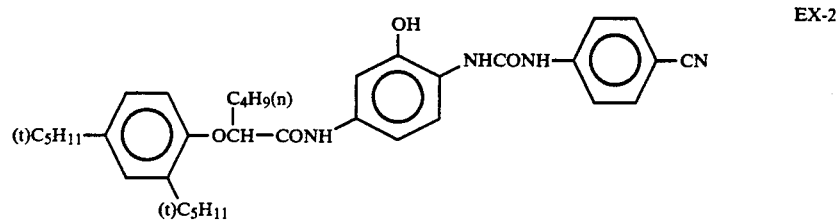

EX-2

-continued
EX-3
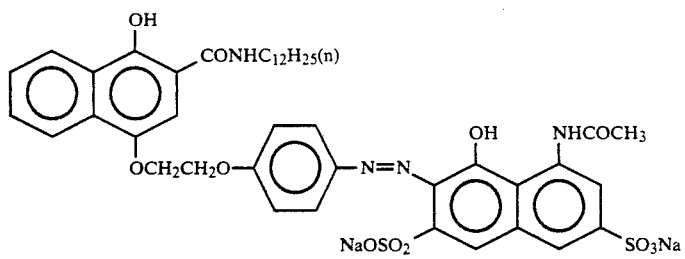
EX-4
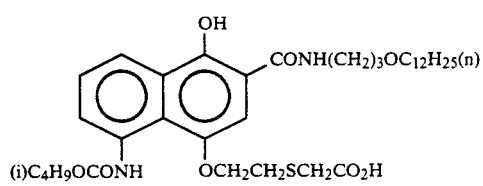
EX-5
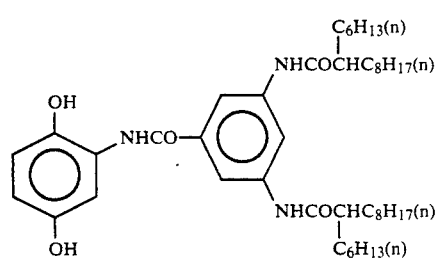
EX-6
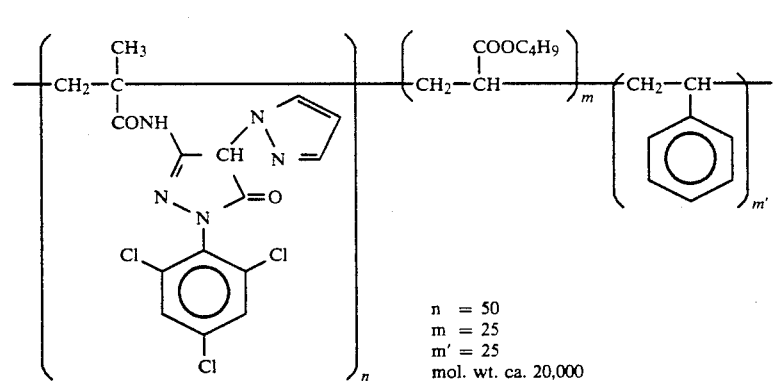
n = 50
m = 25
m' = 25
mol. wt. ca. 20,000
EX-7
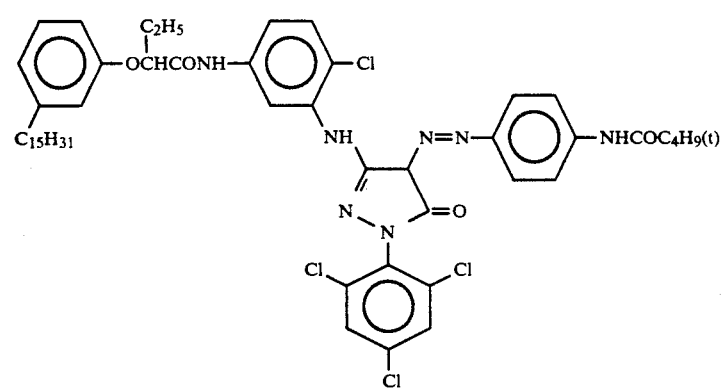

-continued
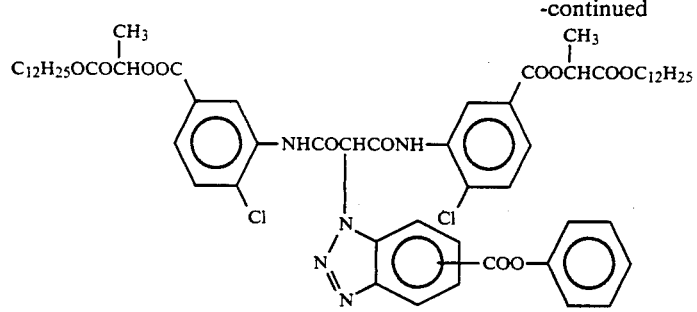 EX-8
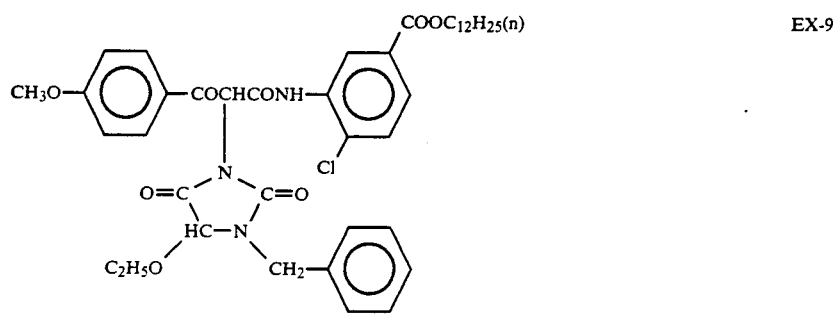 EX-9
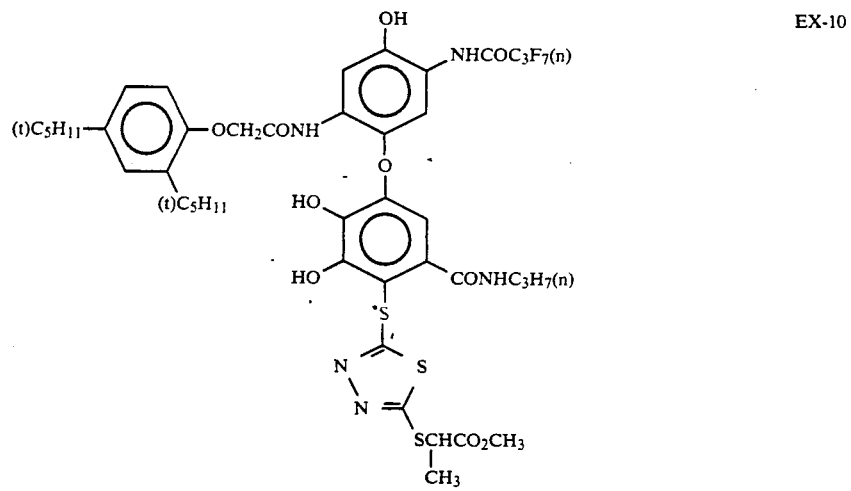 EX-10
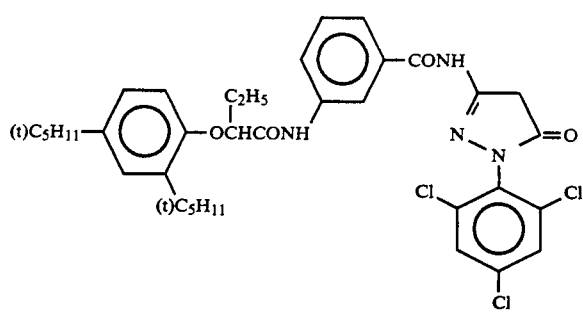 EX-11
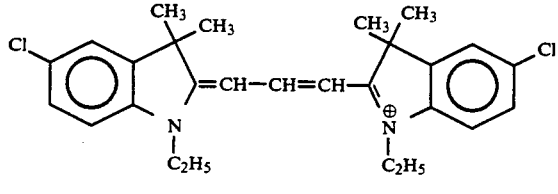 EX-12

-continued
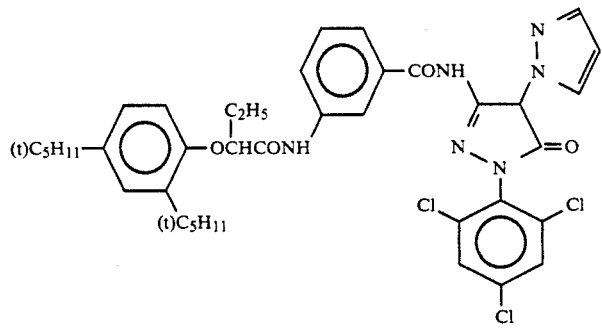 EX-13
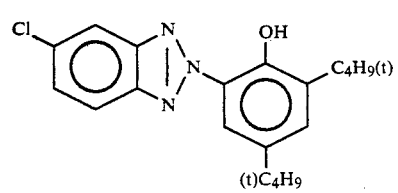 U-1
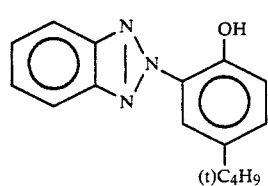 U-2
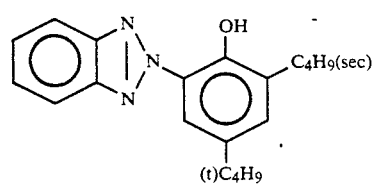 U-3
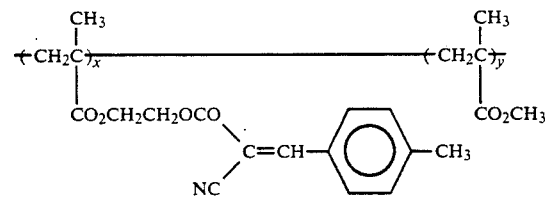 U-4
x:y = 70:30 (wt %)
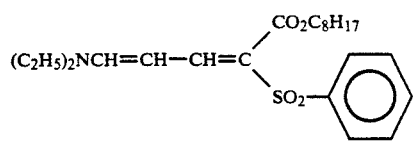 U-5
Tricresyl phosphate    HBS-1
Di-n-Butyl phthalate    HBS-2
HBS-3
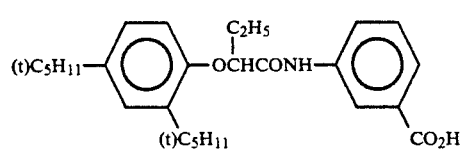

-continued
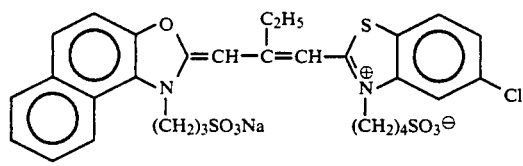
Sensitizing Dye I
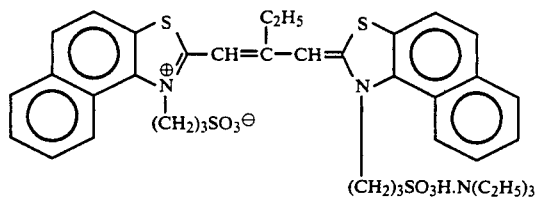
Sensitizing Dye II
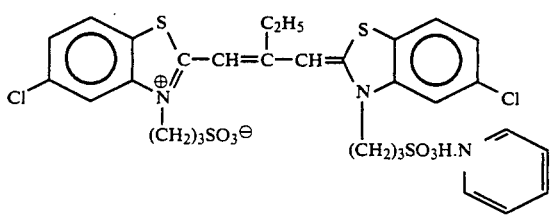
Sensitizing Dye III
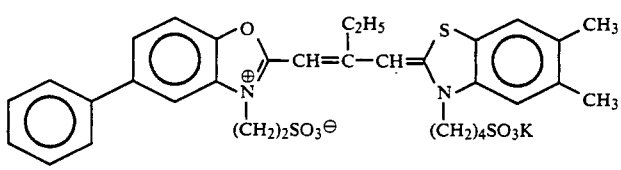
Sensitizing Dye IV
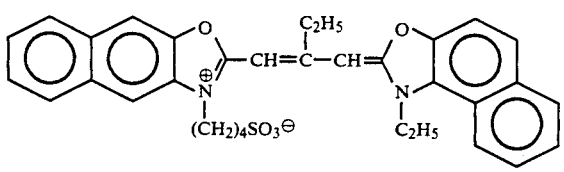
Sensitizing Dye V
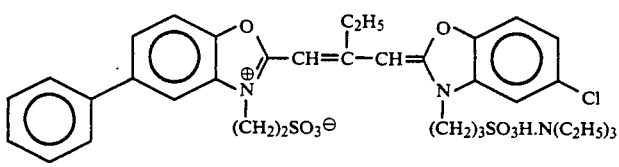
Sensitizing Dye VI
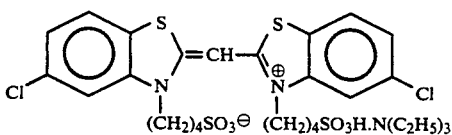
Sensitizing Dye VII
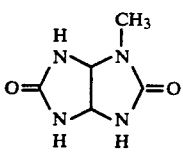
S-1
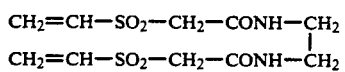
H-1
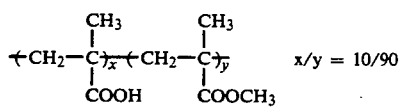
B-1

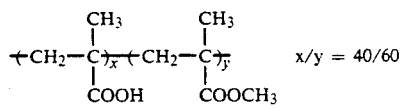 B-2
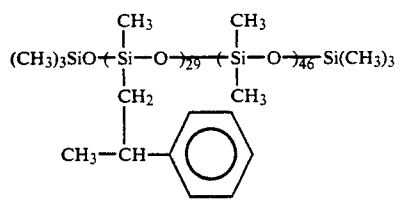 B-3
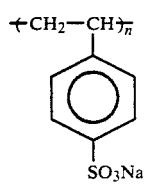 B-4
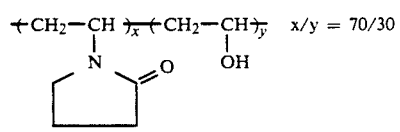 B-5
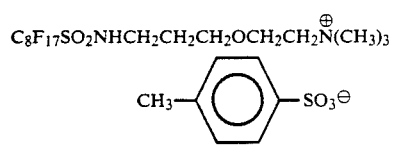 W-1
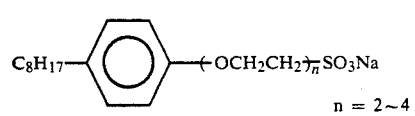 W-2
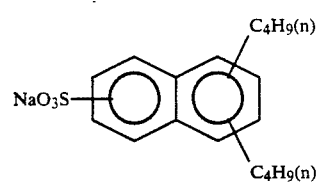 W-3
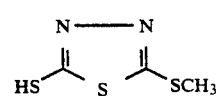 F-1
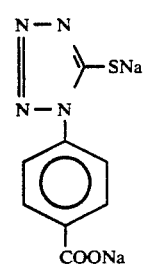 F-2

-continued
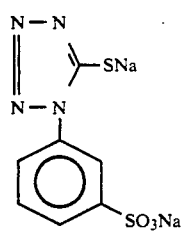 F-3
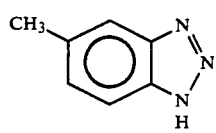 F-4
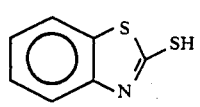 F-5
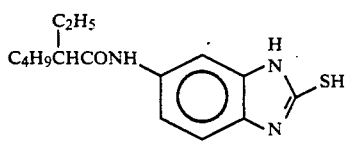 F-6
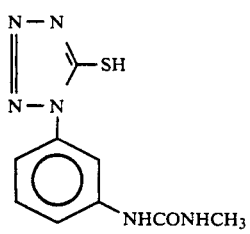 F-7
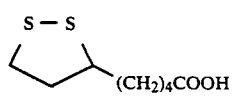 F-8
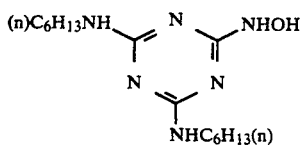 F-9
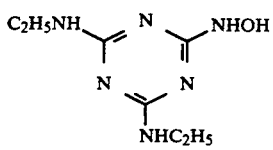 F-10
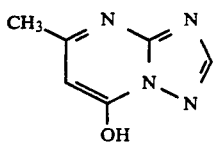 F-11
 F-12

-continued

F-13

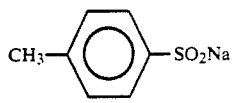

Samples 302 to 310 were prepared in the same manner as for Sample 301, except for replacing the cyan coupler (EX-2) in the 3rd, 4th, and 5th layers with the respective equimolar amount of the coupler shown in Table 6 below.

Each of Samples 301 to 310 was wedgewise exposed to red light and processed according to the following processing schedule (IV).

| Processing Schedule (IV): | | |
|---|---|---|
| Step | Temp. | Time |
| Color Development | 38° C. | 3'15" |
| Bleach | 38° C. | 1'00" |
| Bleach-fix | 38° C. | 3'15" |
| Washing (1) | 35° C. | 40" |
| Washing (2) | 35° C. | 1'00" |
| Stabilization | 38° C. | 40" |
| Drying | 55° C. | 1'15" |

Each processing solution used had the following composition:

| Color Developing Solution: | |
|---|---|
| Diethylenetriaminepentaacetic acid | 1.0 g |
| 1-Hydroxyethylidene-1,1-diphosphonic acid | 3.0 g |
| Sodium sulfite | 4.0 g |
| Potassium carbonate | 30.0 g |
| Potassium bromide | 1.4 g |
| Potassium iodide | 1.5 mg |
| Hydroxylamine sulfate | 2.4 g |
| 4-[N-Ethyl-N-β-hydroxyethylamino]-2-methylaniline sulfate | 4.5 g |
| Water to make | 1.0 l |
| pH | 10.05 |
| Bleaching Bath: | |
| Ammonium (ethylenediaminetetra-acetato)iron (II) dihydrate | 120.0 g |
| Disodium ethylenediaminetetraacetate | 10.0 g |
| Ammonium bromide | 100.0 g |
| Ammonium nitrate | 10.0 g |
| Bleaching Accelerator: | |
| [(H$_3$C)$_2$N—CH$_2$—CH$_2$—S$\frac{}{2}$]·2HCl | 0.005 mol |
| Aqueous ammonia (27%) | 15.0 ml |
| Water to make | 1.0 l |
| pH | 6.3 |
| Bleach-Fix Bath: | |
| Ammonium (ethylenediaminetetra-acetato)iron (II) dihydrate | 50.0 g |
| Disodium ethylenediaminetetraacetate | 5.0 g |
| Sodium sulfite | 12.0 g |
| Aqueous ammonium thiosulfate (700 g/l) | 240.0 ml |
| Aqueous ammonia (27%) | 6.0 ml |
| Water to make | 1.0 l |
| pH | 7.2 |

Washing Water:

Tap water was passed through a mixed bed column packed with an H-type strongly acidic cation exchange resin Amberlite IR-120B (produced by Rohm & Haas Co.) and an OH-type anion exchange resin IR-400 (produced by Rohm & Haas Co.) to reduce calcium and magnesium ions to 3 mg/l or less, respectively. To the thus treated water were added 20 mg/l of sodium isocyanurate dichloride and 0.15 g/l of sodium sulfate. The resulting washing water had a pH between 6.5 and 7.5.

| Stabilizing Bath: | |
|---|---|
| Formalin (37%) | 2.0 ml |
| Polyoxyethylene-p-mononoyl phenyl ether (average degree of polymerization: 10) | 0.3 g |
| Disodium ethylenediaminetetraacetate | 0.05 g |
| Water to make | 1.0 l |
| pH | 5.0–8.0 |

Red density of each of the colored samples 301 to 310 was measured with a Fuji type densitometer, and the activity was expressed as a relative value of tangent G of the straight line connecting the points of the cyan image densities being fog density+0.5 and fog density+1.0 with the tangent G for Sample 301 taken as 1.00. The dye image stability of the samples was evaluated in the same manner as in Example 1 except that the initial density of cyan image was taken as 1.5.

TABLE 6

| Sample No. | Coupler No. | Relative Activity* | Image Stability (%) | Remark |
|---|---|---|---|---|
| 301 | EX-2 | 1.00 | 97 | Comparison |
| 302 | (1) | 1.21 | 98 | Invention |
| 303 | (6) | 1.15 | 100 | " |
| 304 | (7) | 1.23 | 97 | " |
| 305 | (12) | 1.17 | 97 | " |
| 306 | (27) | 1.14 | 99 | " |
| 307 | (31) | 1.29 | 98 | " |
| 308 | (33) | 1.27 | 98 | " |
| 309 | (52) | 1.21 | 99 | " |
| 310 | (53) | 1.29 | 99 | " |

Note:
*Activity of Sample 301 was taken as a standard (1.00).

It can be seen from Table 6 that the cyan couplers of the present invention exhibit high relative activity and provide a dye image having satisfactory stability when applied to multi-layer color light-sensitive materials for photography (color negative films).

EXAMPLE 4

Preparation of Sample 401

On a 127 μm thick cellulose triacetate film support having a subbing layer, the following layers were coated to prepare a multi-layer color light-sensitive material (designated Sample 401). The effects of the compounds added are not limited to the applications indicated.

| 1st Layer (Antihalation Layer): | |
|---|---|
| Black colloidal silver | 0.25 g/m$^2$ as Ag |
| Gelatin | 1.9 g/m$^2$ |
| Ultraviolet absorbent U-1 | 0.04 g/m$^2$ |
| Ultraviolet absorbent U-2 | 0.1 g/m$^2$ |
| Ultraviolet absorbent U-3 | 0.1 g/m$^2$ |
| Ultraviolet absorbent U-4 | 0.1 g/m$^2$ |
| Ultraviolet absorbent U-6 | 0.1 g/m$^2$ |
| High-boiling organic solvent | 0.1 g/m$^2$ |

Oil-1
2nd Layer (Intermediate Layer):
| | |
|---|---|
| Gelatin | 0.40 g/m² |
| Compound Cpd-D | 10 mg/m² |
| High-boiling organic solvent Oil-3 | 0.1 g/m² |
| Dye D-4 | 0.4 mg/m² |

3rd Layer (Intermediate Layer):
| | |
|---|---|
| Surface- and inside-fogged silver iodobromide fine grain emulsion (mean grain size: 0.06 μm; coefficient of variation: 18%; AgI content: 1 mol %) | 0.05 g/m² as Ag |
| Gelatin | 0.4 g/m² |

4th Layer (Low Sensitivity Red-Sensitive Emulsion Layer):
| | |
|---|---|
| Emulsion A | 0.2 g/m² as Ag |
| Emulsion B | 0.3 g/m² as Ag |
| Gelatin | 0.8 g/m² |
| Coupler C-1 | 0.15 g/m² |
| Coupler C-2 | 0.05 g/m² |
| Coupler C-9 | 0.05 g/m² |
| Compound Cpd-D | 10 mg/m² |
| High-boiling organic solvent Oil-2 | 0.1 g/m² |

5th Layer (Middle Sensitivity Red-Sensitive Emulsion Layer):
| | |
|---|---|
| Emulsion B | 0.2 g/m² as Ag |
| Emulsion C | 0.3 g/m² as Ag |
| Gelatin | 0.8 g/m² |
| Coupler C-1 | 0.2 g/m² |
| Coupler C-2 | 0.05 g/m² |
| Coupler C-3 | 0.2 g/m² |
| High-boiling organic solvent Oil-2 | 0.1 g/m² |

6th Layer (High Sensitivity Red-Sensitive Emulsion Layer):
| | |
|---|---|
| Emulsion D | 0.4 g/m² as Ag |
| Gelatin | 1.1 g/m² |
| Coupler C-1 | 0.3 g/m² |
| Coupler C-3 | 0.7 g/m² |
| Additive P-1 | 0.1 g/m² |

7th Layer (Intermediate Layer):
| | |
|---|---|
| Gelatin | 0.6 g/m² |
| Additive M-1 | 0.3 g/m² |
| Color mixing inhibitor Cpd-K | 2.6 mg/m² |
| Ultraviolet absorbent U-1 | 0.1 g/m² |
| Ultraviolet absorbent U-6 | 0.1 g/m² |
| Dye D-1 | 0.02 g/m² |

8th Layer (Intermediate Layer):
| | |
|---|---|
| Surface- and inside-fogged silver iodobromide emulsion (mean grain size: 0.06 μm; coefficient of variation: 16%; AgI content: 0.3 mol %) | 0.02 g/m² as Ag |
| Gelatin | 1.0 g/m² |
| Additive P-1 | 0.2 g/m² |
| Color mixing inhibitor Cpd-J | 0.1 g/m² |
| Color mixing inhibitor Cpd-A | 0.1 g/m² |

9th Layer (Low Sensitivity Green-Sensitive Emulsion Layer):
| | |
|---|---|
| Emulsion E | 0.3 g/m² as Ag |
| Emulsion F | 0.1 g/m² as Ag |
| Emulsion G | 0.1 g/m² as Ag |
| Gelatin | 0.5 g/m² |
| Coupler C-7 | 0.05 g/m² |
| Coupler C-8 | 0.20 g/m² |
| Compound Cpd-B | 0.03 g/m² |
| Compound Cpd-D | 10 mg/m² |
| Compound Cpd-E | 0.02 g/m² |
| Compound Cpd-F | 0.02 g/m² |
| Compound Cpd-G | 0.02 g/m² |
| Compound Cpd-H | 0.02 g/m² |
| High-boiling organic solvent Oil-1 | 0.1 g/m² |
| High-boiling organic solvent Oil-2 | 0.1 g/m² |

10th Layer (Middle Sensitivity Green-Sensitive Emulsion Layer):
| | |
|---|---|
| Emulsion G | 0.3 g/m² as Ag |
| Emulsion H | 0.1 g/m² as Ag |
| Gelatin | 0.6 g/m² |
| Coupler C-7 | 0.2 g/m² |
| Coupler C-8 | 0.1 g/m² |
| Compound Cpd-B | 0.03 g/m² |
| Compound Cpd-E | 0.02 g/m² |
| Compound Cpd-F | 0.02 g/m² |
| Compound Cpd-G | 0.05 g/m² |
| Compound Cpd-H | 0.05 g/m² |
| High-boiling organic solvent Oil-2 | 0.01 g/m² |

11th Layer (High Sensitivity Green-Sensitive Emulsion Layer):
| | |
|---|---|
| Emulsion I | 0.5 g/m² as Ag |
| Gelatin | 1.0 g/m² |
| Coupler C-4 | 0.3 g/m² |
| Coupler C-8 | 0.1 g/m² |
| Compound Cpd-B | 0.08 g/m² |
| Compound Cpd-E | 0 02 g/m² |
| Compound Cpd-F | 0.02 g/m² |
| Compound Cpd-G | 0.02 g/m² |
| Compound Cpd-H | 0.02 g/m² |
| High-boiling organic solvent Oil-1 | 0.02 g/m² |
| High-boiling organic solvent Oil-2 | 0.02 g/m² |

12th (Intermediate Layer):
| | |
|---|---|
| Gelatin | 0.6 g/m² |
| Dye D-1 | 0.1 g/m² |
| Dye D-2 | 0.05 g/m² |
| Dye D-3 | 0.07 g/m² |

13th Layer (Yellow Filter Layer):
| | |
|---|---|
| Yellow colloidal silver | 0.1 g/m² as Ag |
| Gelatin | 1.1 g/m² |
| Color mixing inhibitor Cpd-A | 0.01 g/m² |
| High-boiling organic solvent Oil-1 | 0.01 g/m² |

14th Layer (Intermediate Layer):
| | |
|---|---|
| Gelatin | 0.6 g/m² |

15th Layer (Low Sensitivity Blue-Sensitive Emulsion Layer):
| | |
|---|---|
| Emulsion J | 0.4 g/m² as Ag |
| Emulsion K | 0.1 g/m² as Ag |
| Emulsion L | 0.1 g/m² as Ag |
| Gelatin | 0.8 g/m² |
| Coupler C-5 | 0.6 g/m² |

16th Layer (Middle Sensitivity Blue-Sensitive Emulsion Layer):
| | |
|---|---|
| Emulsion L | 0.1 g/m² as Ag |
| Emulsion M | 0.4 g/m² as Ag |
| Gelatin | 0.9 g/m² |
| Coupler C-5 | 0.3 g/m² |
| Coupler C-6 | 0.3 g/m² |

17th Layer (High Sensitivity Blue-Sensitive Emulsion Layer):
| | |
|---|---|
| Emulsion N | 0.4 g/m² as Ag |
| Gelatin | 1.2 g/m² |
| Coupler C-6 | 0.7 g/m² |

18th Layer (1st Protective Layer):
| | |
|---|---|
| Gelatin | 0.7 g/m² |
| Ultraviolet absorbent U-1 | 0.04 g/m² |
| Ultraviolet absorbent U-2 | 0.01 g/m² |
| Ultraviolet absorbent U-3 | 0.03 g/m² |
| Ultraviolet absorbent U-4 | 0.03 g/m² |
| Ultraviolet absorbent U-5 | 0.05 g/m² |
| Ultraviolet absorbent U-6 | 0.05 g/m² |
| High-boiling organic solvent Oil-1 | 0.02 g/m² |

Formalin scavenger:
| | |
|---|---|
| Cpd-C | 0.2 g/m² |
| Cpd-I | 0.4 g/m² |
| Dye D-3 | 0.05 g/m² |

19th Layer (2nd Protective Layer):
| | |
|---|---|
| Colloidal silver | 0.1 mg/m² as Ag |
| Silver iodobromide fine grain emulsion (mean grain size: 0.06 μm; AgI content: 1 mol %) | 0.1 g/m² as Ag |
| Gelatin | 0.4 g/m² |

20th Layer (3rd Protective Layer):

| | | | |
|---|---|---|---|
| Gelatin | | | 0.4 g/m² |
| Polymethyl methacrylate (average particle size: 1.5 μm) | | | 0.1 g/m² |
| Methyl methacrylate/acrylic acid copolymer (average particle size: 1.5 μm) | | | 0.1 g/m² |
| Silicone oil | | | 0.03 g/m² |
| Surface active agent W-1 | | | 3.0 mg/m² |
| Surface active agent W-2 | | | 0.03 g/m² |

Each of the above emulsion layers further contained additives F-1 to F-8. Further, a gelatin hardening agent H-1 and surface active agents W-3 and W-4 useful in coating and emulsifying were added to each layer. Furthermore, phenol, 1,2-benzisothiazolin-3-one, 2-phenoxyethanol, and phenethyl alcohol were added as antiseptics and antifungal agents.

The silver iodobromide emulsions used in Sample 401 and spectral sensitization method therefor are shown in Tables 7 and 8 below.

TABLE 7

| Emulsion No. | Grain Structure | Mean Grain Size (μm) | Coefficient of Variation (%) | AgI Content (mol %) |
|---|---|---|---|---|
| A | monodispersed tetradecahedral grains | 0.25 | 16 | 3.7 |
| B | monodispersed cubic internal latent image type grains | 0.30 | 10 | 3.3 |
| C | monodispersed tetradecahedral grains | 0.30 | 18 | 5.0 |
| D | polydispersed twin grains | 0.60 | 25 | 2.0 |
| E | monodispersed cubic grains | 0.17 | 17 | 4.0 |
| F | monodispersed cubic grains | 0.20 | 16 | 4.0 |
| G | monodispersed cubic internal latent image type grains | 0.25 | 11 | 3.5 |
| H | monodispersed cubic internal latent image type grains | 0.30 | 9 | 3.5 |
| I | polydispersed tabular grains (average aspect ratio: 4.0) | 0.80 | 28 | 1.5 |
| J | monodispersed tetradecahedral grains | 0.30 | 18 | 4.0 |
| K | monodispersed tetradecahedral grains | 0.37 | 17 | 4.0 |
| L | monodispersed cubic internal latent image type grains | 0.46 | 14 | 3.5 |
| M | monodispersed cubic grains | 0.55 | 13 | 4.0 |
| N | polydispersed tabular grains (average aspect ratio: 7.0) | 1.00 | 33 | 1.3 |

TABLE 8

| Emulsion No. | Sensitizing Dye Kind | Amount (g/mol-AgX) | Stage of Addition of Sensitizing Dye |
|---|---|---|---|
| A | S-1 | 0.025 | immediately after chemical sensitization |
|   | S-2 | 0.25 | immediately after chemical sensitization |
| B | S-1 | 0.01 | immediately after completion of grain formation |
|   | S-2 | 0.25 | immediately after completion of grain formation |
| C | S-1 | 0.02 | immediately after chemical sensitization |
|   | S-2 | 0.25 | immediately after chemical sensitization |
| D | S-1 | 0.01 | immediately after chemical sensitization |
|   | S-2 | 0.10 | immediately after chemical sensitization |
|   | S-7 | 0.01 | immediately after chemical sensitization |
| E | S-3 | 0.5 | immediately after chemical sensitization |
|   | S-4 | 0.1 | immediately after chemical sensitization |
| F | S-3 | 0.3 | immediately after chemical sensitization |
|   | S-4 | 0.1 | immediately after chemical sensitization |
| G | S-3 | 0.25 | immediately after completion of grain formation |
|   | S-4 | 0.08 | immediately after completion of grain formation |
| H | S-3 | 0.2 | during grain formation |
|   | S-4 | 0.06 | during grain formation |
| I | S-3 | 0.3 | immediately before chemical sensitization |
|   | S-4 | 0.07 | immediately before chemical sensitization |
|   | S-8 | 0.1 | immediately before chemical sensitization |
| J | S-6 | 0.2 | during grain formation |
|   | S-5 | 0.05 | during grain formation |
| K | S-6 | 0.2 | during grain formation |
|   | S-5 | 0.05 | during grain formation |
| L | S-6 | 0.22 | immediately after completion of grain formation |
|   | S-5 | 0.06 | immediately after completion of grain formation |
| M | S-6 | 0.15 | immediately after chemical sensitization |
|   | S-5 | 0.04 | immediately after chemical sensitization |
| N | S-6 | 0.22 | immediately after completion of grain formation |
|   | S-5 | 0.06 | immediately after completion of grain formation |

Structural formulae or compound names of the compounds used in sample preparation are shown below.

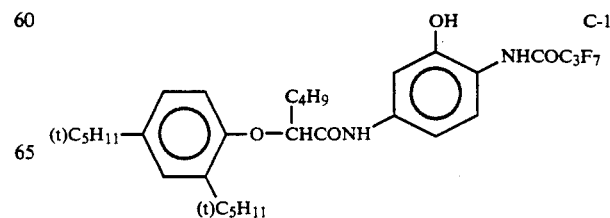

C-1

-continued
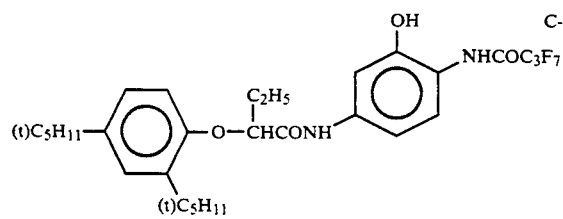
C-2
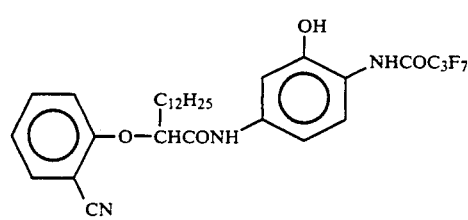
C-3
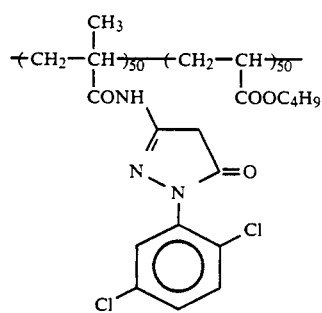
C-4
Copolymerization ratio: % by weight
Average molecular weight: ca. 25,000
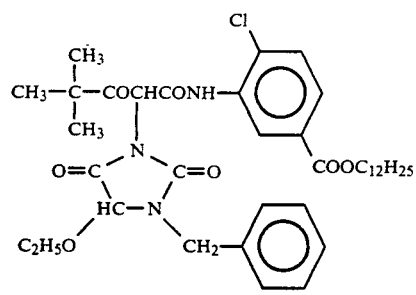
C-5
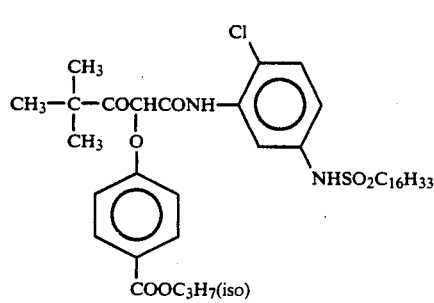
C-6
-continued
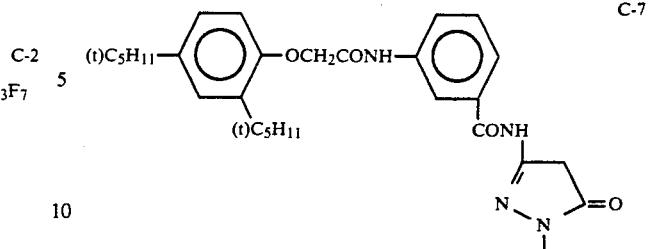
C-7
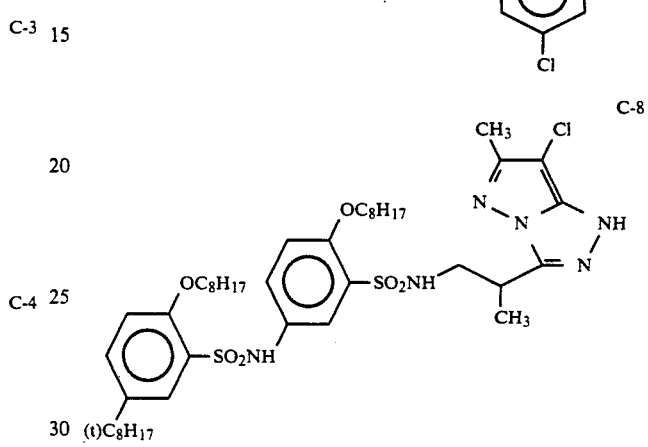
C-8
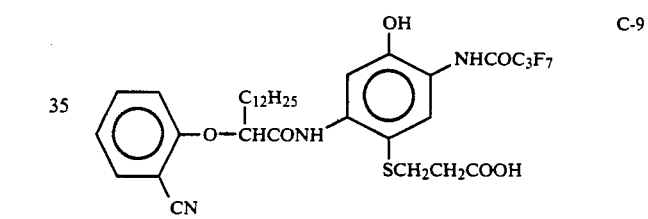
C-9
| | |
|---|---|
| Dibutyl phthalate | Oil-1 |
| Tricresyl phosphate | Oil-2 |
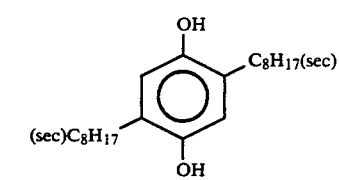
Oil-3
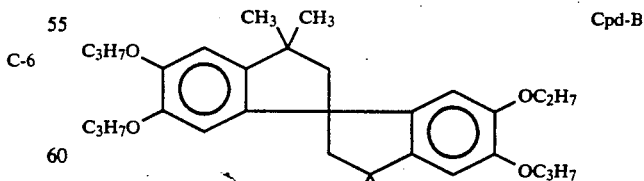
Cpd-A
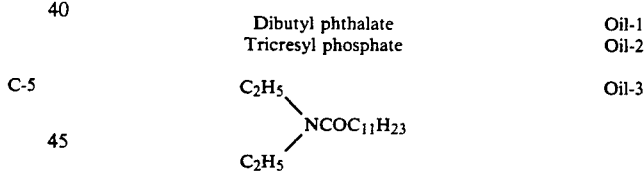
Cpd-B
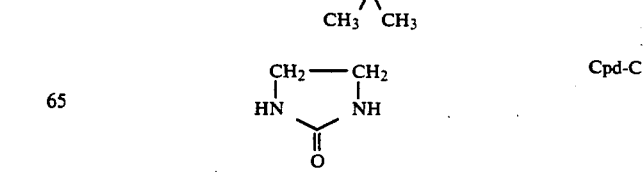
Cpd-C

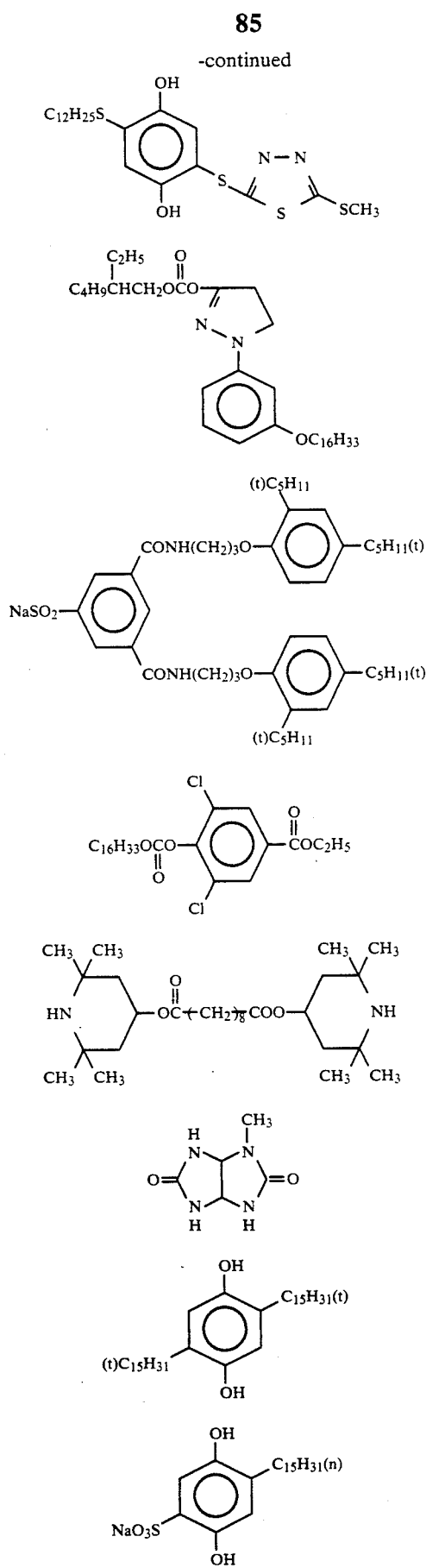
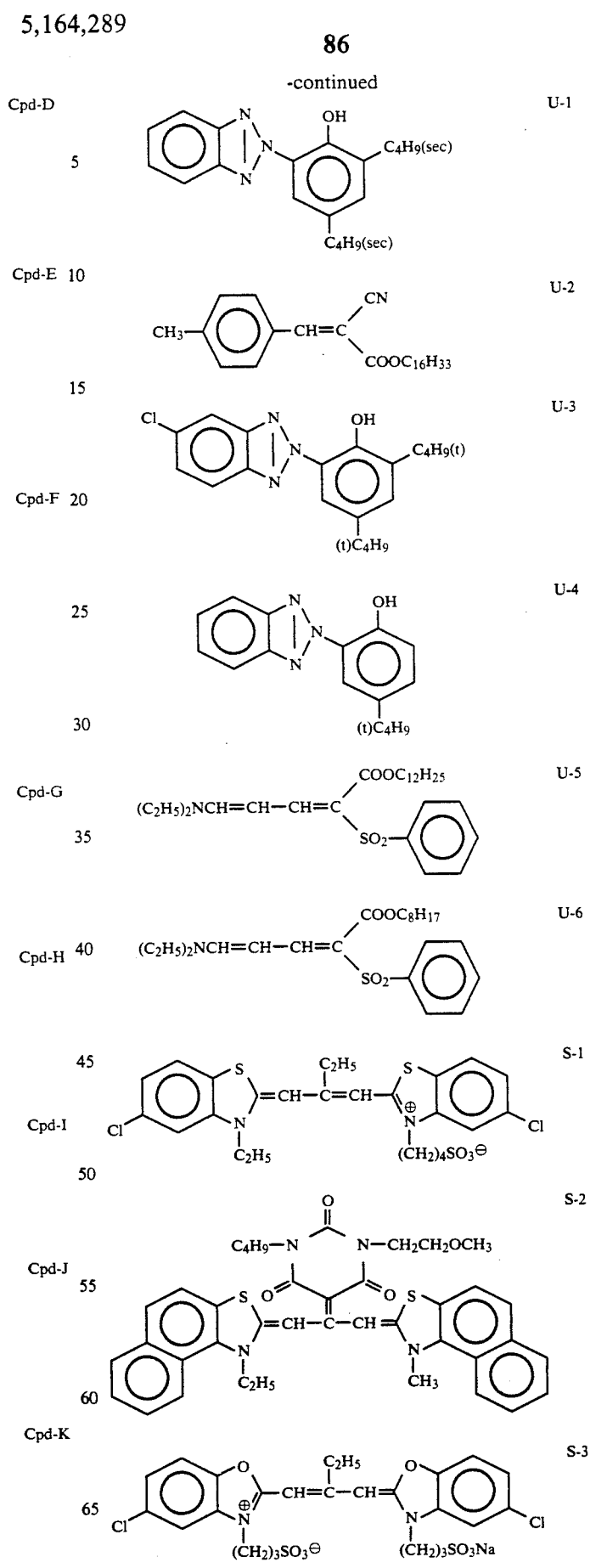

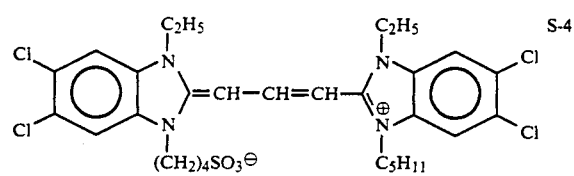
S-4
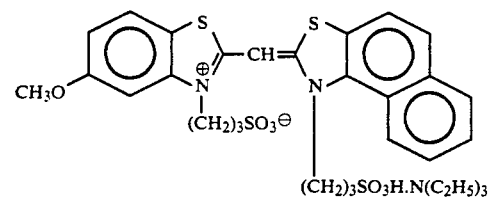
S-5
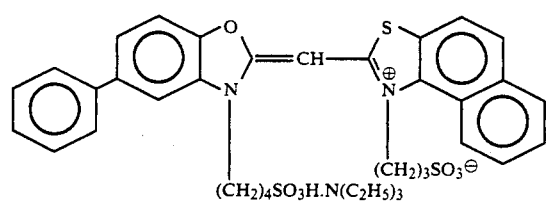
S-6
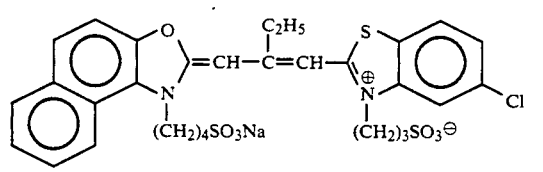
S-7
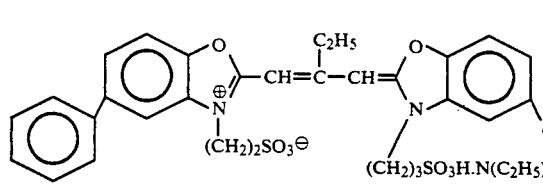
S-8
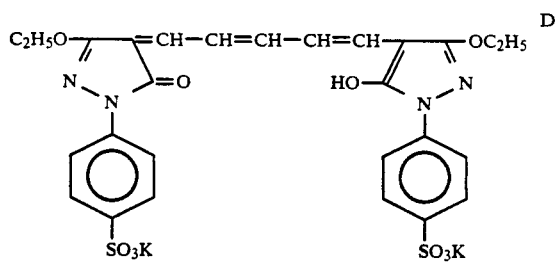
D-1
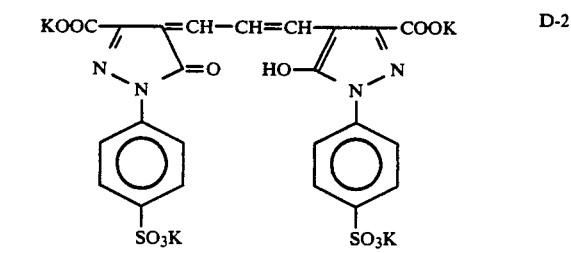
D-2
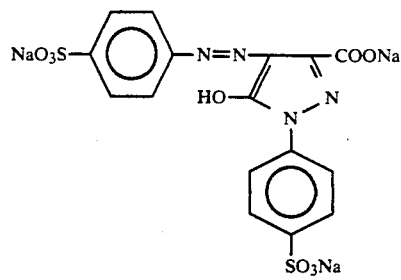
D-3
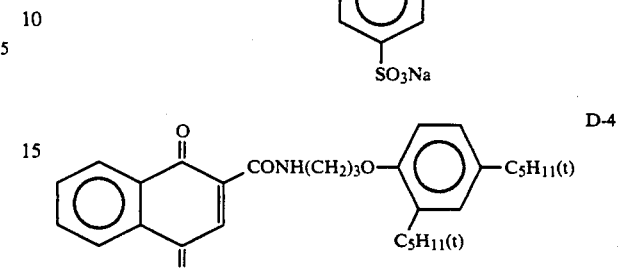
D-4
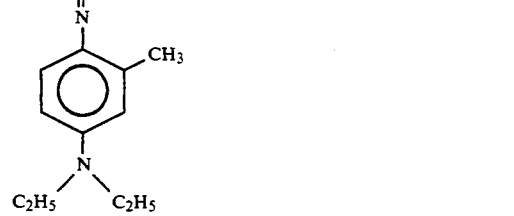
H-1
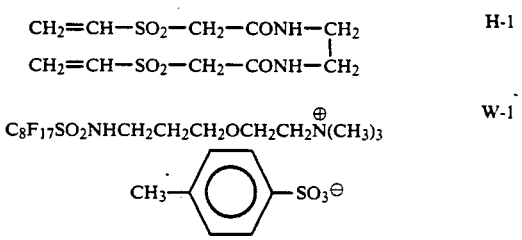
W-1
W-2
W-3
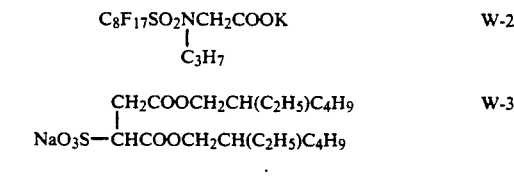
W-4
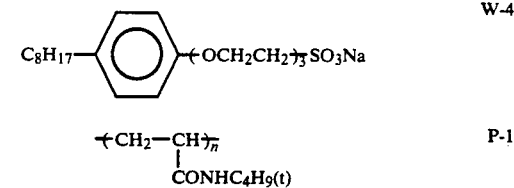
P-1
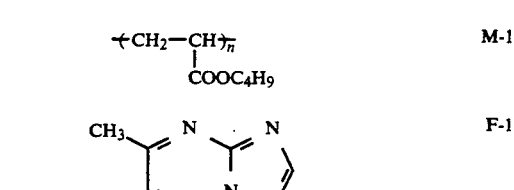
M-1
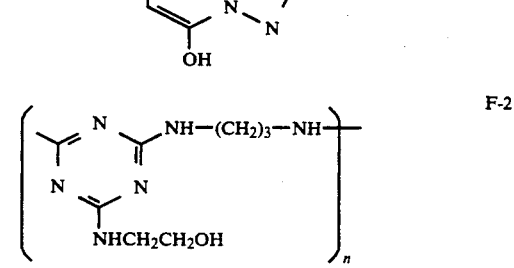
F-1
F-2

-continued

F-3 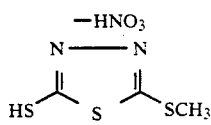

F-4 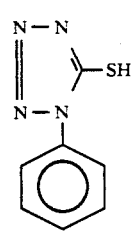

F-5 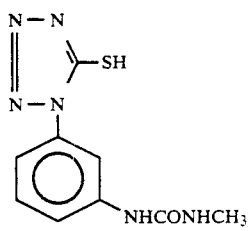

F-6 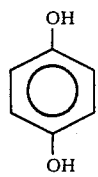

F-7 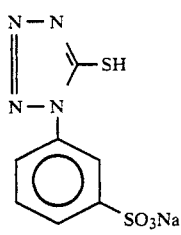

F-8 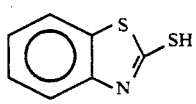

Preparation of Samples 402 to 407

Samples 402 to 407 were prepared in the same manner as for Sample 401, except for replacing the couplers C-1, C-2, C-3, and C-9 in the 4th, 5th, and 6th layers with the respective equimolar amount of cyan couplers shown in Table 9 below.

Each of Samples 401 to 407 was wedgewise exposed to red light and processed according to the schedule (V) shown below. The process samples were evaluated in the same manner as in Example 1. The results obtained are shown in Table 9.

| Processing Schedule (V): | | |
|---|---|---|
| Step | Time (min) | Temp. (°C.) |
| 1st Development | 6 | 38 |
| Washing | 2 | " |
| Reversing | 2 | " |
| Color development | 6 | " |

-continued

| Processing Schedule (V): | | |
|---|---|---|
| Step | Time (min) | Temp. (°C.) |
| Compensation | 2 | " |
| Bleach | 6 | " |
| Fixing | 4 | " |
| Washing | 4 | " |
| Stabilization | 1 | room temp. |
| Drying | 2 | 50 |

Each processing solution had the following composition:

| 1st Developing Solution: | |
|---|---|
| Water | 700 ml |
| Pentasodium nitrilo-N,N,N-trimethylenephosphonate | 2 g |
| Sodium sulfite | 20 g |
| Hydroquinone monosulfonate | 30 g |
| Sodium carbonate (monohydrate) | 30 g |
| 1-Phenyl-4-methyl-4-hydroxymethyl-3-pyrazolidone | 2 g |
| Potassium bromide | 2.5 g |
| Potassium thiocyanate | 1.2 g |
| Potassium iodide (0.1% solution) | 2 ml |
| Water to make | 1000 ml |
| pH (25° C.) | 9.6 |
| Reversing Bath: | |
| Water | 700 ml |
| Pentasodium nitrilo-N,N,N-trimethylenephosphonate | 3 g |
| Stannous chloride dihydrate | 1 g |
| p-Aminophenol | 0.1 g |
| Sodium hydroxide | 8 g |
| Glacial acetic acid | 15 ml |
| Water to make | 1000 ml |
| pH (25° C.) | 6.60 |
| Color Developing Solution: | |
| Water | 700 ml |
| Pentasodium nitrilo-N,N,N-trimethylenephosphonate | 3 g |
| Sodium sulfite | 7 g |
| Sodium tertiary phosphate dodecahydrate | 36 g |
| Potassium bromide | 1 g |
| Potassium iodide (0.1% solution) | 90 ml |
| Sodium hydroxide | 3 g |
| Citrazinic acid | 1.5 g |
| N-Ethyl-N-(β-methanesulfonamidoethyl)-3-methyl-4-aminoaniline sulfate | 11 g |
| 3,6-Dithiaoctane-1,8-diol | 1 g |
| Water to make | 1000 ml |
| pH | 11.90 |
| Compensating Solution: | |
| Water | 700 ml |
| Sodium sulfite | 12 g |
| Sodium ethylenediaminetetraacetate dihydrate | 8 g |
| Thioglycerin | 0.4 ml |
| Glacial acetic acid | 3 ml |
| Water to make | 1000 ml |
| pH (25° C.) | 6.00 |

The pH was adjusted with hydrochloric acid or sodium hydroxide.

| Bleaching Bath: | |
|---|---|
| Water | 800 ml |
| Sodium ethylenediaminetetraacetate dihydrate | 2 g |
| Ammonium (ethylenediaminetetraacetato)-iron (III) dihydrate | 120 g |
| Potassium bromide | 100 g |
| Water to make | 1000 ml |

-continued

| Bleaching Bath: | |
|---|---|
| pH (25° C.) | 6.0 |

The pH was adjusted with acetic acid or aqueous ammonia.

| Fixing Bath: | |
|---|---|
| Water | 800 ml |
| Sodium thiosulfate | 80.0 g |
| Sodium sulfite | 5.0 g |
| Sodium bisulfite | 5.0 g |
| Water to make | 1000 ml |
| pH (25° C.) | 6.00 |

The pH was adjusted with acetic acid or aqueous ammonia.

| Stabilizing Bath: | |
|---|---|
| Water | 800 ml |
| Formalin (37 wt %) | 5.0 ml |
| Fuji Dry Well (surface active agent produced by Fuji Photo Film Co., Ltd.) | 5.0 ml |
| Water to make | 1000 ml |
| pH (25° C.) | 7.0 |

TABLE 9

| Sample No. | Couplers in 4th, 5th & 6th Layers | Relative Color Developability* | Dye Image Stability | Remark |
|---|---|---|---|---|
| 401 | C-1, C-2, C-3, C-9 | 0.40 | 0.55 | Comparison |
| 402 | (1) | 1.00 | 0.97 | Invention |
| 403 | (6) | 0.98 | 0.98 | " |
| 404 | (12) | 1.00 | 0.98 | " |
| 405 | (33) | 1.20 | 0.99 | " |
| 406 | (52) | 1.21 | 0.99 | " |
| 407 | (53) | 1.20 | 0.99 | " |

Note: *Color developability of Sample 402 was taken as a standard (1.0).

The results of Table 9 prove that the cyan couplers according to the present invention exhibit excellent color developability and dye image stability when applied to color reversal light-sensitive materials.

As described and demonstrated above, the couplers of the present invention have excellent resistance against light and heat and provide a dye showing excellent absorption characteristics (i.e., a sharp absorption spectrum with no side absorption in the green light region and an improvement in color reproducibility).

The silver halide color photographic materials using the coupler of the present invention provide a dye image having excellent stability against light, heat or moisture and exhibit excellent color reproduction. Moreover, the silver halide color photographic materials achieve a high rate of dye formation in a color developing solution to give a high maximum color density. The high rate of dye formation and high maximum density are sufficiently maintained even when using a color developing solution containing no benzyl alcohol. With such silver halide color photographic materials, there is established a method for processing a silver halide photographic material, which causes substantially no reduction in density as has been observed when using a processing solution having bleaching ability with a weak oxidizing power (e.g., a processing solution having bleaching ability which contains sodium (ethylenediaminetetraacetato)iron (III) or ammonium (ethylenediaminetetraacetato)iron (III) as an oxidizing agent) or an exhausted processing solution having poor bleaching ability.

All publications disclosed herein including U.S. patents and literature references are herein incorporated by reference.

While the invention has been described in detail and with reference to specific examples thereof, it will be apparent to on skilled in the art that various changes and modifications can be made therein without departing from the spirit and scope thereof.

What is claimed is:

1. A silver halide photographic material containing at least one dye forming coupler represented by formula (I):

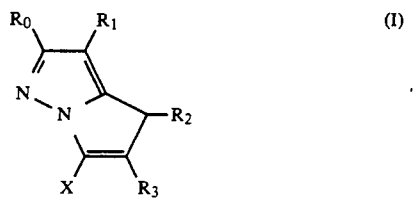

wherein $R_0$ represents a hydrogen atom or a substituent; $R_1$ and $R_3$ each represents a substituent; $R_2$ represents an electron attracting group; X represents a hydrogen atom or a group releasable on coupling with an oxidation product of an aromatic primary amine derivative.

2. The silver halide photographic material as claimed in claim 1, wherein $R_2$ is a substituent having a Hammett's $\sigma_p$ value of not less than 0.10.

3. The silver halide photographic material as claimed in claim 1, wherein $R_2$ is a substituent having a Hammett's $\sigma_p$ value of not less than 0.35.

4. The silver halide photographic material as claimed in claim 1, wherein $R_2$ is a substituent having a Hammett's $\sigma_p$ value of not less than 0.60.

5. The silver halide photographic material as claimed in claim 2, wherein $R_2$ represents a chlorine atom, a bromine atom, an iodine atom, a carboxyl group, a cyano group, a nitro group, a halogen-substituted alkyl group, an aliphatic, aromatic or heterocyclic acyl group, an aliphatic, aromatic or heterocyclic sulfonyl group, a carbamoyl group, an alkoxycarbonyl group, a substituted aromatic group, a heterocyclic residue, an azo group, a ditrifluoromethylamino group, a trifluoromethoxy group, an alkylsulfonyloxy group, an acyloxy group, an arylsulfonyloxy group, a phosphoryl group or a sulfamoyl group.

6. The silver halide photographic material as claimed in claim 3, wherein $R_2$ represents a cyano group, a nitro group, a carboxyl group, a fluorine-substituted alkyl group, an aliphatic, aromatic or heterocyclic acyl group, an aliphatic, aromatic or heterocyclic sulfonyl group, a carbamoyl group, an alkoxycarbonyl group, a fluorine- or sulfonyl-substituted aromatic group, a heterocyclic residue, an azo group, an alkylsulfonyloxy group, a phosphoryl group or a sulfamoyl group.

7. The silver halide photographic material as claimed in claim 4, wherein $R_2$ represents a cyano group, a nitro group or an aliphatic, aromatic or heterocyclic sulfonyl group.

8. The silver halide photographic material as claimed in claim 1, wherein $R_2$ represents a cyano group.

9. The silver halide photographic material as claimed in claim 1, wherein $R_0$ represents a hydrogen atom or a substituent and $R_1$ and $R_3$ each represents a substituent, said substituent for $R_0$, $R_1$ and $R_3$ representing a halogen atom, an aliphatic group, an aromatic group, a heterocyclic group, an alkoxy group, an aryloxy group, a heterocyclic oxy group, an aliphatic or aromatic thio group, an acyloxy group, a carbamoyloxy group, a sulfonyloxy group, an acylamino group, an anilino group, a ureido group, a sulfamoylamino group, an alkenyloxy group, an amino group, an aliphatic, aromatic or heterocyclic acyl group, an aliphatic, aromatic or heterocyclic sulfonyl group, a sulfinyl group, an aliphatic, aromatic or heterocyclic oxycarbonyl group, an aliphatic, aromatic or heterocyclic oxycarbonylamino group, a sulfonamido group, a carbamoyl group, a sulfamoyl group, a sulfamido group, an imido group, a hydroxyl group, a cyano group, a carboxyl group, a nitro group or a sulfo group.

10. The silver halide photographic material as claimed in claim 1, wherein $R_1$ is a substituent having a Hammett's $\sigma_p$ value of not less than 0.10.

11. The silver halide photographic material as claimed in claim 1, wherein $R_1$ is a substituent having a Hammett's $\sigma_p$ value of not less than 0.35.

12. The silver halide photographic material as claimed in claim 1, wherein $R_3$ is a substituent having a Hammett's $\sigma_p$ value of not less than 0.10.

13. The silver halide photographic material as claimed in claim 1, wherein $R_3$ is a substituent having a Hammett's $\sigma_p$ value of not less than 0.35.

14. The silver halide photographic material as claimed in claim 1, wherein X represents a hydrogen atom, a halogen atom, an alkoxy group, an aryloxy group, an acyloxy group, an aliphatic or aromatic sulfonyloxy group, an acylamino group, an aliphatic or aromatic sulfonamido group, an alkoxycarbonyloxy group, an aryloxycarbonyloxy group, an aliphatic, aromatic or heterocyclic thio group, a carbamoylamino group, a 5-membered or 6-membered nitrogen-containing heterocyclic group, an imido group or an aromatic azo group.

15. The silver halide photographic material as claimed in claim 1, wherein the coupler of formula (I) is present in an amount of from $1 \times 10^{-5}$ to $1 \times 10^{-2}$ mol per mol of silver halide.

16. A method for processing a silver halide color photographic material which comprises processing a color developed silver halide color photographic material containing at least one dye forming coupler represented by formula (I):

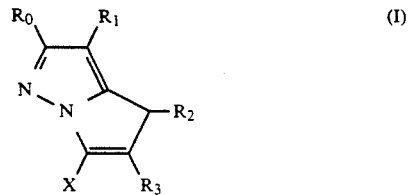

wherein $R_0$ represents a hydrogen atom or a substituent; $R_1$ and $R_3$ each represents a substituent; $R_2$ represents an electron attracting group; X represents a hydrogen atom or a group releasable on coupling with an oxidation product of an aromatic primary amine derivative.

* * * * *